US012359670B2

(12) United States Patent
Mebasser et al.

(10) Patent No.: US 12,359,670 B2
(45) Date of Patent: Jul. 15, 2025

(54) PAP SYSTEM BLOWER

(71) Applicant: ResMed Motor Technologies Inc., Chatsworth, CA (US)

(72) Inventors: Samuel Aziz Mebasser, Chatsworth, CA (US); Peter Jeffrey Thomas, Sylmar, CA (US); Roman Vinokur, Woodland Hills, CA (US); Kevin Gene McCulloh, Simi Valley, CA (US); William S Lane, Palmdale, CA (US); Yeu-chuan Hsia, Northridge, CA (US); Michael David Bednar, Playa del Rey, CA (US); John Paul Freese, Palmdale, CA (US); Karl Yutaka Iwahashi, Granada Hills, CA (US); David Brent Sears, Woodland Hills, CA (US); Barton John Kenyon, Sydney (AU); Richard G Krum, Camarillo, CA (US); Par Egron Dannas, Thousand Oaks, CA (US); Hiroshi Suzuki, Canyon Country, CA (US); Malcolm Edward Leader, Durango, CO (US)

(73) Assignee: ResMed Motor Technologies Inc., Chatsworth, CA (US)

( * ) Notice: Subject to any disclaimer, the term of this patent is extended or adjusted under 35 U.S.C. 154(b) by 0 days.

(21) Appl. No.: 18/396,820

(22) Filed: Dec. 27, 2023

(65) Prior Publication Data

US 2024/0125325 A1   Apr. 18, 2024

Related U.S. Application Data

(63) Continuation of application No. 17/887,147, filed on Aug. 12, 2022, now Pat. No. 11,859,622, which is a
(Continued)

(51) Int. Cl.
*F04D 25/06* (2006.01)
*A61M 16/00* (2006.01)
(Continued)

(52) U.S. Cl.
CPC ........ *F04D 25/0613* (2013.01); *F04D 17/16* (2013.01); *F04D 25/062* (2013.01);
(Continued)

(58) Field of Classification Search
CPC .... F04D 25/0613; F04D 25/062; F04D 25/08; F04D 29/056; F04D 29/403;
(Continued)

(56) References Cited

U.S. PATENT DOCUMENTS

| 2,401,386 A | 6/1946 | Smellie |
| 2,851,955 A | 9/1958 | Lapp |

(Continued)

FOREIGN PATENT DOCUMENTS

| CN | 2660187 Y | 12/2004 |
| CN | 2773558 Y | 4/2006 |

(Continued)

OTHER PUBLICATIONS

Extended European Search Report mailed Dec. 20, 2023 in International Application No. PCT 23175987.9, 12 pages.
(Continued)

*Primary Examiner* — Charles G Freay
(74) *Attorney, Agent, or Firm* — Nixon & Vanderhye P.C.

(57) ABSTRACT

A blower includes a housing including an inlet and an outlet, a bearing-housing structure provided to the housing and adapted to rotatably support a rotor, a motor provided to the bearing-housing structure and adapted to drive the rotor, and an impeller provided to the rotor. The bearing-housing structure includes a bearing shaft having a bearing surface
(Continued)

that rotatably supports the rotor. The bearing shaft provides only a single bearing of the non-ball bearing type for the rotor.

15 Claims, 71 Drawing Sheets

Related U.S. Application Data continuation of application No. 16/798,483, filed on Feb. 24, 2020, now Pat. No. 11,428,232, which is a continuation of application No. 14/112,072, filed as application No. PCT/US2012/034017 on Apr. 18, 2012, now Pat. No. 10,576,227.

(60) Provisional application No. 61/457,526, filed on Apr. 18, 2011, provisional application No. 61/630,920, filed on Dec. 22, 2011.

(51) Int. Cl.
| | |
|---|---|
| F04D 17/16 | (2006.01) |
| F04D 25/08 | (2006.01) |
| F04D 29/056 | (2006.01) |
| F04D 29/70 | (2006.01) |
| A61M 16/06 | (2006.01) |
| A61M 16/10 | (2006.01) |
| F04D 29/057 | (2006.01) |
| F04D 29/20 | (2006.01) |
| F04D 29/40 | (2006.01) |
| F04D 29/44 | (2006.01) |
| F04D 29/66 | (2006.01) |

(52) U.S. Cl.
CPC ........... *F04D 25/08* (2013.01); *F04D 29/056* (2013.01); *A61M 16/0066* (2013.01); *A61M 16/06* (2013.01); *A61M 16/0633* (2014.02); *A61M 16/0683* (2013.01); *A61M 16/107* (2014.02); *A61M 2205/0222* (2013.01); *A61M 2205/0238* (2013.01); *F04D 29/057* (2013.01); *F04D 29/20* (2013.01); *F04D 29/403* (2013.01); *F04D 29/441* (2013.01); *F04D 29/444* (2013.01); *F04D 29/668* (2013.01); *F04D 29/701* (2013.01); *F04D 29/703* (2013.01)

(58) Field of Classification Search
CPC .... F04D 29/441; F04D 29/444; F04D 29/701; F04D 29/703; F04D 17/16; A61M 16/0066; A61M 16/06; A61M 16/0683; A61M 16/10

See application file for complete search history.

(56) References Cited

U.S. PATENT DOCUMENTS

| | | | |
|---|---|---|---|
| 3,411,450 A | 11/1968 | Clifton | |
| 3,914,071 A | 10/1975 | Friese | |
| 4,430,590 A | 2/1984 | Davis | |
| 4,698,542 A | 10/1987 | Muller | |
| 5,574,321 A | 11/1996 | Baker | |
| 5,692,886 A | 12/1997 | Kobayashi | |
| 6,080,133 A | 6/2000 | Wampler | |
| 6,232,696 B1 | 5/2001 | Kim | |
| 6,280,156 B1 | 8/2001 | Wirz et al. | |
| 6,320,291 B1 | 11/2001 | Lin et al. | |
| 6,567,268 B1 | 5/2003 | Hsieh | |
| 6,753,628 B1 | 6/2004 | Neal | |
| 6,819,021 B1 | 11/2004 | Horng et al. | |
| 7,012,346 B2 | 3/2006 | Hoffman | |
| 7,230,357 B2 | 6/2007 | Rojo Lulic | |
| 7,448,383 B2 | 11/2008 | Delache et al. | |
| 7,508,102 B2 | 3/2009 | Sugiyama | |
| 7,748,381 B2 | 7/2010 | Croll | |
| 7,804,213 B2 | 9/2010 | Hoffman et al. | |
| 7,866,944 B2 | 1/2011 | Kenyon et al. | |
| 8,636,479 B2 * | 1/2014 | Kenyon | F04D 29/668 417/423.5 |
| 9,476,394 B2 | 10/2016 | Hayakawa | |
| 9,937,307 B2 * | 4/2018 | Sears | H02K 5/1732 |
| 10,576,227 B2 * | 3/2020 | Mebasser | F04D 29/056 |
| 11,428,232 B2 | 8/2022 | Mebasser et al. | |
| 11,428,322 B2 * | 8/2022 | Tanida | F16J 15/324 |
| 11,859,622 B2 * | 1/2024 | Mebasser | F04D 29/056 |
| 2002/0025261 A1 | 2/2002 | Kudo | |
| 2003/0035601 A1 | 2/2003 | Hsieh | |
| 2003/0108441 A1 | 6/2003 | Mackie | |
| 2003/0170121 A1 | 9/2003 | Lee et al. | |
| 2004/0108858 A1 * | 6/2004 | Wilcoxon | G01H 3/005 324/601 |
| 2004/0141841 A1 | 7/2004 | Otsuka | |
| 2004/0189125 A1 | 9/2004 | Doemen | |
| 2004/0234398 A1 | 11/2004 | Hu | |
| 2004/0245873 A1 | 12/2004 | Lu et al. | |
| 2004/0256933 A1 | 12/2004 | Toyokawa et al. | |
| 2005/0184609 A1 | 8/2005 | Chen | |
| 2006/0017341 A1 | 1/2006 | Hahn | |
| 2006/0192450 A1 | 8/2006 | Hsieh | |
| 2006/0237013 A1 | 10/2006 | Kwok | |
| 2007/0024137 A1 | 2/2007 | Otsuki et al. | |
| 2007/0044312 A1 | 3/2007 | Hirata et al. | |
| 2007/0108858 A1 | 5/2007 | Chou | |
| 2007/0120433 A1 | 5/2007 | Sugiyama et al. | |
| 2007/0183907 A1 | 8/2007 | Serowy | |
| 2007/0188034 A1 | 8/2007 | Yoshida | |
| 2007/0231163 A1 | 10/2007 | Liu | |
| 2007/0237438 A1 | 10/2007 | Ito | |
| 2007/0252464 A1 | 11/2007 | Cheng | |
| 2008/0014104 A1 | 1/2008 | Huang et al. | |
| 2008/0042039 A1 | 2/2008 | Krempel et al. | |
| 2008/0074009 A1 | 3/2008 | Enomoto | |
| 2008/0099023 A1 | 5/2008 | Berthon-Jones | |
| 2008/0267545 A1 | 10/2008 | Shih et al. | |
| 2008/0298983 A1 | 12/2008 | Tsai et al. | |
| 2008/0304986 A1 | 12/2008 | Kenyon et al. | |
| 2008/0310978 A1 | 12/2008 | Hoffman | |
| 2009/0035158 A1 | 2/2009 | Shih et al. | |
| 2009/0035162 A1 | 2/2009 | Yan et al. | |
| 2009/0046960 A1 | 2/2009 | Hibi et al. | |
| 2009/0053063 A1 | 2/2009 | Liang et al. | |
| 2009/0232678 A1 | 9/2009 | Yang et al. | |
| 2009/0246013 A1 | 10/2009 | Kenyon | |
| 2009/0266361 A1 | 10/2009 | Bilger | |
| 2009/0297078 A1 | 12/2009 | Hori et al. | |
| 2009/0320842 A1 | 12/2009 | Doherty et al. | |
| 2009/0324435 A1 | 12/2009 | Sears et al. | |
| 2010/0021294 A1 * | 1/2010 | Yeh | F04D 25/12 415/213.1 |
| 2010/0054965 A1 | 3/2010 | Teshima et al. | |
| 2010/0059056 A1 | 3/2010 | Sears et al. | |
| 2010/0124510 A1 | 5/2010 | Hsu et al. | |
| 2010/0177480 A1 | 7/2010 | Koplow | |
| 2010/0209270 A1 | 8/2010 | Yen et al. | |
| 2010/0215491 A1 | 8/2010 | Mockridge et al. | |
| 2010/0244601 A1 | 9/2010 | Shimizu et al. | |
| 2010/0266402 A1 | 10/2010 | Chen | |
| 2011/0014074 A1 | 1/2011 | Hoffman et al. | |
| 2011/0073110 A1 | 3/2011 | Kenyon et al. | |
| 2011/0238172 A1 | 9/2011 | Akdis | |
| 2012/0199129 A1 | 8/2012 | Kenyon | |
| 2014/0069432 A1 | 3/2014 | Mebasser et al. | |
| 2014/0369839 A1 | 12/2014 | Tamaoka | |
| 2020/0330709 A1 | 10/2020 | Mebasser et al. | |
| 2022/0381251 A1 | 12/2022 | Mebasser et al. | |

FOREIGN PATENT DOCUMENTS

| | | |
|---|---|---|
| CN | 1900537 A | 1/2007 |
| CN | 101324238 A | 12/2008 |

(56) References Cited

FOREIGN PATENT DOCUMENTS

| | | |
|---|---|---|
| CN | 101449064 A | 6/2009 |
| CN | 101963158 A | 2/2011 |
| EP | 0732794 A1 | 2/1996 |
| EP | 0 819 855 A1 | 1/1998 |
| EP | 1 591 668 A1 | 11/2005 |
| JP | 57-66297 | 10/1982 |
| JP | S58-117393 | 7/1983 |
| JP | S58-117394 | 7/1983 |
| JP | 63-306298 | 12/1988 |
| JP | 10-191595 A | 7/1998 |
| JP | 2000-341907 | 12/2000 |
| JP | 2002-34205 A | 1/2002 |
| JP | 2002-364589 A | 12/2002 |
| JP | 2003-56498 A | 2/2003 |
| JP | 2004-11525 A | 1/2004 |
| JP | 2004-208498 A | 7/2004 |
| JP | 2005-282500 A | 10/2005 |
| JP | 2005-315158 A | 11/2005 |
| JP | 2005-315236 A | 11/2005 |
| JP | 2006-2749 A | 1/2006 |
| JP | 2007-64082 A | 3/2007 |
| JP | 2007-506482 A | 3/2007 |
| JP | 2008-121688 A | 5/2008 |
| JP | 2008-240726 A | 10/2008 |
| JP | 2009-52485 A | 3/2009 |
| JP | 2009-178557 A | 8/2009 |
| JP | 2010-151207 A | 7/2010 |
| JP | 2010-196707 A | 9/2010 |
| JP | 2010-216462 A | 9/2010 |
| KR | 2000-0039553 A | 7/2000 |
| WO | WO 2005/008072 A1 | 1/2005 |
| WO | WO 2007/048206 | 5/2007 |
| WO | PCT/AU2010/001031 | 8/2010 |
| WO | PCT/AU2010/001106 | 8/2010 |
| WO | WO 2011/062633 | 5/2011 |

OTHER PUBLICATIONS

International Search Report for PCT/AU2012/034017, mailed Nov. 26, 2012.
Written Opinion for PCT/AU2012/034017, mailed Nov. 26, 2012.
First Examination Report issued in a corresponding New Zealand Application No. 616573 dated Apr. 30, 2014.
Extended European Search Report issued in corresponding EP Application No. 12 77 4367.2 dated Aug. 20, 2014.
Further Examination Report issued in corresponding New Zealand Appln. No. 616573 dated Mar. 31, 2015.
First Office Action issued in corresponding Chinese Appln. No. 201280019256.6 dated Apr. 20, 2015, with English translation thereof.
Patent Examination Report issued in corresponding Australian Appln. No. 2012245623 dated May 8, 2015.
First Examination Report issued in corresponding New Zealand Application No. 708592 dated Jun. 2, 2015.
Further Examination Report issued in corresponding New Zealand Application No. 616573 dated Jun. 22, 2015.
Second Office Action issued in corresponding Chinese Application No. 201280019256.6 dated Nov. 30, 2015, with English translation thereof.
First Office Action issued in corresponding Japanese Application No. 2014-506499 dated Feb. 1, 2016 with English translation thereof.
Patent Examination Report No. 2 issued in corresponding Australian Application No. 2012245623 dated Feb. 25, 2016.
Further Examination Report issued in corresponding New Zealand Application No. 708592 dated May 12, 2016.
Third Office Action issued in corresponding Chinese Patent Application No. 201280019256.6 dated Jun. 15, 2016 with English language translation thereof.
Decision of Rejection issued in a corresponding Japanese Patent Application No. 2014-506499 dated Sep. 16, 2016, with English language translation thereof.
Office Action dated Dec. 27, 2016 issued in Chinese Application No. 201280019256.6 with English translation (14 pages).
First Examination Report dated Dec. 9, 2016 issued in New Zealand Application No. 726185 (2 pages).
Communication dated Sep. 12, 2017 issued in European Application No. 12774357.2 (8 pages).
Office Action dated Oct. 23, 2017 issued in Japanese Application No. 2017-005000 with English translation (15 pages).
First Examination Report dated May 28, 2018 issued in New Zealand Application No. 741786 (2 pages).
Office Action dated Jun. 25, 2018 issued in Japanese Application No. 2017-005000 with English translation (8 pages).
Notice of Reasons for Rejection mailed Aug. 11, 2020 in Japanese Application No. 2019-160302, with English translation, 13 pages.
Final Rejection mailed Nov. 30, 2020 in Japanese Application No. 2019-160302, with English translation, 15 pages.
Mebasser et al, U.S. Appl. No. 17/887,147, filed Aug. 12, 2022, for "PAP System Blower," (parent application).
Notification of the First Office Action mailed May 7, 2023 in Chinese Application No. 202011229387.X, with English translation, 8 pages.
Notice of Reasons for Refusal mailed Dec. 16, 2024 in Japanese Application No. 2024-084862, with English translation, 15 pages.

* cited by examiner

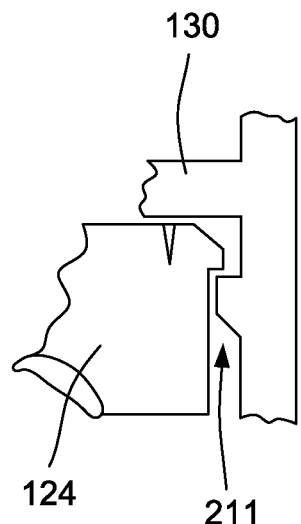
FIG. 59
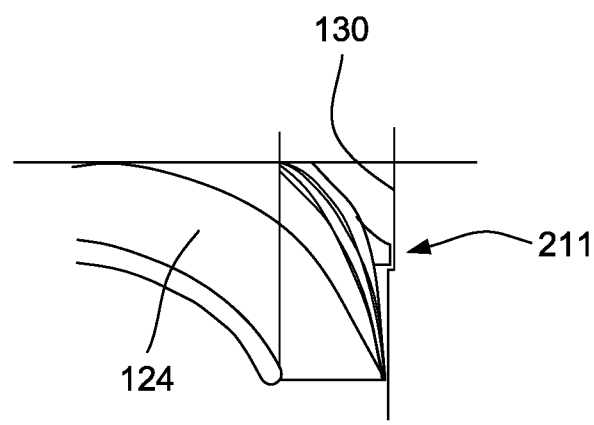
FIG. 60
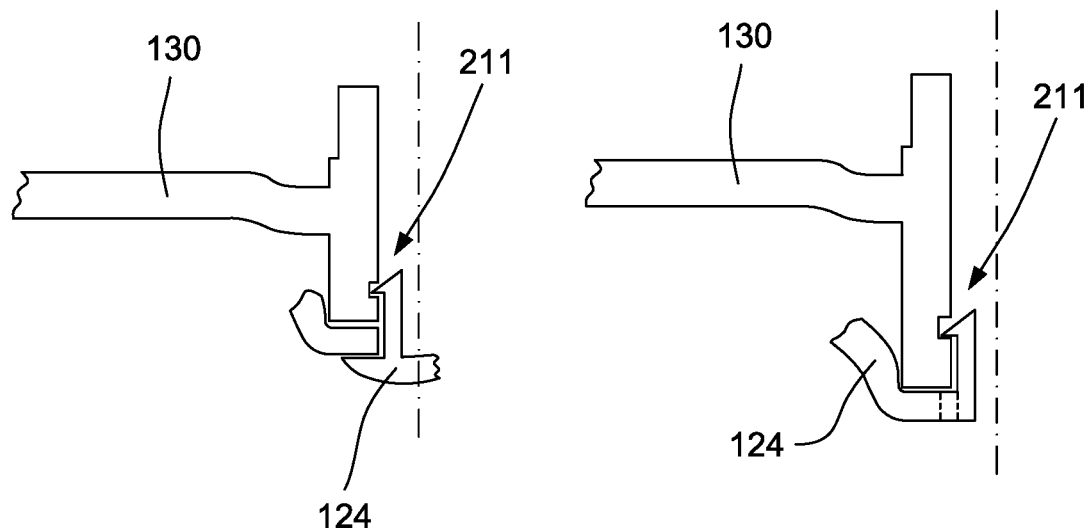
FIG. 61     FIG. 62

PAP SYSTEM BLOWER

CROSS-REFERENCE TO APPLICATIONS

This application is a continuation of U.S. application Ser. No. 17/887,147, filed Aug. 12, 2022, now U.S. Pat. No. 11,859,622 which is a continuation of U.S. application Ser. No. 16/798,483, filed Feb. 24, 2020, now U.S. Pat. No. 11,428,232, which is a continuation of U.S. application Ser. No. 14/112,072, filed Oct. 16, 2013, now U.S. Pat. No. 10,576,227, which is the U.S. national phase of International Application No. PCT/US2012/034017 filed 18 Apr. 2012 which designated the U.S. and claims the benefit of U.S. Provisional Application Nos. 61/457,526, filed Apr. 18, 2011, and 61/630,920, filed Dec. 22, 2011, each of which is incorporated herein by reference in its entirety.

Also, PCT Application No. PCT/AU2010/001106, filed Aug. 27, 2010, is incorporated herein by reference in its entirety.

FIELD OF TECHNOLOGY

The present technology relates to Positive Airway Pressure (PAP) systems and/or methods of use for treatment, e.g., of Sleep Disordered Breathing (SDB) with Continuous Positive Airway Pressure (CPAP) or Non-Invasive Positive Pressure Ventilation (NIPPY). More specifically, the present technology relates to blowers for PAP systems.

BACKGROUND OF TECHNOLOGY

Examples of head mounted blowers, wearable CPAP, or portable CPAP are known in the art. For example, see U.S. Patent Application Publications 2006/0237013 A1 and 2009/0320842 A1, each incorporated herein by reference in its entirety, and the BreatheX™ system.

SUMMARY OF TECHNOLOGY

Certain examples of the present technology relate to minimalistic CPAP systems, methods of use, and devices structured to at least reduce impact on the patient.

Certain examples of the present technology relate to patient interfaces that incorporates a relatively small or miniature blower.

Certain examples of the present technology relate to a blower that has a very small size, low cost and/or ease of assembly.

One aspect of the present technology relates to a new small blower for use in a PAP delivery unit that is designed to provide pressure support to a user. For example, the PAP delivery unit may provide low level pressure support of approximately 1-8 cm $H_2O$, e.g., operated at a speed of approximately 15,000 rpm and/or flow approximately 70 L/min. However, pressure support at higher levels, such as 1-25 cm $H_2O$, may also be provided.

Certain examples of the present technology relate to a blower in which the inlet and the outlet are axially aligned with an axis of the blower.

Certain examples of the present technology relate to a blower in which the housing includes an axial aligned inlet and an outlet that is tangential to the inlet.

Another aspect of the present technology relates to a blower that does not use or require ball bearings. Instead, the blower may include a central bearing structure, e.g., formed at least in part out of a low friction lubricious material such as sintered bronze, an engineered plastic material, e.g., a polyamide-imide resin such as a Torlon™, and/or other very low friction materials and/or other materials coated with a low friction material. The bearing may have a large bearing surface that surrounds a rotor or shaft, e.g., a highly polished shaft. The central bearing structure may include a radial sleeve bearing portion and a thrust bearing portion. The thrust bearing portion may utilize low friction materials, e.g., as described above.

Another aspect of the present technology relates to a blower that includes or requires only a single bearing structure including a radial bearing portion and a thrust bearing portion, which may assist in reducing the height of the blower. A thrust load may be provided on a top surface of the bearing. The radial bearing portion may be configured as a sleeve bearing along the surface of the shaft. As there is only a single bearing, the motor only requires balancing in one plane and not two planes.

Another aspect of the present technology relates to a disk-like bearing-housing structure to provide support to a rotor or shaft. The disk part of the bearing-housing structure may also provide a shielding function to prevent blade pass tonal noise from being generated from de-swirling vanes when an impeller spins. The top surface of the bearing-housing structure surrounding the shaft and adjacent the rotor cap may perform the bearing function by providing a radial surface along the shaft and a thrust surface to allow the parts to rotate. The stator components of the motor may be attached to the bearing-housing structure.

Another aspect of the present technology relates to a rotor retention design in which the rotor and/or rotor assembly are prevented from lifting off or separating from the blower housing.

Another aspect of the present technology relates to a bearing grease retention design within the bearing-housing structure to provide a reservoir of grease for supply to the thrust surface.

Another aspect of the present technology relates to a nested design in which the motor (stator component, fixed magnet and/or rotor cap) are at least partially nested within the impeller to reduce the size of the blower. The impeller may be directly molded or over-molded onto the rotor cap.

Another aspect of the present technology relates to an impeller having a rotor portion integrated therein. The conjoined impeller and rotor may comprise at least some ferrous material, such as magnetic steel, that provides a path for magnetic flux of a permanent magnet or magnets to pass therethrough, to cause rotation of the impeller through the interaction of the flux with that of a stator, e.g., a commutated motor stator.

Another aspect of the present technology relates to an impeller that may be retained on a rotor or shaft by a magnetic retention between the magnet coupled to the inner surface of a rotor cap and a stator component. There is no required fastening of the impeller to the rotor or shaft.

Another aspect of the present technology relates to blades of the impeller that curve in towards the hub having a slight S-like shape. The shape may be designed to reduce vortex shedding.

Another aspect of the present technology relates to an impeller. The impeller may be of the double shrouded type or an alternating shroud impeller as the shrouds may not fully cover the top and/or bottom surfaces of the impeller blades. An alternative is to use a bottom substantially fully shrouded impeller to help address an issue of the impeller lifting off the rotor or shaft in use.

Certain examples of the present technology relate to CPAP systems, methods of use and devices structured to at least reduce size and bulk, reduce vibrations, reduce generated noise or combinations thereof.

Certain examples of the present technology relate to small CPAP devices configured to supply pressurized breathable gas (e.g., air) in a manner suitable for treatment of sleep apneas and/or snoring.

Certain examples of the present technology relate to PAP systems including a patient interface including sealing arrangement adapted to form a seal with the patient's nose and/or mouth and headgear to support the sealing arrangement in position on the patient's head. A blower is structured to generate a supply of pressurized air. The blower is supported by the patient interface on the patient's head (e.g., within or formed as part of the headgear or cushion (e.g., integrated with a nozzle or nozzles) and in communication with the patient interface. The headgear may form one or more ducts to communicate pressurized air from the blower to a breathing cavity defined by the sealing arrangement. Alternatively, a separate tube may be provided to communicate pressurized air from the blower to the sealing arrangement.

In certain examples, PAP systems are disclosed that may be configured to provide a minimal visual footprint in use. The flow generator of such PAP systems comprises at least one blower and/or at least one blower housing and are in air communication with a patient interface. In addition, these PAP systems may include other structural elements (for example, but not limited, to headgear, shoulder-type harnesses, pendant-type arrangements, articles of clothing, straps or band arrangements or combinations thereof) resulting in PAP systems that may be portable, carried by the patient, used for travel, mask mounted, head mounted, located within or beside a pillow, configured for attachment to bed, configured for attachment to a headboard, configured for attachment to a chair or wheelchair, or combinations thereof.

In certain examples, the PAP system may be used in a hygiene device to filter air. The hygiene device may provide clean or purified, filtered air to a user. The filtered air may be pressurized. The hygiene device would include a filter designed to remove particulate matter from the air to deliver the purified air to the user.

In certain examples, the blower may include a width of about 60-65 mm, e.g., 62.8 mm, and a height of about 20-25 mm, e.g., 23.2 mm.

Another aspect of the present technology relates to a blower including a housing including an inlet and an outlet, a bearing-housing structure provided to the housing and adapted to rotatably support a rotor, a motor provided to the bearing-housing structure and adapted to drive the rotor, and an impeller provided to the rotor. The bearing-housing structure includes a bearing shaft having a bearing surface that rotatably supports the rotor. The bearing shaft provides only a single bearing structure of the non-ball bearing type for the rotor.

Another aspect of the present technology relates to a blower including a housing including an inlet and an outlet, a bearing-housing structure provided to the housing and adapted to rotatably support a rotor, a motor provided to the bearing-housing structure and adapted to drive the rotor, and an impeller provided to the rotor, wherein the motor is at least partially nested within the impeller.

Another aspect of the present technology relates to a blower including a housing including an inlet and an outlet, a bearing-housing structure provided to the housing and adapted to rotatably support a rotor, a motor provided to the bearing-housing structure and adapted to drive the rotor, and an impeller provided to the rotor, wherein the impeller is retained on the rotor by magnetic retention.

Another aspect of the present technology relates to a blower including a housing including an inlet and an outlet, a bearing-housing structure provided to the housing and adapted to rotatably support a rotor, a motor provided to the bearing-housing structure and adapted to drive the rotor, and an impeller provided to the rotor, wherein the bearing-housing structure is constructed of or coated with a low friction material or a lubricous material. The lubricous material including sintered bronze, an engineered plastic material, e.g., a polyamide-imide resin such as a Torlon™ and/or other very low friction materials. The bearing-housing structure may be constructed of a combination of materials including a lubricous material or a material having a very low coefficient of friction. For example, a first material, such as an aluminum, steel, brass, bronze or other metal or plastic, may be coated with a lubricous material or material having a very low coefficient of friction such as a ceramic based or a nickel based coating material. In certain examples, the coating may be applied only to the critical wear surfaces of the bearing-housing such as the shaft receiving surface. Alternatively or additionally, the shaft may be coated with such materials to reduce friction.

Another aspect of the present technology relates to a blower including a housing including an inlet and an outlet, a bearing-housing structure provided to the housing and adapted to rotatably support a rotor, a motor provided to the bearing-housing structure and adapted to drive the rotor, and an impeller provided to the rotor, wherein the bearing-housing structure includes a bearing shaft that rotatably supports the rotor and an annular disk that substantially aligns with or extends radially beyond the outer edge of the impeller to provide a shielding function.

Another aspect of the present technology relates to a blower including a housing including an inlet and an outlet, a bearing-housing structure provided to the housing and adapted to rotatably support a rotor, a motor provided to the bearing-housing structure and adapted to drive the rotor, and an impeller provided to the rotor. The bearing-housing structure includes a bearing shaft having a bearing surface that rotatably supports the rotor. The motor includes a stator assembly, a magnet, and a rotor cap. The rotor cap includes an interior surface that supports the magnet and an exterior surface that supports the impeller. The rotor cap is engaged with the rotor such that the stator assembly acts on the magnet to cause spinning movement of the rotor cap and hence the impeller in use.

In an example, a plurality of pre-swirl inlet vanes may be provided to a top cover of the housing to direct airflow towards the inlet. A pre-swirl cover may be provided to cover the pre-swirl vanes.

In an example, the bearing-housing structure may be coupled to a bottom cover of the housing via a snap feature or a screw arrangement.

In an example, the bearing-housing structure includes an annular disk that substantially aligns with or extends radially beyond the outer edge of the impeller to provide a shielding function. In an example, the bearing shaft and the disk include a split configuration in which the bearing shaft and the disk are separate components.

Another aspect of the present technology relates to a blower including a housing including an inlet and an outlet, a bearing-housing structure provided to the housing and adapted to rotatably support a rotor, a motor provided to the bearing-housing structure and adapted to drive the rotor, and an impeller provided to the rotor. The bearing-housing structure includes a housing part and a bearing cartridge provided to the housing part. The bearing cartridge includes a tubular sleeve and two spaced-apart bearings supported within the sleeve to support the rotor.

Another aspect of the present technology relates to a blower including a housing including an inlet and an outlet, a motor provided to the housing and adapted to drive a rotor, an impeller provided to the rotor, and an inlet cap provided to the inlet of the housing. The inlet cap is structured to occlude or block at least a central portion of the inlet.

Other examples, aspects, features, and/or advantages of this technology will become apparent from the following detailed description when taken in conjunction with the accompanying drawings, which are a part of this disclosure and which illustrate, by way of example, principles of the disclosed technology.

BRIEF DESCRIPTION OF THE DRAWINGS

The accompanying drawings facilitate an understanding of the various examples of this technology. In such drawings:

FIGS. 55 to 65 are cross-sectional views showing a snap feature to attach the bearing-housing structure to the bottom cover according to alternative examples of the present technology;

DETAILED DESCRIPTION OF ILLUSTRATED EXAMPLES

The following description is provided in relation to several examples (most of which are illustrated, some of which may not) which may share common characteristics and features. It is to be understood that one or more features of any one example may be combinable with one or more features of the other examples. In addition, any single feature or combination of features in any example or examples may constitute patentable subject matter.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

The subject headings used in the detailed description are included only for the ease of reference of the reader and should not be used to limit the subject matter found throughout the disclosure or the claims. The subject headings should not be used in construing the scope of the claims or the claim limitations.

PAP System

A PAP system (e.g., CPAP system) typically includes a PAP device (including a blower for generating air at positive pressure), an air delivery conduit (also referred to as a tube or tubing), and a patient interface. In use, the PAP device generates a supply of pressurized air (e.g., 2-30 cm $H_2O$) that is delivered to the patient interface via the air delivery conduit. The patient interface or mask may have suitable configurations as is known in the art, e.g., full-face mask, nasal mask, oro-nasal mask, mouth mask, nasal prongs, nasal cannula, etc. Also, headgear may be utilized to comfortably support the patient interface in a desired position on the patient's face.

Certain examples relate to PAP systems in which the PAP device or blower is adapted to be worn on the patient's head, is built into or incorporated into the patient interface or mask, is wearable or carried by the patient, is portable, is reduced in size or combinations thereof. In certain examples, the blower may be of the types described in International Application PCT/AU2010/001031, filed Aug. 11, 2010, entitled "Single Stage, Axial Symmetric Blower and Portable Ventilator," and/or International Application PCT/AU2010/001106, filed Aug. 27, 2010, entitled "PAP system," each of which is incorporated herein by reference in its entirety.

Figure 1:
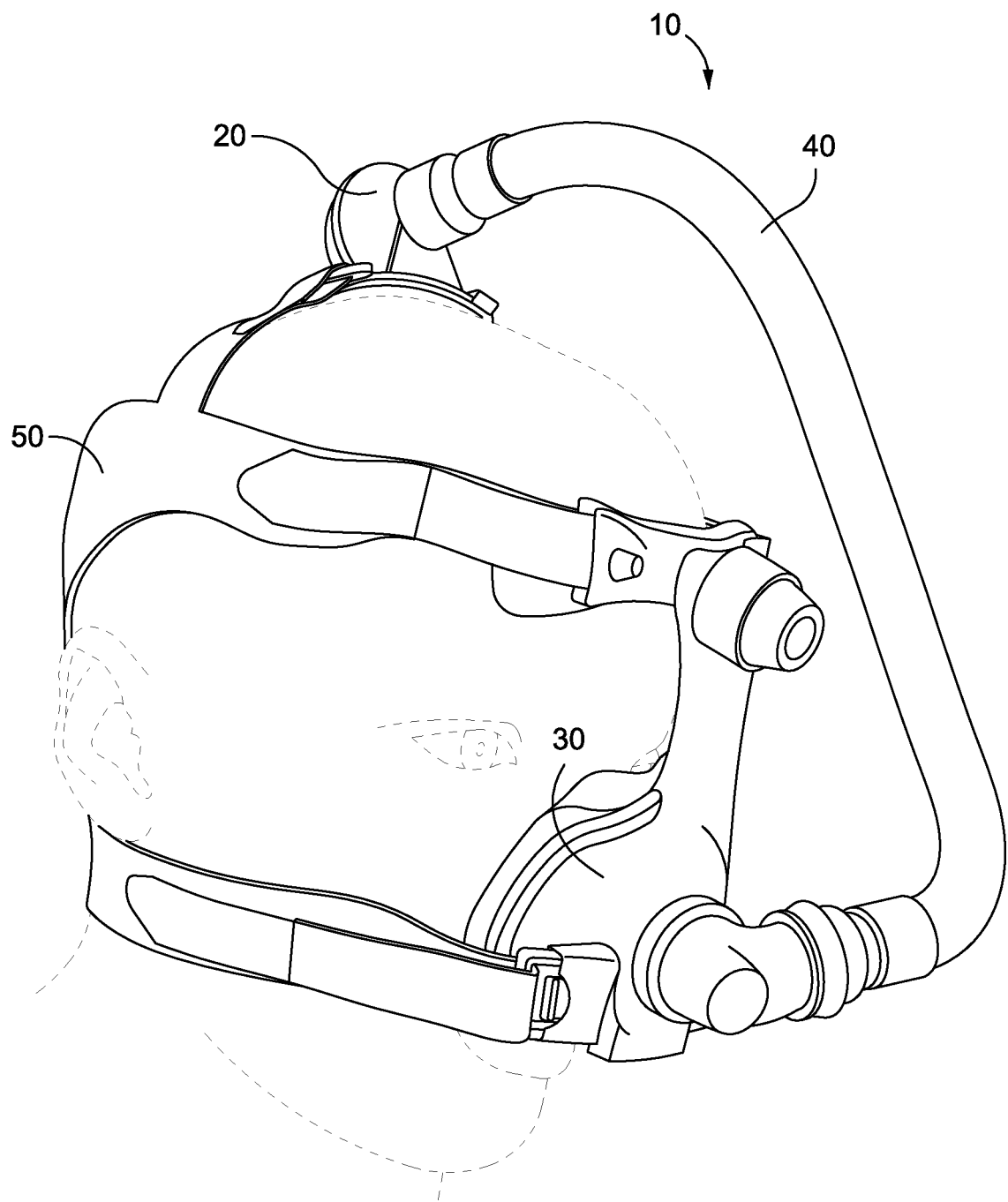
FIG. 1 is a perspective view of a headworn PAP system according to an example of the present technology on a model user's head.
Figure 2:
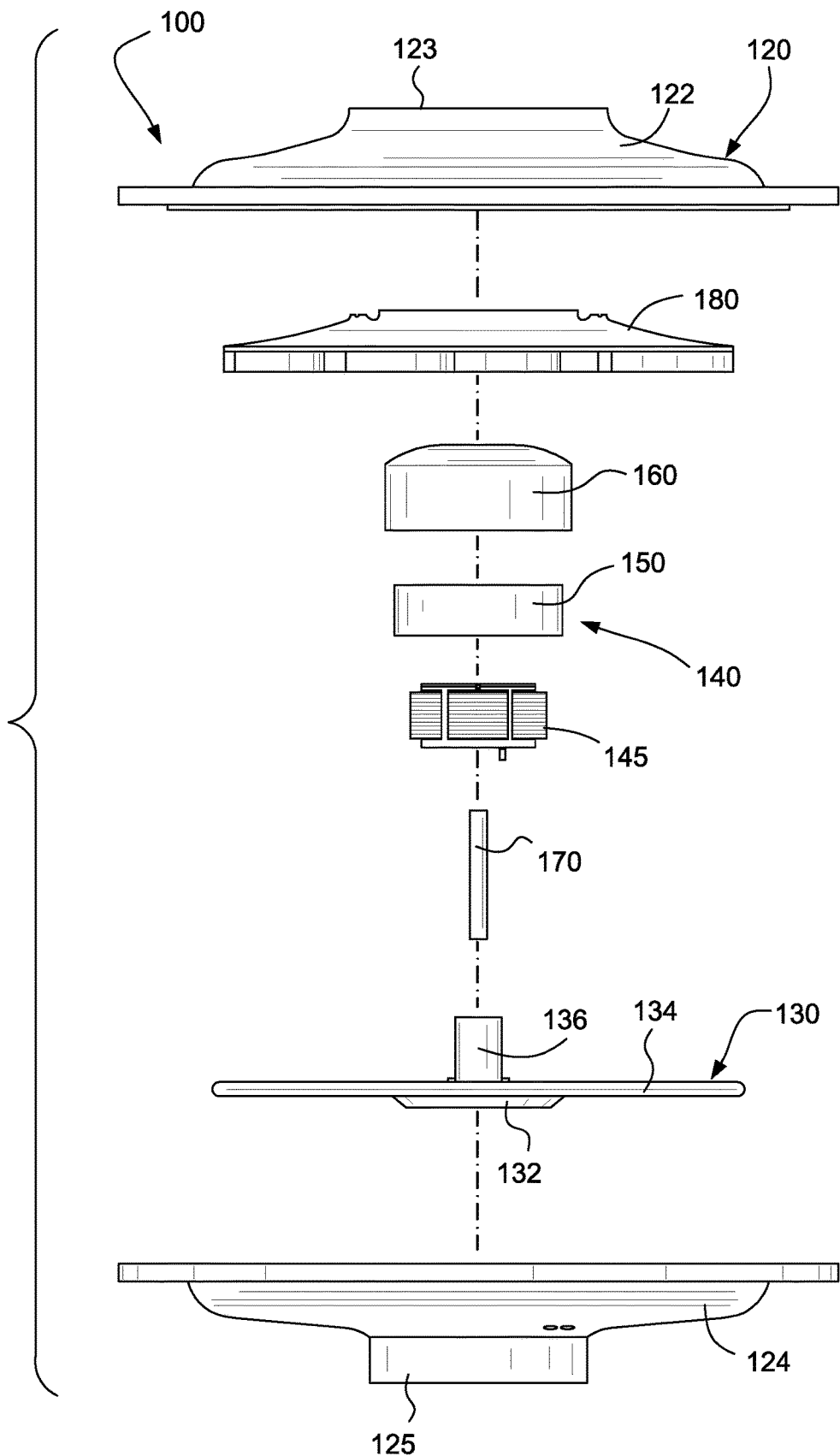
FIG. 2 is an exploded view of a blower according to an example of the present technology.

For example, FIG. 1 illustrates a headworn PAP system 10 including PAP device or blower 20, a patient interface or mask 30 (e.g., nasal mask), and an outlet tube 40 that interconnects the patient interface and the blower. Headgear 50 secures the blower and patient interface in position on the patient's head in use. However, the PAP system may be configured in other arrangements such as in or beside a pillow, in a scarf-like arrangement, incorporated into clothing, attached to a bed or bed head, etc., or in a more conventional PAP device configured to be located on a surface near a bedside similar to the ResMed™ S9™ CPAP system.

In certain examples, the PAP system may be used as a hygiene device to purify the incoming air. A filter may be present at the air inlet of the device to filter out particulate matter or impurities in the incoming air to deliver purified or filtered air to the user.

Blower

FIGS. 2 to 16 illustrate a single-stage blower 100 according to an example of the present technology (e.g., blower 100 may be provided as blower 20 in the PAP system of FIG. 1). The blower provides an arrangement that is very small in size, low cost, compact, lightweight, and provides ease of assembly, e.g., for use in a small wearable PAP system. In an example, the blower may be structured to provide pressurized air up to about 8 $cmH_2O$ (e.g., a maximum of up to about 4-8 $cmH_2O$, e.g., 4 $cmH_2O$, 5 $cmH_2O$, 6 $cmH_2O$, 7 $cmH_2O$, or 8 $cmH_2O$), which may be suitable for mild forms of sleep apnea or for treatment of snoring) and be run at a speed of approximately 15,000 rpm and flow approximately 60-70 L/min. In another example, the blower may be structured to provide pressurized air at higher pressures such as about 1-25 $cmH_2O$ and higher flows above 70 L/min such as up to approximately 90-120 L/min. In another example, the blower may include a multiple stage design, e.g., two or more impellers. In such a multiple stage design, the blower may be capable of providing higher levels of pressurized air of about 1-30 $cmH_2O$ and higher flow rates of up to approximately 140 L/min. However, a skilled addressee would understand that other motor speeds, pressures and flows may be used.

As illustrated, the blower 100 includes a housing or cover 120 with a top housing part or top cover 122 and a bottom housing part or bottom cover 124, a bearing-housing structure 130 (also referred to as a central bearing structure), a motor 140 (including a stator assembly or stator component 145, a magnet 150, and a rotor cup or cap 160) provided to the bearing-housing structure and adapted to drive a rotatable shaft or rotor 170, and an impeller 180 coupled to the rotor cap 160. The rotor cap 160 is coupled to an end portion of the rotor 170 and together with the magnet 150 may be referred to as the rotor assembly. In this arrangement, the motor has an outer rotor configuration to rotate the impeller 180. This arrangement also allows the motor components to at least be partially nested within the impeller providing a lower profile blower.

Figure 99:
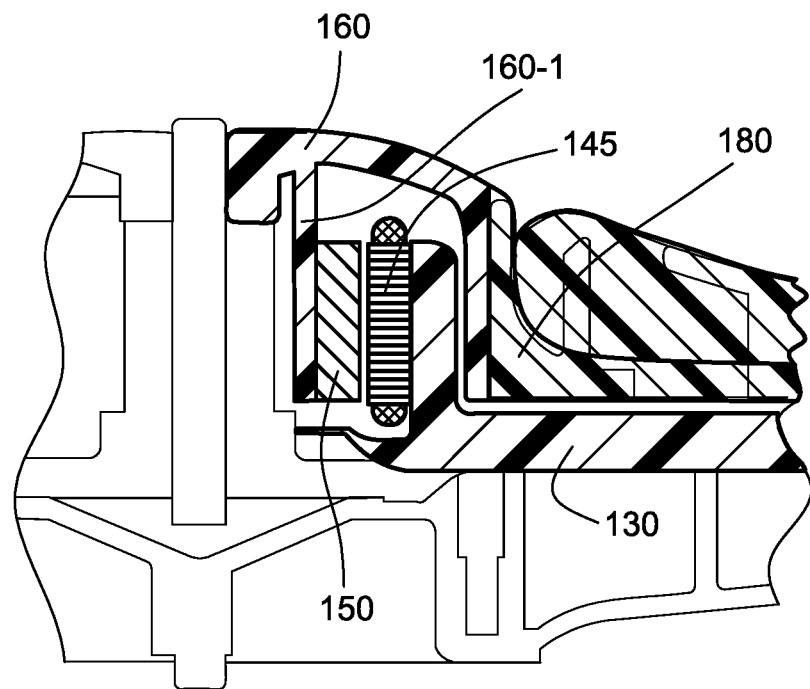
FIG. 99 is a cross-sectional view of a blower including an internal rotor configuration according to an example of the present technology.
Figure 100:
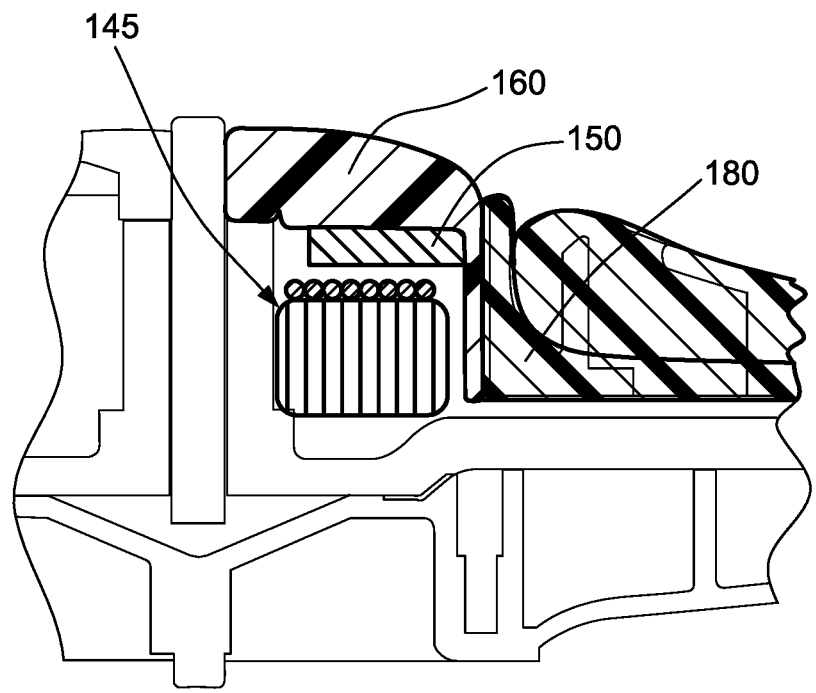
FIG. 100 is a cross-sectional view of a blower including an axial configuration according to an example of the present technology.

In an alternative arrangement, not shown, the motor may include an inner rotor configuration wherein the magnet 150 may be coupled to the rotor 170 and impeller 180 is coupled to an end portion of the shaft or rotor 170. In such an arrangement, the impeller may be located above or around the motor components. FIG. 99 illustrates an internal rotor configuration in which the rotor cap 160 includes an inner wall 160-1 to support the magnet 150 within the stator component 145 supported by the bearing-housing structure 130. The impeller 180 is coupled to the rotor cap 160 so it extends above or around the motor components. In a further alternative arrangement, as shown in FIG. 100, the motor may include an axial gap motor wherein the stator component 145 (including stator and windings), magnet 150 and rotor cap 160 have a stacked or pancake configuration. However, it is to be understood that the motor may have any arrangement suitable to drive rotation using an electromagnetic interaction.

Motor Assembly

Figure 3:
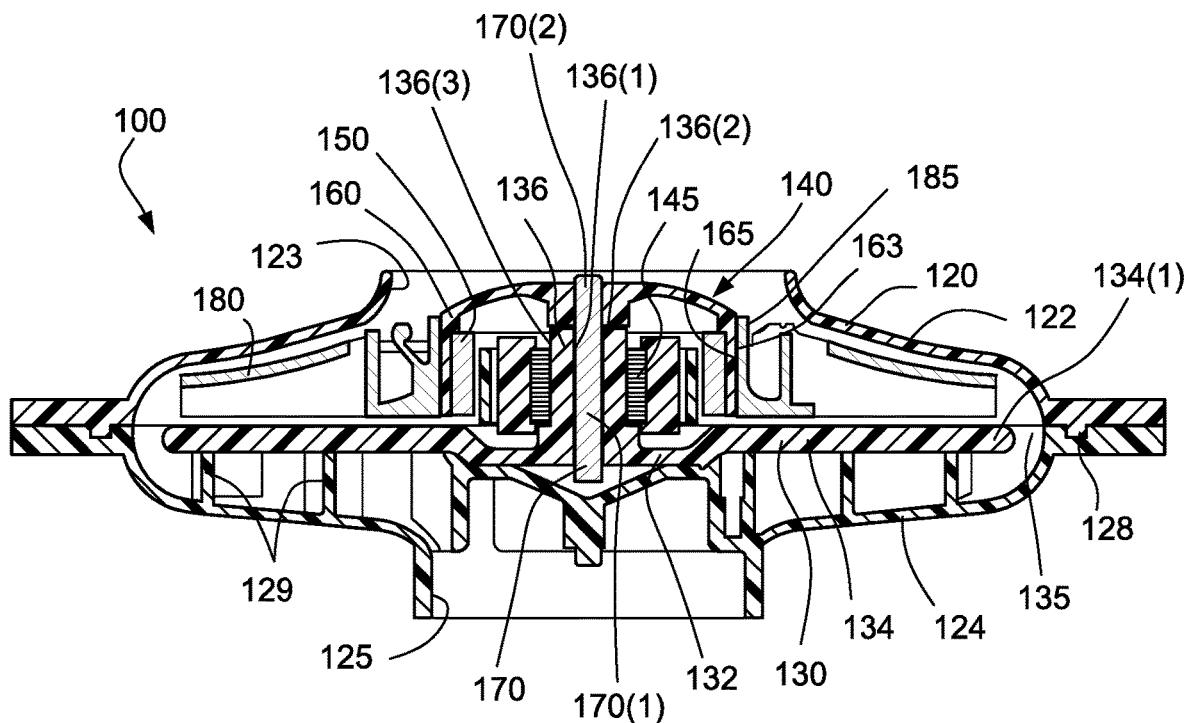
FIG. 3 is a cross-sectional view of the blower of FIG. 2.
Figure 4:
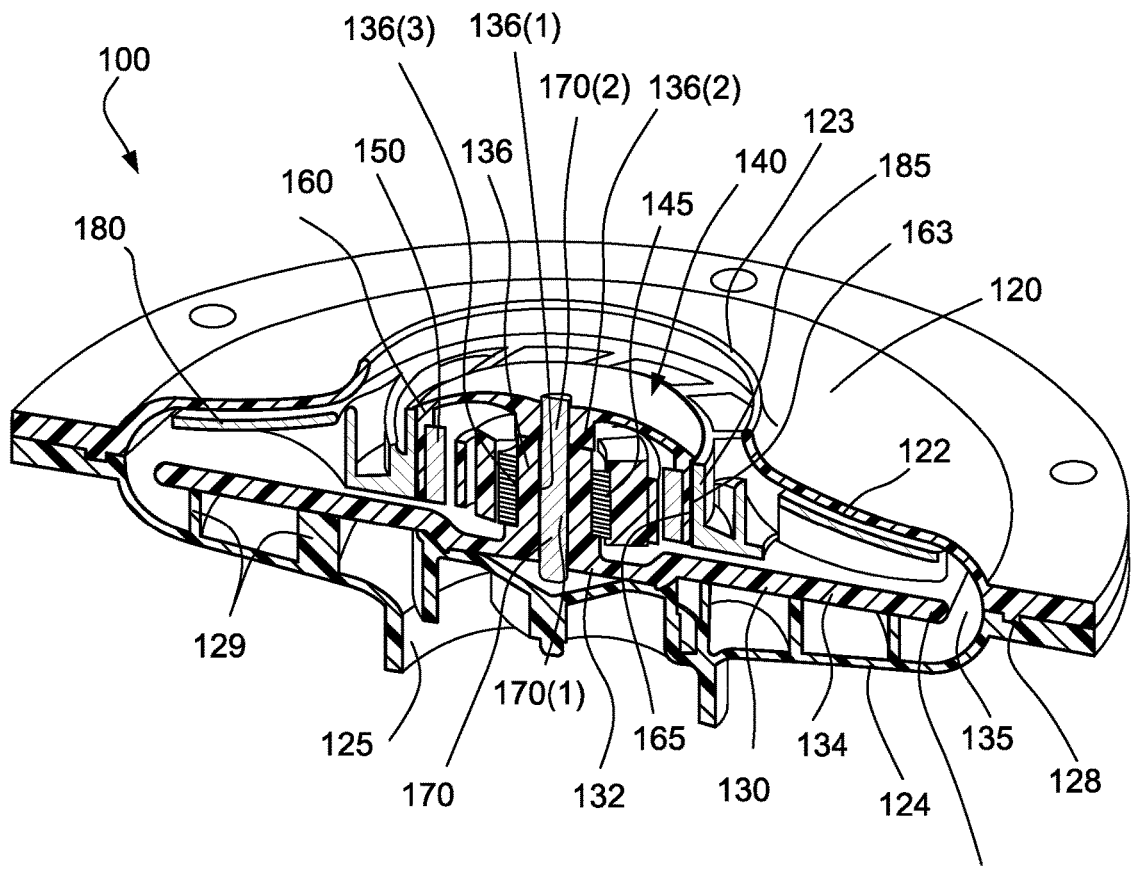
FIG. 4 is an isometric cross-sectional view of the blower of FIG. 2.
Figure 5:
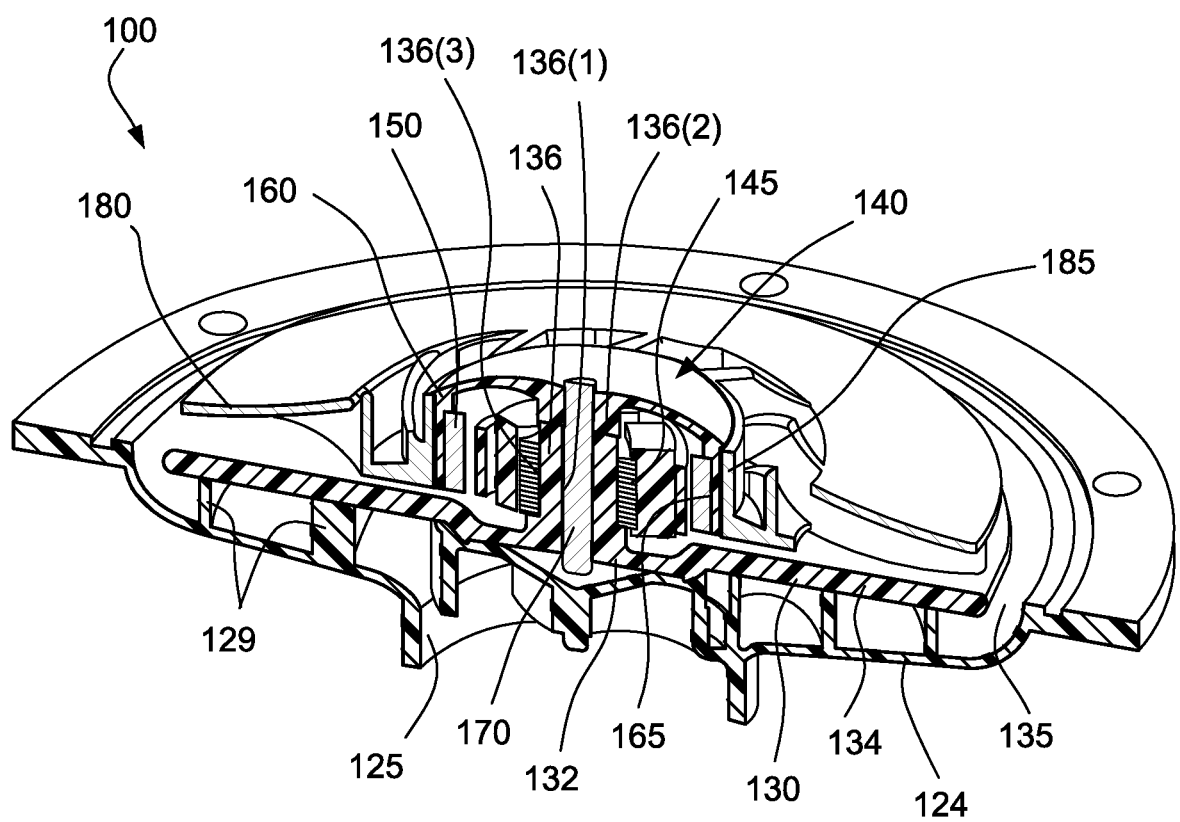
FIG. 5 is an isometric cross-sectional view like FIG. 4, but without the top cover.
Figure 6:
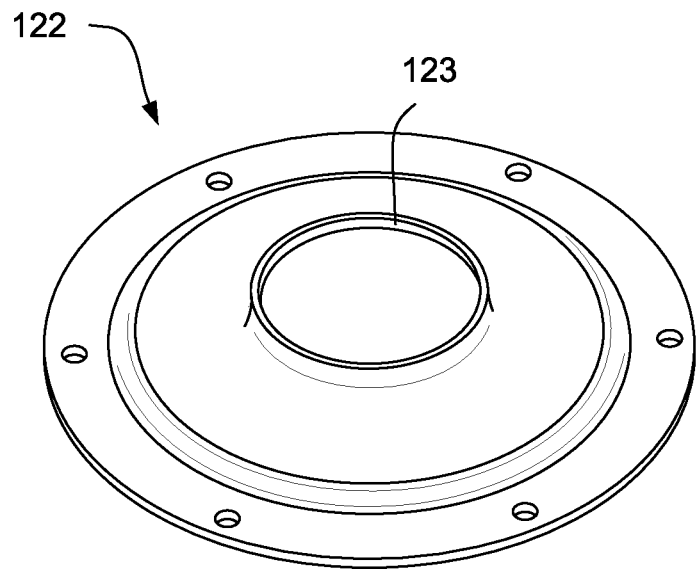
FIG. 6 is a perspective view of a top cover of the blower of FIG. 2.
Figure 7:
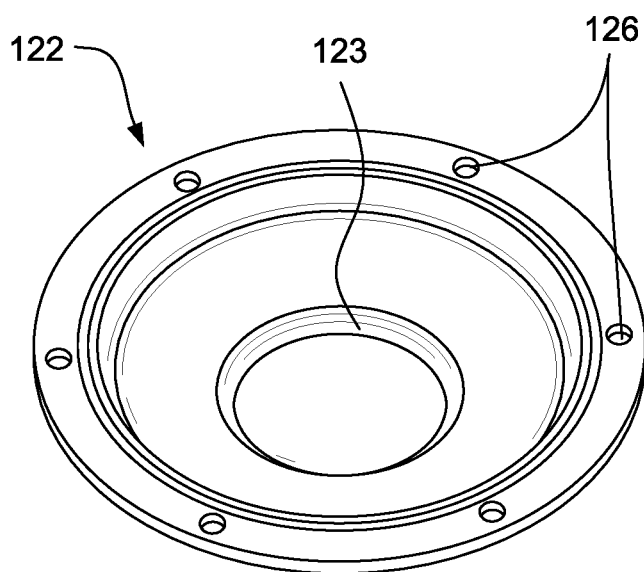
FIG. 7 is a reverse perspective view of the top cover of FIG. 6.

FIGS. 3-5 illustrate the assembled motor 140 within the blower 100. The motor is structured such that the bearing-housing structure 130 provides a support for the other components of the motor as well as providing the bearing function to facilitate rotation of the rotor assembly. In the illustrated example, one end portion 170(1) of the rotor 170 (e.g., metal or plastic) is rotatably supported within the bearing shaft 136 of the bearing-housing structure 130 and the other end portion 170(2) of the rotor 170 is inserted freely into the rotor cap 160, i.e., rotor not fastened to motor. The rotor cap 160 includes an opening 162 to receive the rotor 170 (e.g., see FIGS. 12 and 13). However, rotor retention designs may be incorporated into certain examples to retain the rotor and/or rotor assembly within the motor especially when the motor is not in use as described in more detail below.

The hub 185 of the impeller 180 is provided along the exterior surface 163 of the rotor cap 160, and the magnet 150 is provided along the interior surface 165 of the rotor cap 160, for example by frictional engagement or by the use of an adhesive. The interior surface 165 may provide a recess or groove 165(1) to receive the magnet 150 (e.g., see FIG. 13).

Figure 108:
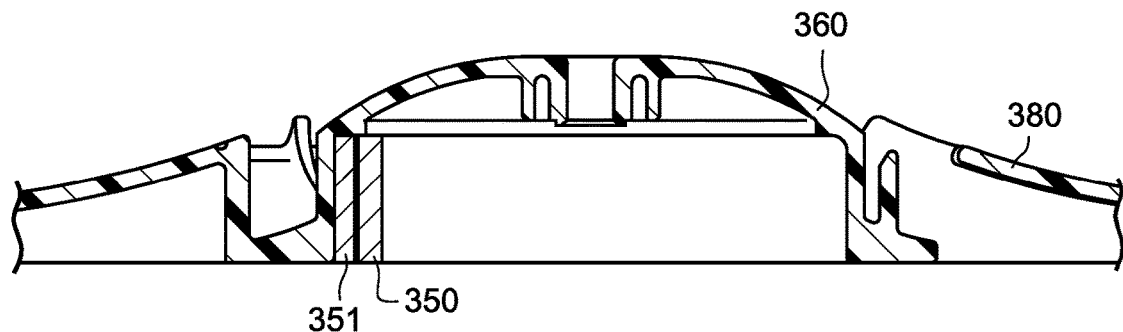
FIG. 108 is a cross-sectional view of a rotor cap and impeller integrally formed as a one-piece structure according to an example of the present technology.

In an alternative example, as shown in FIG. 108, the rotor cap and the impeller may be integrally formed as a one-piece structure, e.g., rotor cap and impeller molded in one piece from a plastic material, e.g., Lexan®, polycarbonate (e.g., glass reinforced polycarbonate), Polyether ether ketone (PEEK) or other suitable materials. As illustrated, the one-piece structure includes a rotor cap portion 360 and an impeller portion 380. A metal sleeve 351 and a magnet 350 are provided along the interior surface of the rotor cap portion 360. The sleeve 351 provides a magnetic return or flux path between the poles of the magnet 350. Another example of a one-piece rotor cap and impeller is described in U.S. Pat. No. 7,804,213, which is incorporated herein by reference in its entirety.

In a further alternative example (not shown), the impeller may be overmolded onto the rotor cap. A diamond neural or other surface finish may be provided on the surface of the rotor cap to facilitate the fixturing or attachment of the overmolded impeller.

The magnet 150 is coupled to the interior surface of the rotor cap 160 and is located to facilitate magnetic interaction with the stator assembly to drive the motor. The magnet may be made from any permanent magnet material such as a bonded NdFeB ring, a ferrite material, samarium cobalt or other such magnetic material. In certain examples, the magnet may be centered on the stator assembly. In another example, the magnet 150 may be off-set from the stator assembly to magnetically preload a thrust bearing portion of the bearing-housing structure 130. In this arrangement, a pre-load spring may be not required for the bearing. Off-setting the magnet 150 may also assist with retaining the rotor assembly within the motor.

The stator assembly 145 is coupled to the bearing-housing structure 130 to retain the stator assembly 145 in position. The stator assembly 145 may be coupled to the bearing-housing structure 130 by a snap-fit, over-molding, adhesively bonded, or other fastening means. The stator assembly or stator component 145 is provided along the exterior surface 136(3) of the bearing shaft 136 of the bearing-housing structure 130. In use, the stator assembly 145 acts on the magnet 150 which causes spinning movement of the rotor cap 160 and hence the impeller 180. This arrangement at least partially "nests" the motor (stator assembly, fixed magnet and rotor cap) within the impeller to reduce the size of the blower. In an example, components of the motor are at least partially within a common (horizontal) plane.

Figure 17:
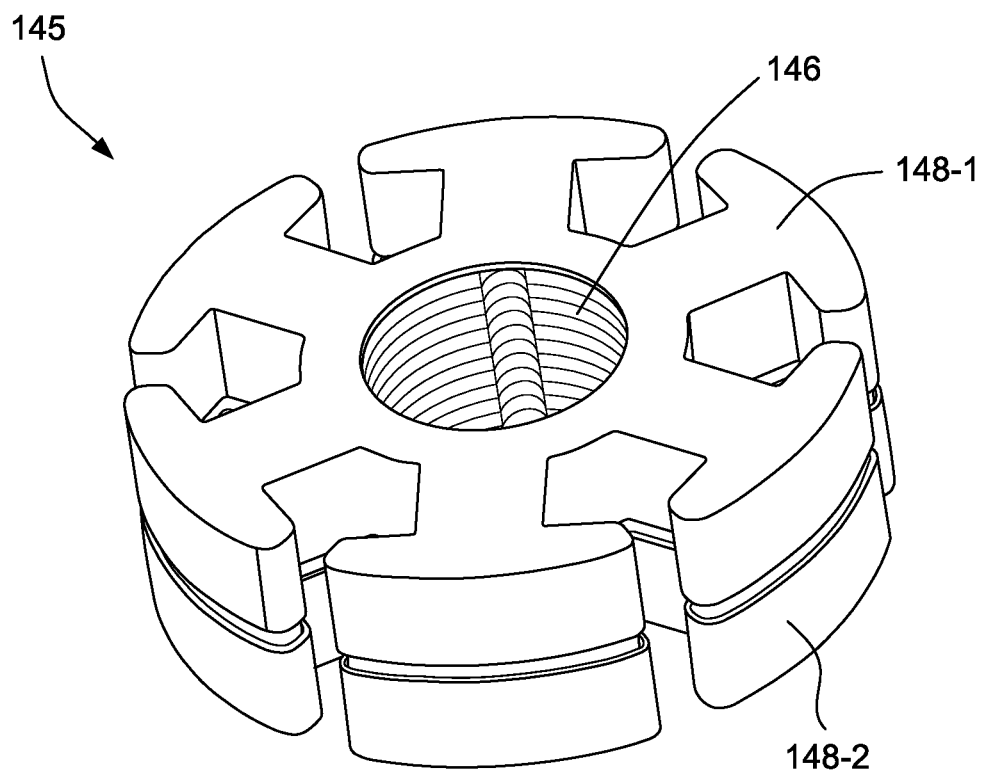
FIG. 17 is a perspective view of a stator core and slotliners according to an example of the present technology.
Figure 18:
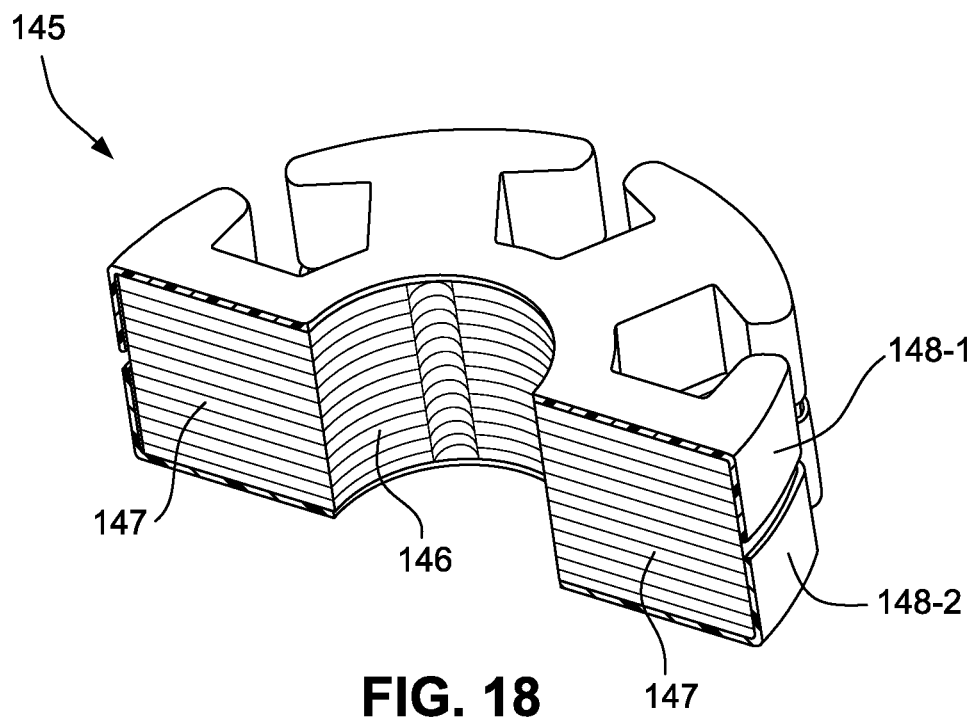
FIG. 18 is a cross-section view of the stator core and slotliners of FIG. 17.

As shown in FIGS. 17 and 18, the stator assembly 145 includes a stator core 146 having a plurality of stator teeth 147, e.g., six stator teeth, on which stator coils or windings are wound. In the illustrated example, the stator core 146 includes a plurality of laminations, e.g. 2-100 laminations or more, that are stacked on top of one another. The laminations may be affixed to one another using adhesives or other techniques. The number of laminations may depend upon the power requirements of the motor. Alternatively, the stator core may have a different arrangement such as a solid member rather than a stack of laminations.

The stator assembly 145 may also include a pair of slotliners, e.g., first and second slotliners 148-1 and 148-2 as shown in FIGS. 17 and 18, structured to insulate the stator core 146 from the stator coils or windings. First and second slotliners 148-1 and 148-2 may be provided to opposite sides of the stator core 146 prior to winding the stator coils onto the stator core. The thickness of the slotliners may be controlled to facilitate the packing of more stator coil or winding into the stator. However, in an alternative arrangement, the stator core may be coated with a material, for example, by powder coating the stator core. In certain examples, the slotliners may include those described in the applicants pending U.S. patent application publication number US-2009-0324435, published Dec. 31, 2009, and entitled "Insulator for Stator Assembly of Brushless DC Motor," which is incorporated herein by reference in its entirety.

The stator coils or winding comprise magnet wire or motor wire such as copper wire, for example. In an example, the stator assembly may comprise three motor wires for a 3 phase motor, e.g., 2 coils per phase, 45 turns per coil, however other coil arrangements are possible. The different wires for each phase may each be identified by using a different color for each of the motor wires. The motor wires may be directly interfaced to a PCB coupled to the blower for ease of assembly. Further, the center tap and lead wires may be bonded to the housing to minimize loose motor wire entering into the air path. In an example arrangement, the motor wires may be routed through the stator vanes to a PCB assembly or driver as described below. The motor wires may be routed together and twisted for ease of wire egress. However, the motor wires may be routed out separately. The motor wire is wound onto the stator core.

Rotor Retention

Figure 19:
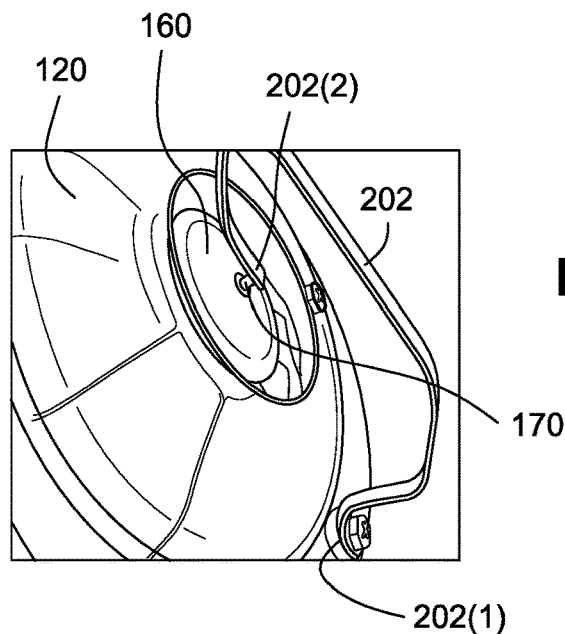
FIG. 19 is a perspective view of a blower including a over-top retention arm according to an example of the present technology.

In certain examples, one or more rotor retention designs or structures may be included to assist in retaining the rotor and/or rotor assembly within the motor especially when the motor is not in use. For example, one or more over-top rotor retention arms may be attached to the top cover and over the rotor assembly to prevent vertical movement of the rotor assembly. FIG. 19 shows an example an over-top retention arm 202 having one end 202(1) attached to the top cover 120, e.g., by a fastener, and the opposite end 202(2) positioned over the rotor assembly (i.e., rotor cap 160, magnet 150, and rotor 170).

Figure 20:
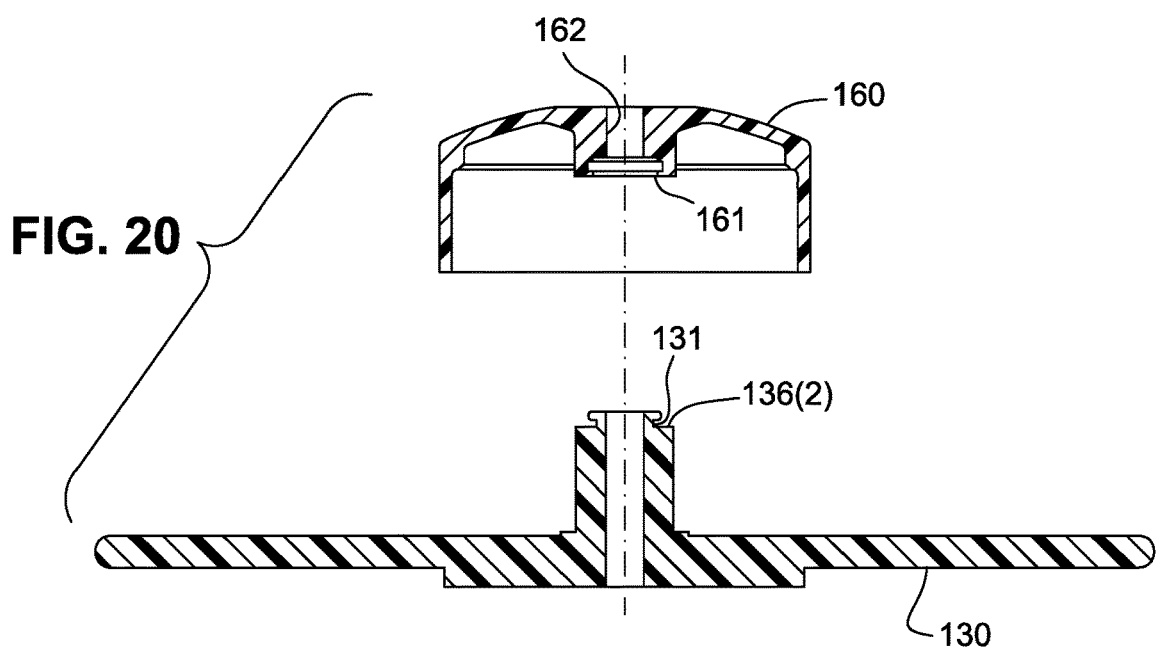
FIG. 20 is an exploded view of a rotor cap and bearing-housing structure including mating features according to an example of the present technology.
Figure 21:
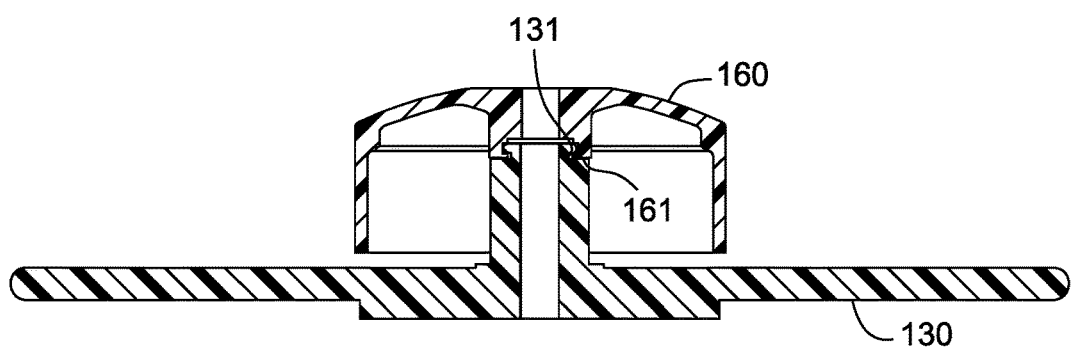
FIG. 21 is a cross-sectional view of the rotor cap and bearing-housing structure of FIG. 20.

In another rotor retention example, the bearing-housing structure 130 may be coupled or interlocked to a mating feature in the rotor cap 160. For example, as shown in FIGS. 20 and 21, the bearing-housing structure 130 may comprise a slot or groove 131 on the thrust bearing surface 136(2) configured to receive a lip or ridge 161 present on the mating feature of the rotor cap 160. The lip or ridge 161 on the rotor cap 160 may snap-fit into the slot or groove 131 on the thrust bearing surface 136(2). The mating feature may be incorporated at the lower surface surrounding the aperture 162 of the rotor cap 160. The snap-fit design may also include radii, fillet and/or chamfers to assist with the connection. The ridge or lip may be provided around the entire circumference of the mating feature of the rotor cap 160 or may be limited to a plurality of discrete snaps, beads, or protrusions at locations around the mating surface, such as 2-10 snaps or protrusions or more.

Figure 22:
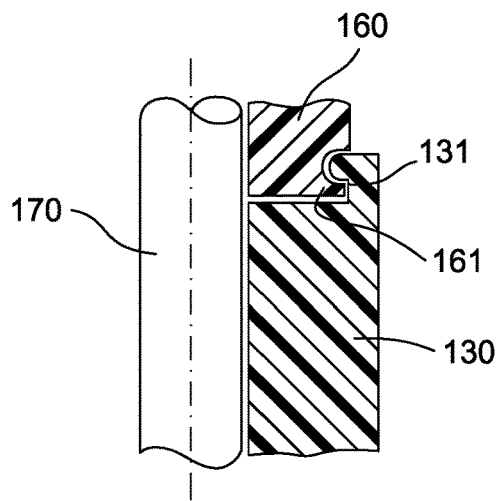
FIG. 22 is a cross-sectional view of a rotor cap and bearing-housing structure including mating features according to another example of the present technology.
Figure 23:
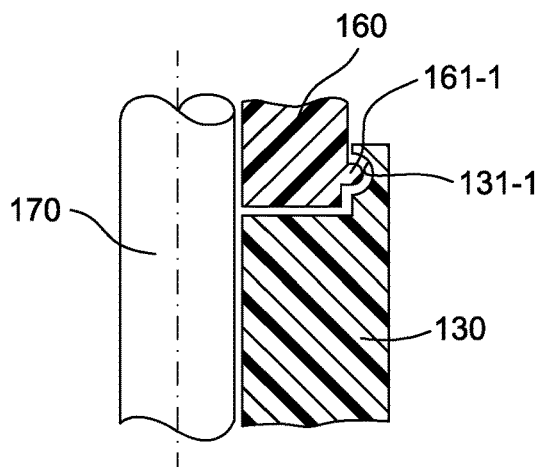
FIG. 23 is a cross-sectional view of a rotor cap and bearing-housing structure including mating features according to another example of the present technology.
Figure 24:
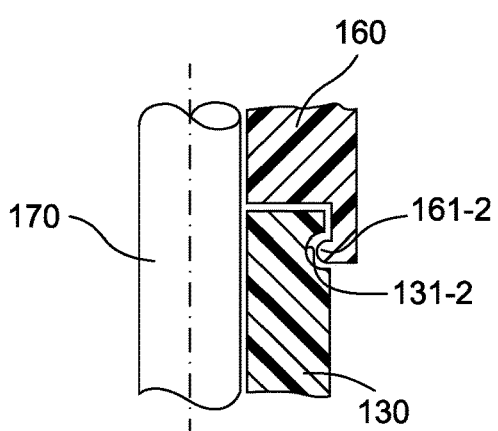
FIG. 24 is a cross-sectional view of a rotor cap and bearing-housing structure including mating features according to another example of the present technology.
Figure 25:
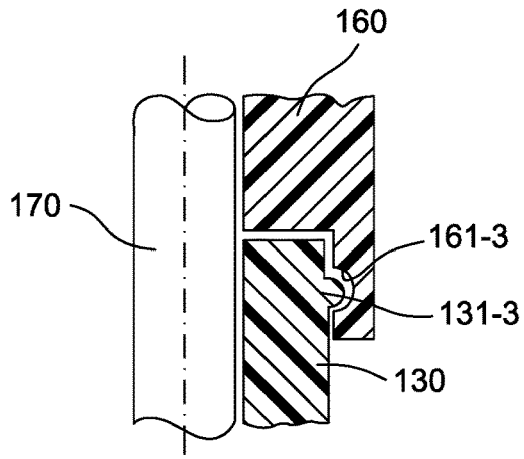
FIG. 25 is a cross-sectional view of a rotor cap and bearing-housing structure including mating features according to another example of the present technology.
Figure 26:
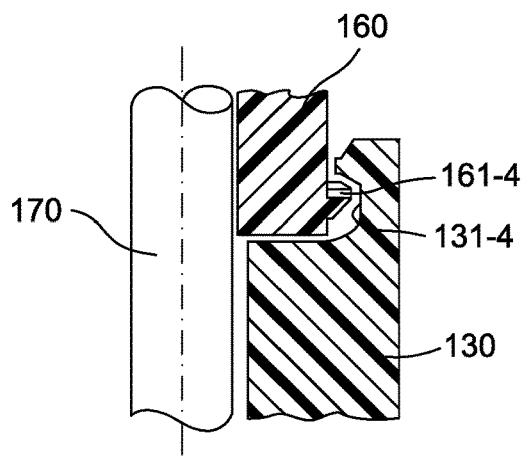
FIG. 26 is a cross-sectional view of a rotor cap and bearing-housing structure including mating features according to another example of the present technology.
Figure 27:
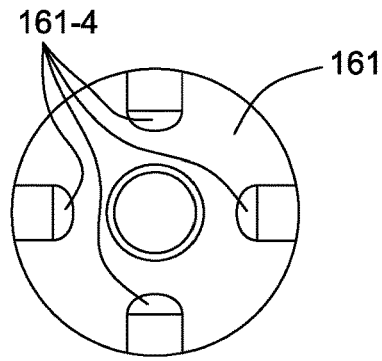
FIG. 27 is a plan view of the rotor cap of FIG. 26.

FIGS. 22-27 show alternative examples of mating features to couple the rotor cap to the bearing housing structure. FIG. 22 is similar to the arrangement of FIGS. 20 and 21 in which the rotor cap 160 includes a lip or ridge 161 to engage within a slot or groove 131 provided to the bearing-housing structure 130. In FIG. 23, the rotor cap includes a bead 161-1 adapted to engage within a groove 131-1 provided to the bearing-housing structure 130. In FIGS. 22 and 23, the mating features engage along an inwardly facing surface of the bearing-housing structure, i.e., surface facing the rotor. FIGS. 24 and 25 show arrangements in which the mating features engage along an outwardly facing surface of the bearing-housing structure, i.e., surface facing away from the rotor. For example, FIG. 24 shows a rotor cap including a bead 161-2 adapted to engage within a groove 131-2 provided to the bearing-housing structure 130, and FIG. 25 shows a rotor cap including a recess 161-3 adapted to engage with a bead 131-3 provided to the bearing-housing structure 130. FIGS. 26 and 27 show an arrangement in which the rotor cap 160 includes a plurality of discrete beads 161-4 (e.g., 4 beads) adapted to engage within a groove 131-4 provided to the bearing-housing structure 130.

Figure 28:
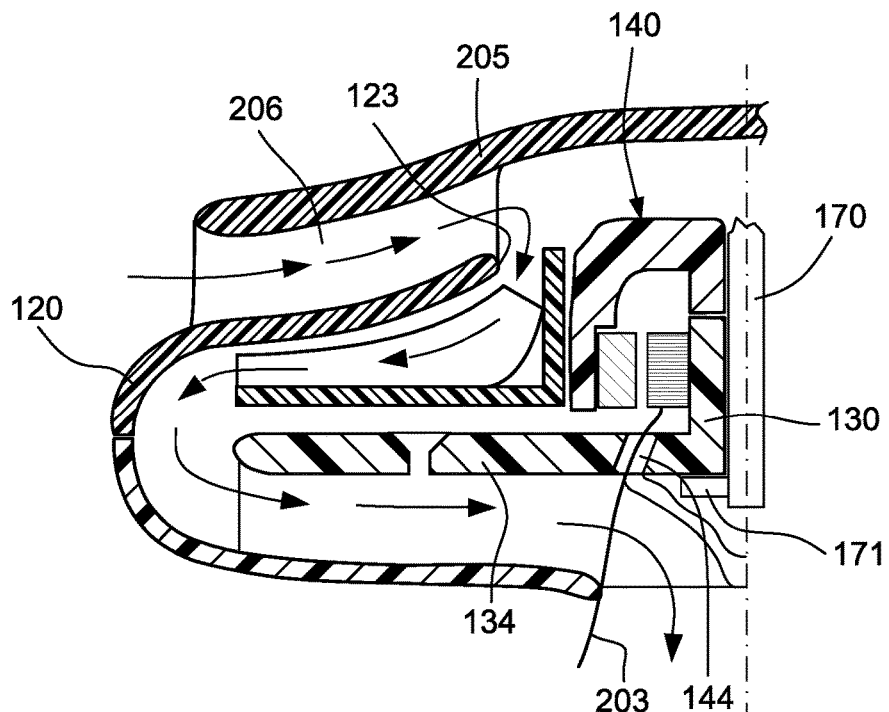
FIG. 28 is a cross-sectional view of a blower including a rotor with a retention flange according to an example of the present technology.

FIG. 28 shows another rotor retention example in which a lower flange, ridge or projection 171 is coupled to the bottom of the rotor or shaft 170 (e.g., constructed of stainless steel and press-fit to rotor) that is positioned underneath the bearing-housing structure 130. The lower flange 171 prevents the rotor 170 from lifting vertically out of the motor assembly 140. The lower flange may also provide an additional or alternative rotating surface for the rotor 170.

Figure 29:
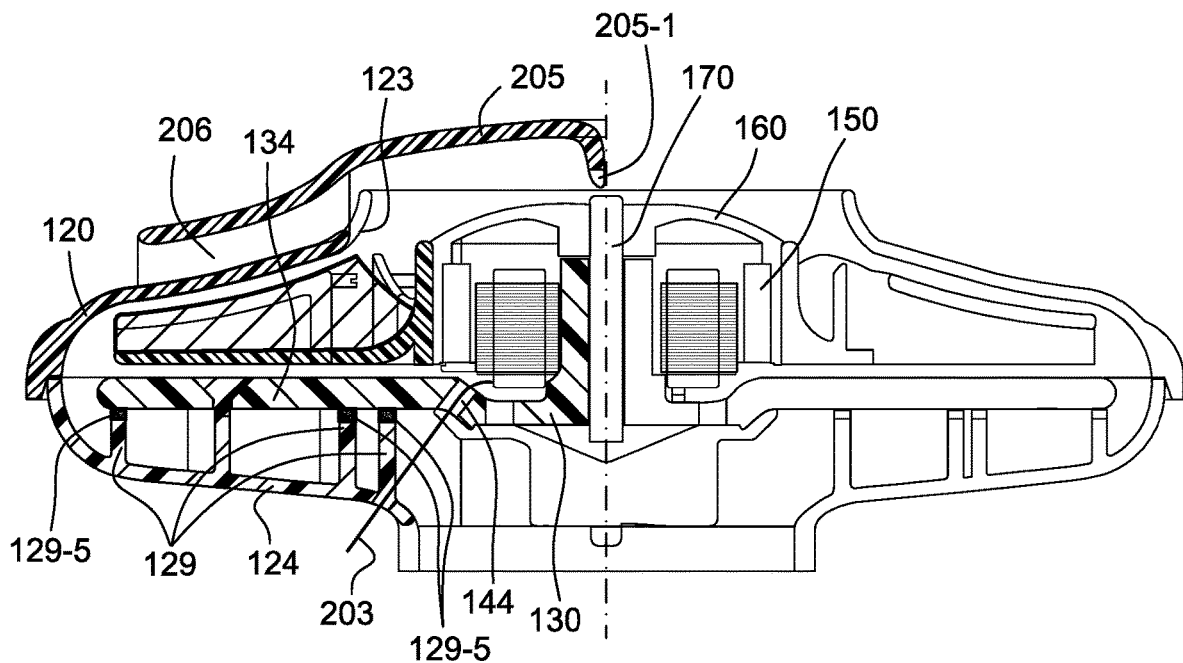
FIG. 29 is a cross-sectional view of a blower including a pre-swirl cover according to an example of the present technology.

In certain examples including a pre-swirl cover as shown in FIG. 29, as described in more detail below, the pre-swirl cover 205 may further include an axial shock bumper or stop 205-1 to prevent the rotor assembly (i.e., rotor cap 160, magnet 150, and rotor 170) or rotor 170 from separating from the motor assembly in the case of a shock. For example, the bumper or stop 205-1 may prevent the rotor assembly from lifting off the bearing-housing structure's thrust bearing surface if the blower is dropped or bumped, especially when not in use. The bumper or stop is arranged above the rotor 170 in a manner that prevents the rotor and/or rotor assembly from lifting up and out of the motor assembly. The bumper or stop may include a ball, such as a steel ball, a flat surface or any other means that would maintain the rotor and rotor assembly in the correct position within the motor.

Figure 30:
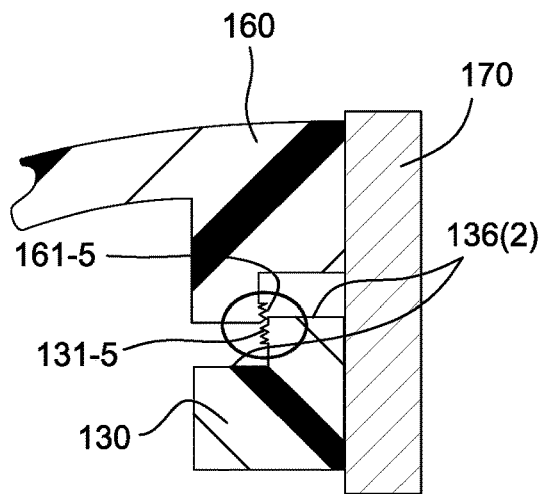
FIGS. 30 to 32 are cross-sectional views showing a screw thread arrangement to couple the rotor cap to the bearing-housing structure according to an example of the present technology.
Figure 31:
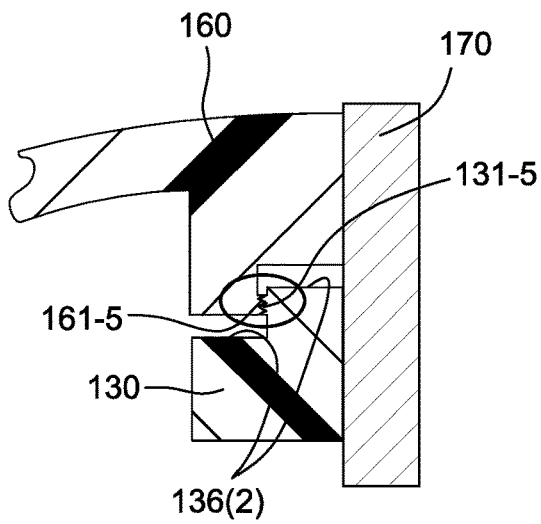
Figure 32:
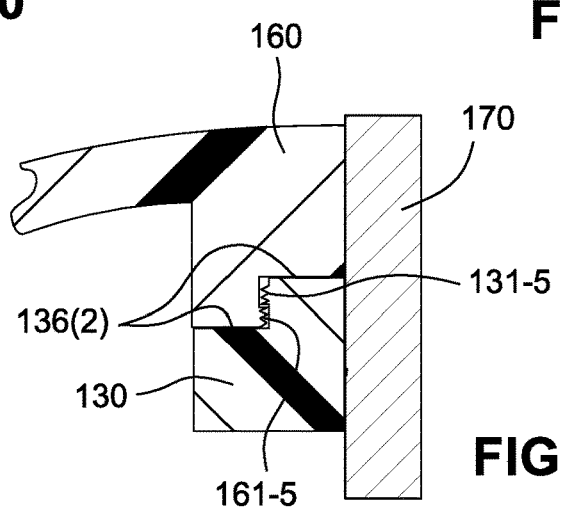

In another rotor retention example, as shown in FIGS. 30 to 32, complimentary screw threads 161-5, 131-5 may be incorporated on the rotor cap 160 and the bearing thrust surface 136(2) of the bearing-housing structure 130, respectively. In such a design, the rotor assembly (i.e., rotor cap 160, magnet 150, and rotor 170) must be screwed over the screw thread and fully engaged with the bearing thrust surface 136(2) of the bearing-housing structure 130 before the rotor assembly may freely rotate. The screw threads would be configured in the same direction in which the rotor rotated to prevent the release or uncoupling of the rotor assembly in use. The rotor assembly may be removed by rotating or unscrewing the rotor assembly in the opposite direction to normal rotation. FIG. 30 shows the rotor assembly and bearing-housing structure before engagement, FIG. 31 shows the rotor assembly and bearing-housing structure partially engaged, and FIG. 32 shows the rotor assembly and bearing-housing structure fully engaged.

Blower Housing

The top cover 122 provides an inlet 123 at one end of the blower and the bottom cover 124 provides an outlet 125 at the other end of the blower. The blower is operable to draw a supply of gas into the housing through the inlet and provide a pressurized flow of gas at the outlet. The blower has axial symmetry with both the inlet and outlet aligned with an axis of the blower. In use, gas enters the blower axially at one end and leaves the blower axially at the other end.

In another example, the blower may include an axial aligned inlet and an outlet that is tangential to the inlet.

The top and bottom covers (e.g., constructed of a plastic material) may be attached to one another by fasteners, e.g., plurality of openings 126 provided along flange-like perimeter of covers 122, 124 to allow fasteners to extend therethrough. In addition, the top and bottom covers may provide a joint 128 (e.g., tongue and groove arrangement as shown in FIGS. 3 and 4) along its perimeter to facilitate alignment and connection. However, it should be appreciated that the covers may be attached to one another in other suitable manners, e.g., ultrasonic weld.

Figure 8:
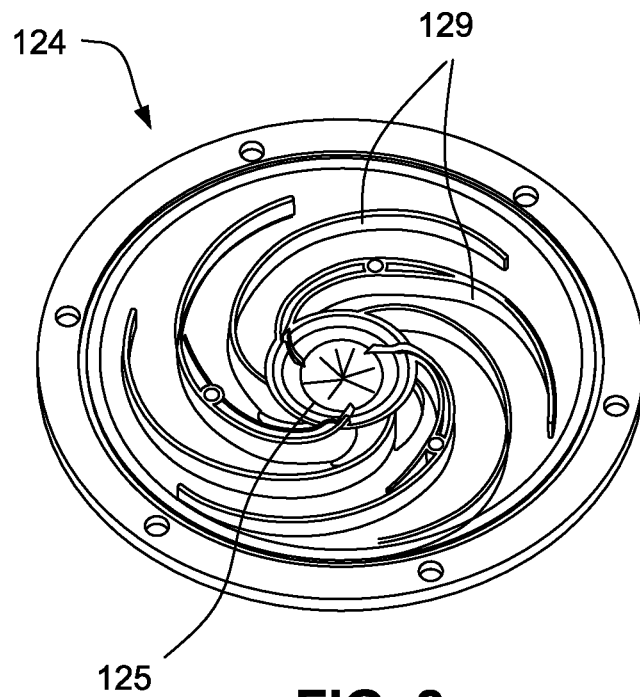
FIG. 8 is a perspective view of a bottom cover of the blower of FIG. 2.
Figure 9:
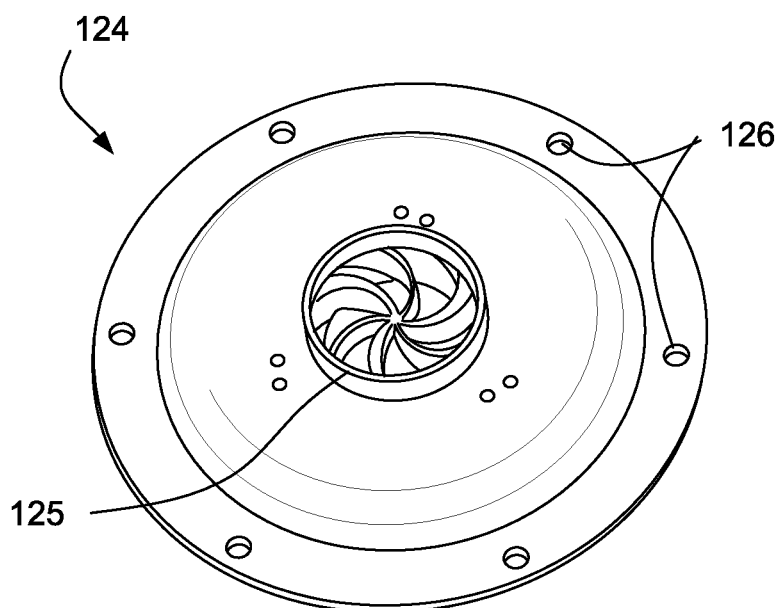
FIG. 9 is a reverse perspective view of the bottom cover of FIG. 8.

As shown in FIGS. 8 and 9, the bottom cover 124 includes a plurality of stator vanes or de-swirling vanes 129, e.g., between about 2 and 50 stator vanes or about 15-30 or about 5-15, to direct airflow towards the outlet 125, e.g., also referred to as flow straighteners. In the illustrated example, the bottom cover has 6 stator vanes. Each vane is substantially identical and has a generally spiral shape. In the illustrated example, the leading edge of each vane extends generally tangential to flow so as to collect air exiting the impeller and direct it from a generally tangential direction to a generally radial direction. In the illustrated example, the stator vanes support the bearing-housing structure 130 within the cover.

Figure 33:
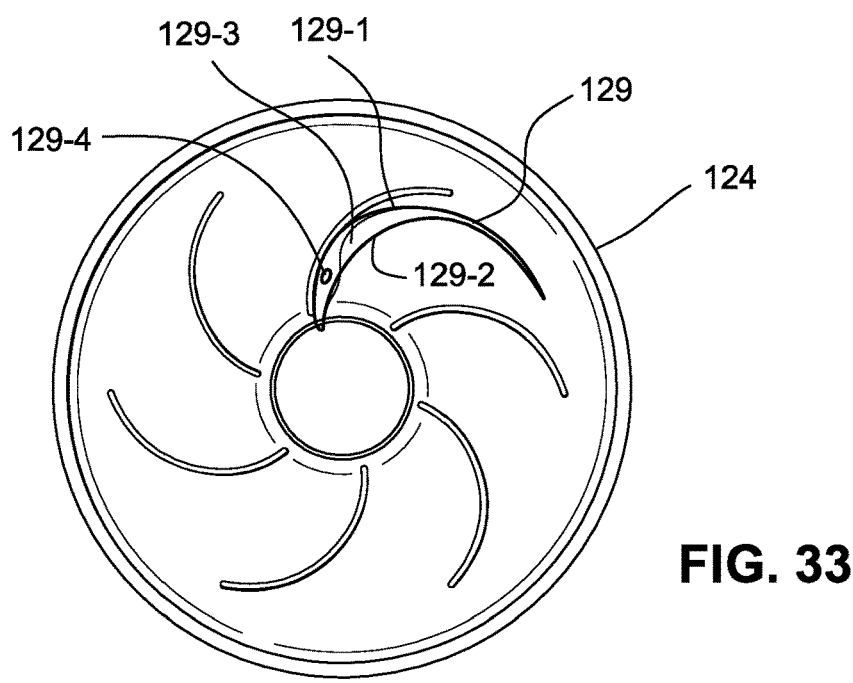
FIGS. 33 to 35 show various views of a bottom cover with de-swirling vanes according to an example of the present technology.
Figure 34:
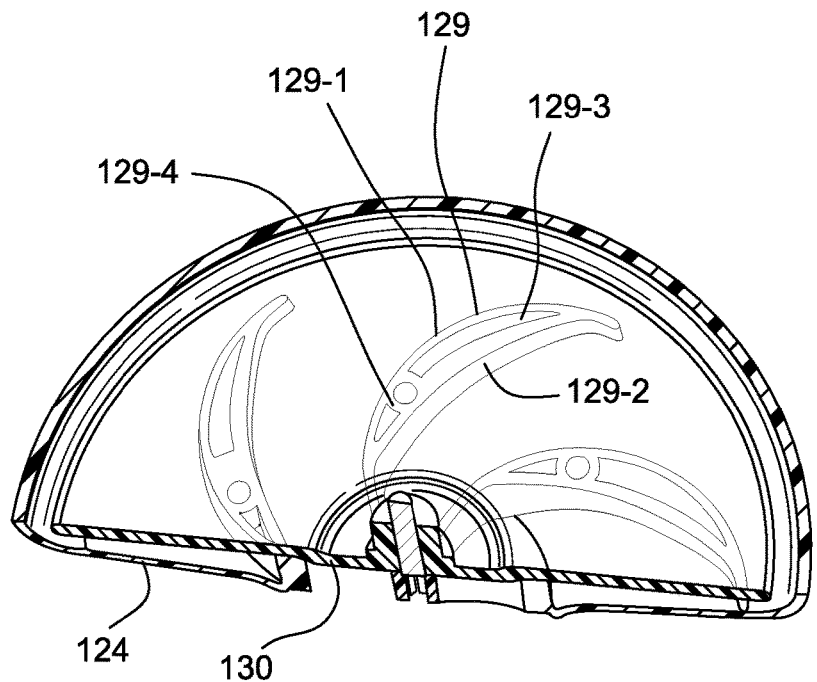
Figure 35:
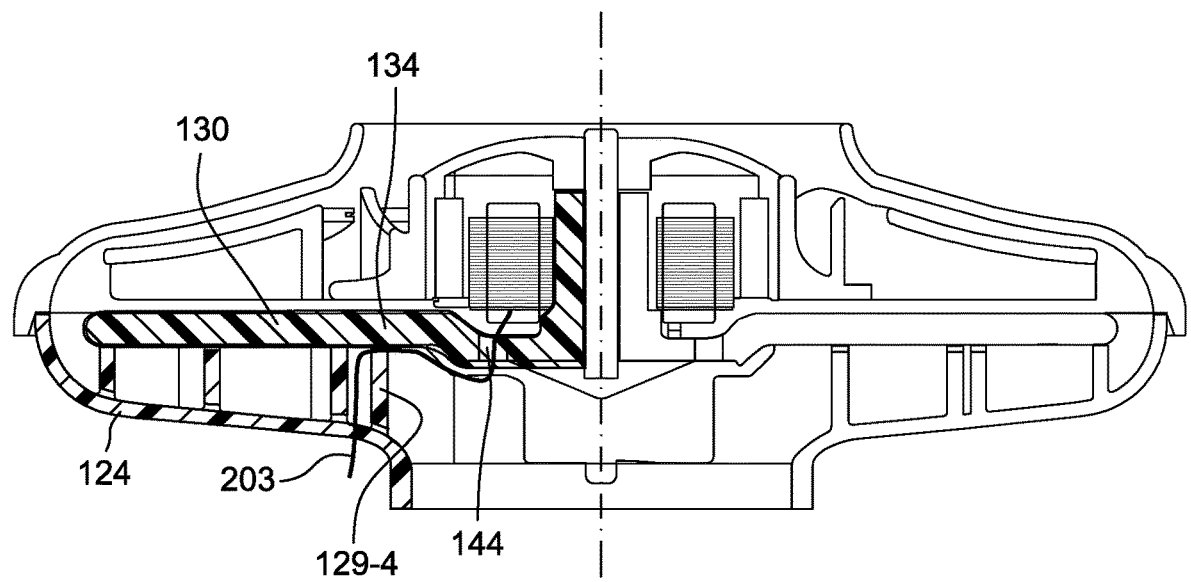
Figure 36:
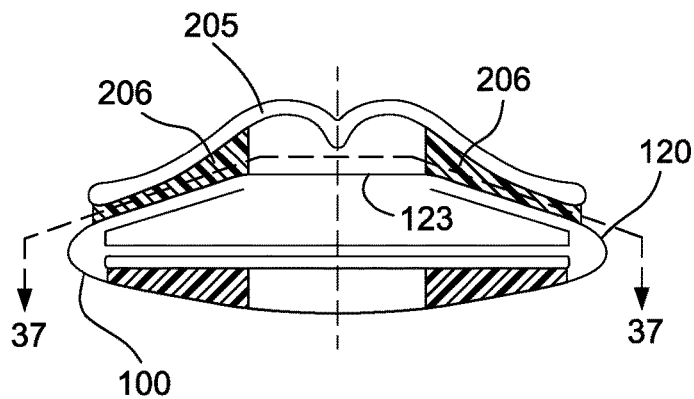
FIGS. 36 to 38 show various views of a blower with pre-swirl inlet vanes and a pre-swirl cover according to an example of the present technology.
Figure 37:
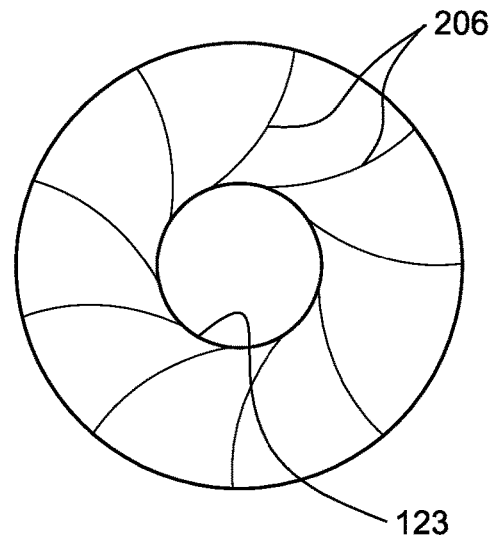

In certain examples, one or more of the de-swirling vanes 129 may be structured as dual vanes that provide a passage to allow for the motor wires to be routed through the vanes and out to the PCB or driver. For example, FIGS. 33 to 35 show exemplary deswirling vanes 129 each including spaced apart side walls or dual vanes 129-1, 129-2 that provide a space 129-3 therebetween. A cylindrical guide 129-4 is provided within the space that allows motor wires 203 (e.g., see FIG. 35) to be routed through the vane. FIG. 33 shows an example of a dual vane arrangement in relation to a single vane arrangement. FIG. 8 shows an example in which three of the deswirling vanes 129 include a dual vane configuration that provide passage for motor wires. In another example, only one or two of the deswirling vanes may include a dual vane structure for routing all motor wires.

Figure 101:
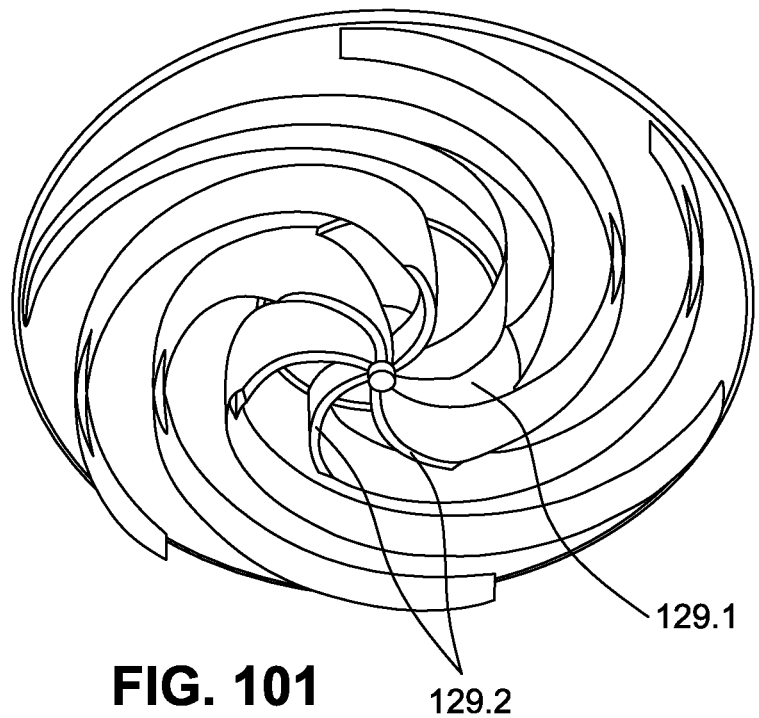
FIGS. 101 and 102 are various views of a bottom cover including de-swirling vanes according to an example of the present technology.
Figure 102:
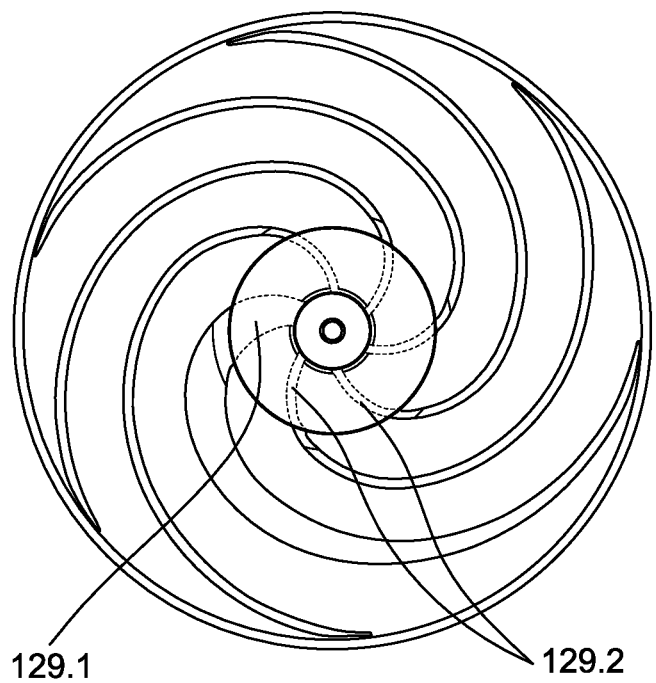

FIGS. 101 and 102 illustrate another example of a deswirling vane arrangement for the bottom cover. In this example, the vanes include different thicknesses. For example, one of the vanes 129.1 is relatively thick while the remaining vanes 129.2 (e.g., remaining 5 vanes) are relatively thin with respect to the vane 129.1. However, it should be appreciated that the thickness arrangement may have other suitable arrangements, e.g., same number of thick/thin vanes, more thin than thick vanes, more thick than thin vanes, all vanes have different thicknesses, etc.

Figure 103:
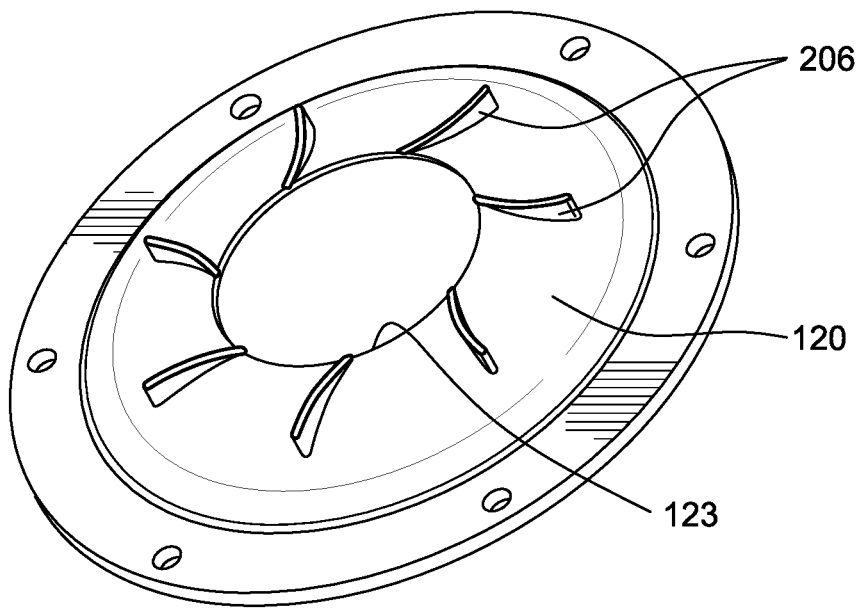
FIGS. 103 and 104 are various views of a top cover with pre-swirl vanes according to an example of the present technology.
Figure 104:
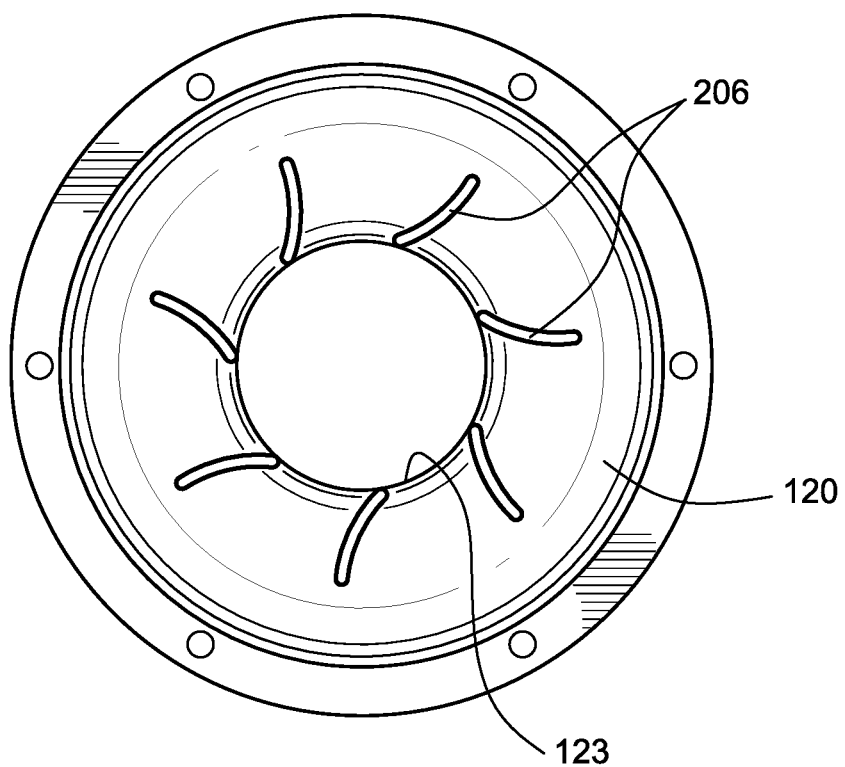

In certain examples, as shown in FIGS. 28, 29 and 36 to 38, the blower may also include a plurality of pre-swirl inlet vanes 206 located above the inlet 123 and above or on the top cover 120. The plurality of inlet vanes 206, e.g., between about 2 and 50 inlet vanes or about 15-30 or about 5-15, such as 5, 6, 7, 8, 9, 10, or 11 vanes, are structured to direct airflow towards the inlet 123. Each inlet vane 206 is substantially identical and has a curved profile (e.g., see FIG. 37) to direct the airflow towards the inlet 123. The inlet vanes are structured to pre-swirl the incoming air to facilitate a reduction in shock losses at the leading edge of the impeller blades. The inlet vanes may also assist in reducing the radiated noise from the inlet 123. The inlet vanes may further assist in increasing the efficiency of the blower. In certain examples, the pre-swirl vanes are coupled to the outer surface of the top cover 120. The pre-swirl vanes may be integrally molded into the top cover 120 or attached via gluing, ultrasonic welding, snap fit, adhesive or some other fastening means. FIGS. 103 and 104 show an example of pre-swirl vanes 206 integrally molded or otherwise attached to the top cover 120.

Figure 38:
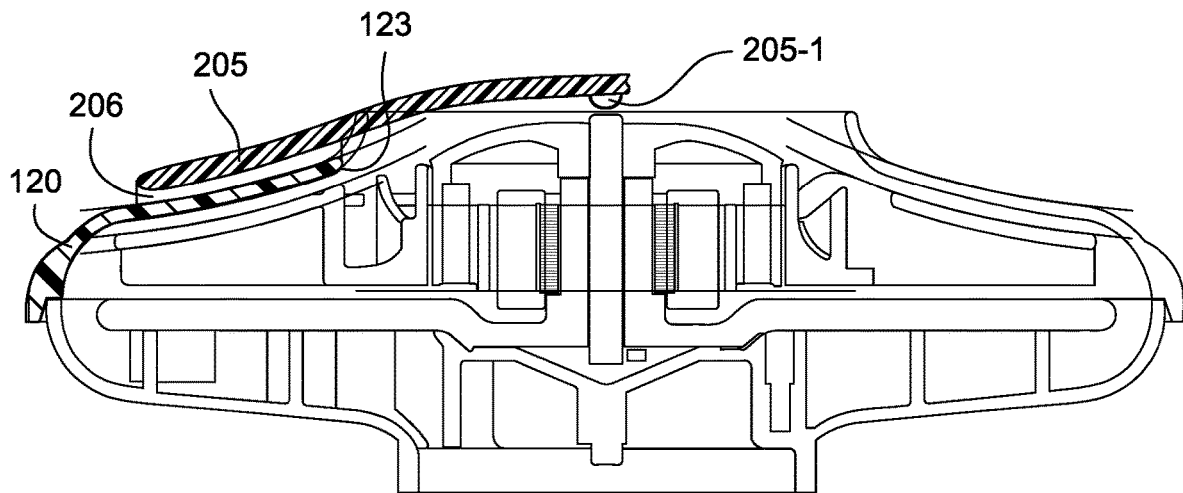
Figure 105:
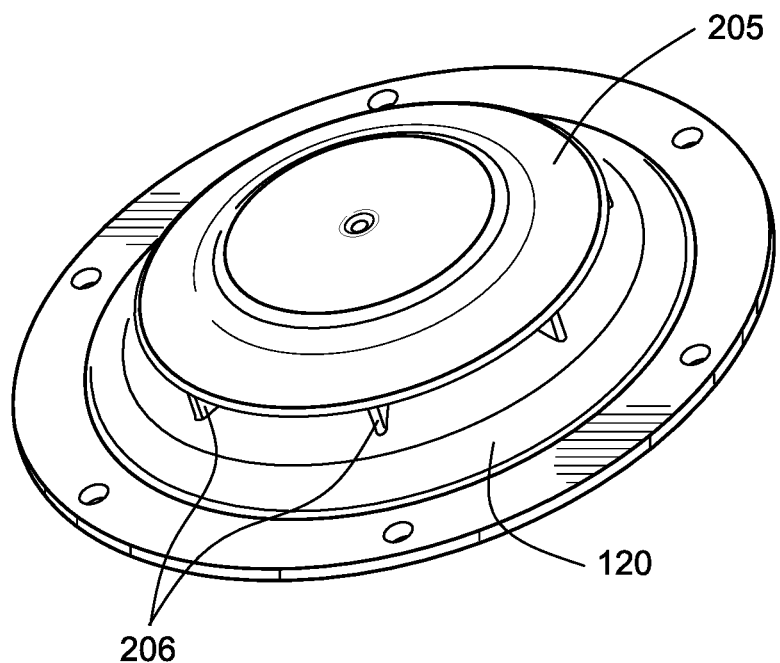
FIGS. 105 to 107 are various views of a top cover with pre-swirl vanes and a pre-swirl cover according to an example of the present technology.
Figure 106:
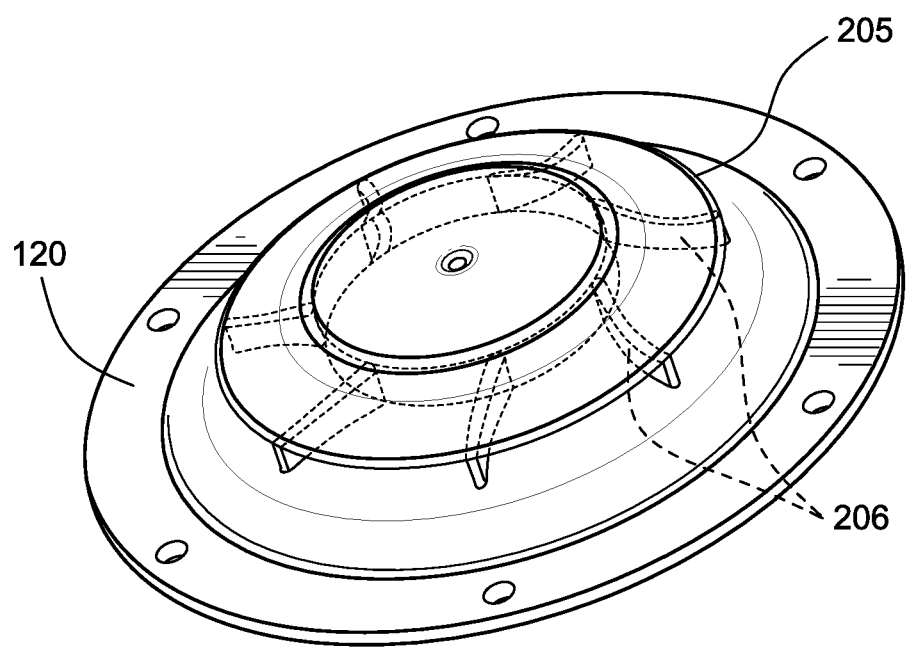
Figure 107:
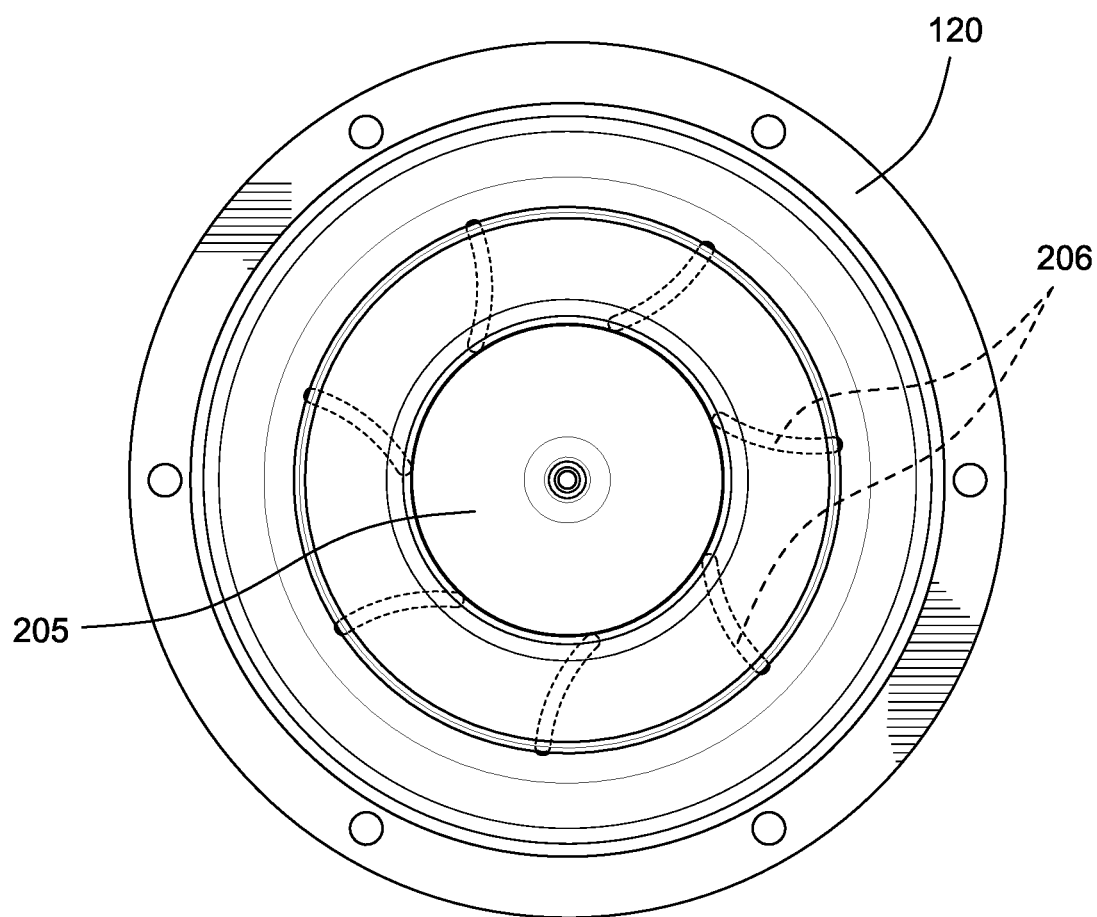

As shown in FIGS. 28, 29, and 36 to 38, the pre-swirl vanes 206 are covered by a pre-swirl cover 205 structured to cover the pre-swirl vanes and form a plurality channels to direct the air flow towards the inlet 123. The pre-swirl cover is coupled to the top edge of the pre-swirl vanes on the top cover 120, e.g., by heat staking, ultrasonic welding, gluing, adhesive or other such fastening means. FIGS. 105 to 107 show the top cover 120 and vanes 206 of FIGS. 103 and 104 with a pre-swirl cover 205 coupled to the vanes. The pre-swirl cover may be made from a plastic material, metal, aluminum or other suitable materials, for example the pre-swirl cover may be molded from a plastic material or formed by metal injection molding. The pre-swirl cover may be molded from or over-molded with a low durometer material such as a silicone or urethane, to provide a dampening function. In an alternative example, the pre-swirl vanes 206 may be integrally molded with the pre-swirl cover 205 and the top cover 120 is coupled to the bottom edge of the pre-swirl vanes 206. FIG. 38 also shows a bumper or stop 205-1 on the pre-swirl cover 205, as described above in relation to FIG. 29.

Inlet Cap

In an example, an inlet cap may be provided to the inlet, e.g., to reduce noise. The inlet cap may be integrally formed in one-piece with the top cover. Alternatively, the inlet cap may be formed separately from the top cover and attached or otherwise provided to the inlet of the top cover. In an example, the inlet cap may be structured to support or otherwise retain a filter to filter the incoming air.

For example, FIGS. 116 to 119 show a blower 300 including an inlet cap 310 provided to the inlet 323 of the top cover 322 according to an example of the present technology. The remaining components of the blower are similar to that shown in FIGS. 109-110, which is described in greater detail below, e.g., blower includes a bearing-housing structure 330 structured to support a bearing cartridge 390 adapted to rotatably support the rotor 370.

As illustrated, the inlet cap 310 includes a generally disk-shaped inner portion 312, a generally ring-shaped outer portion 314, and radially extending spokes or connectors 316 that interconnect the inner and outer portions 312, 314. The outer portion 314 of the inlet cap 310 engages the annular side wall 322(1) of the top cover 322 defining the inlet 323 to support the inlet cap 310 at the inlet 323. The outer portion 314 overhangs the side wall 322(1) to secure the inlet cap in position and align the inlet cap with the axis of the inlet. In an example, the inlet cap may engage the side wall with a press or friction fit, however, it should be appreciated that the inlet cap may be secured to the side wall in other suitable manners, e.g., adhesive, mechanical interlock (e.g., snap-fit), ultrasonic welding, etc.

In use, the inner portion 312 is positioned to occlude or block a central portion of the inlet 323 and a supply of gas is drawn into the housing through the annular gaps 315 defined between the outer edge of the inner portion 312 and the inner edge of the outer portion 314. In an example, the cross-sectional area provided by the gaps 315 (i.e., inlet area) is greater than about 150 mm$^2$, e.g., about 150-300 mm$^2$, 175-225 mm$^2$, 200-250 mm$^2$, 250-300 mm$^2$. Such arrangement reduces noise, e.g., by reducing radiated noise from the inlet by reducing the effective inlet area, by reducing the Helmholtz resonance frequency.

In the illustrated example, the inner portion 312 includes a diameter that is less than a diameter of the rotor cap 360, e.g., diameter of inner portion 312 less than about 20 mm, e.g., 18 mm. However, it should be appreciated that in other examples the inner portion may include a diameter that is similar to or greater than a diameter of the rotor cap.

Figure 124:
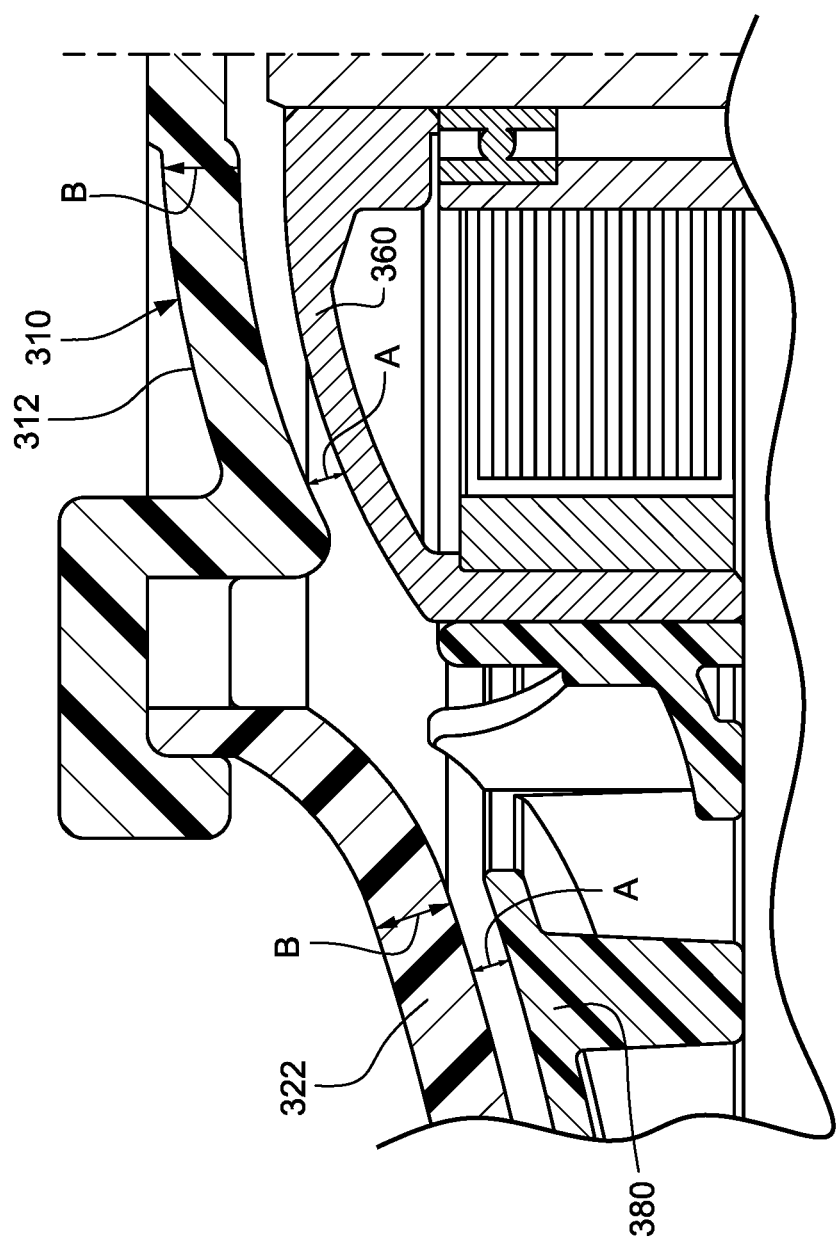
FIG. 124 is another cross-sectional view of the blower shown in FIGS. 116 to 119.
Figure 125:
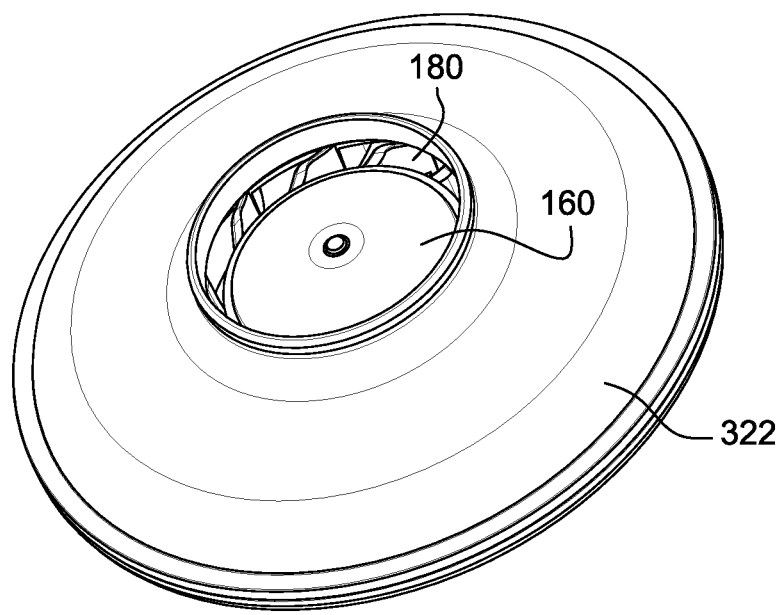
FIGS. 125 to 127 show alternative views of the blower of FIG. 109.
Figure 126:
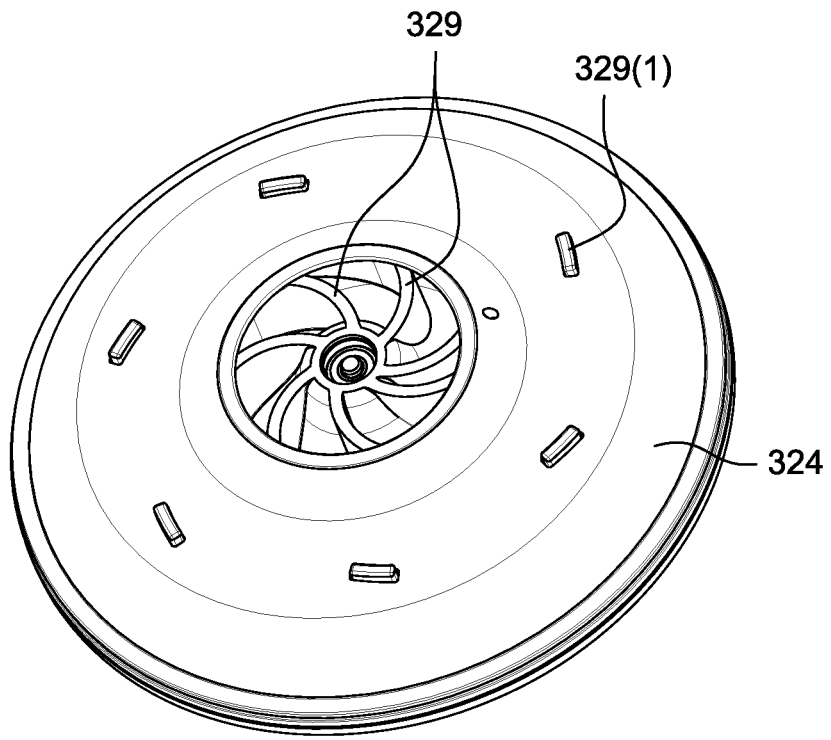
Figure 127:
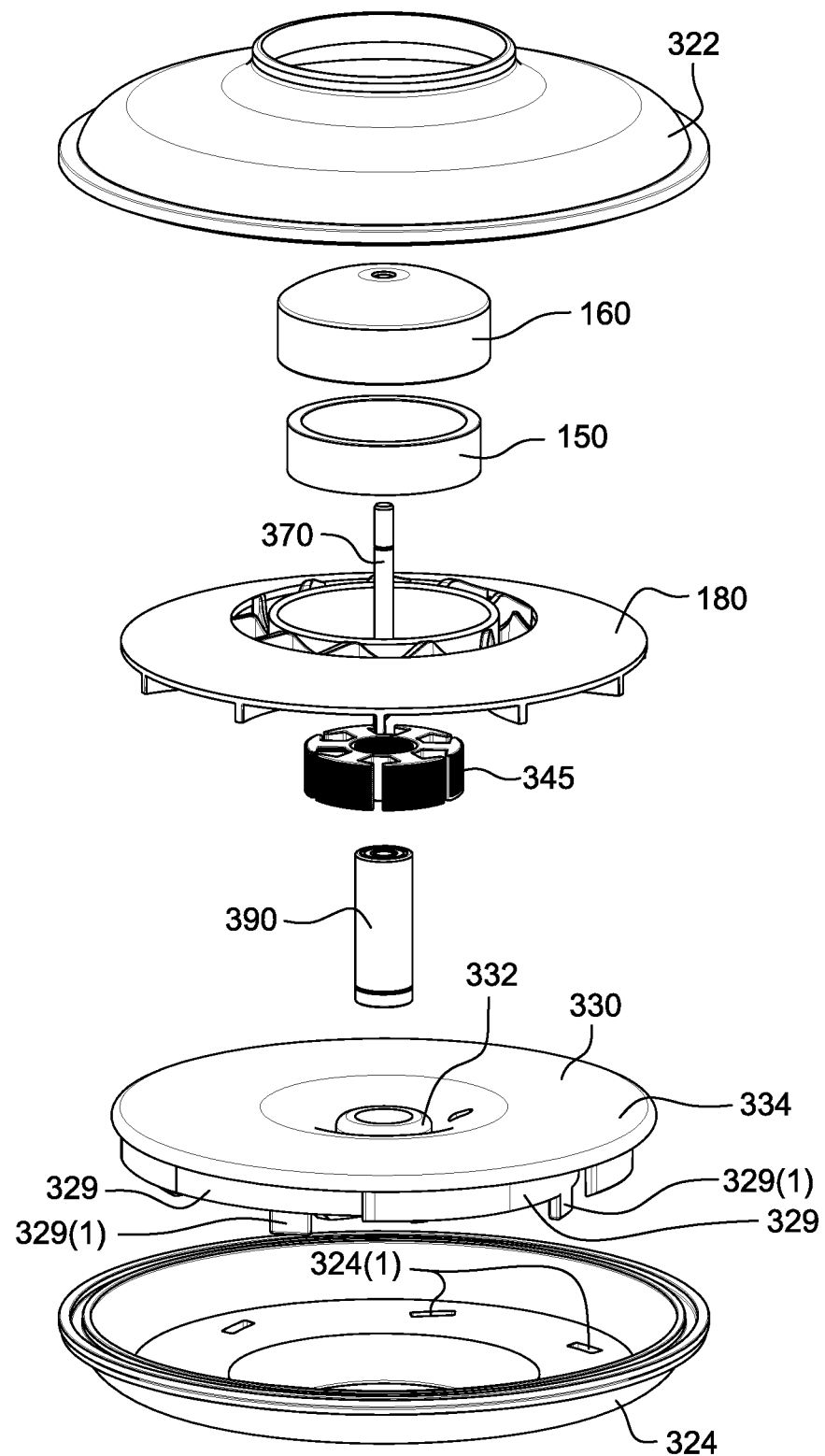
Figure 128:
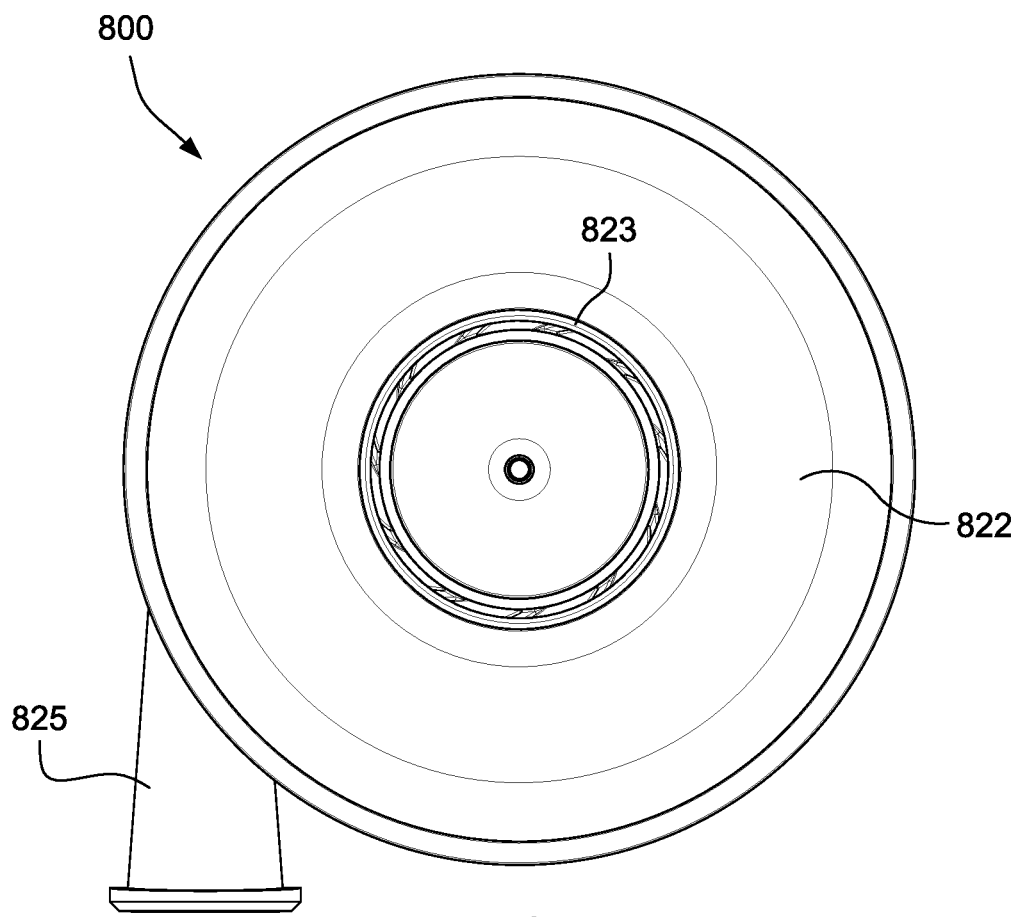
FIGS. 128 to 131 show various views of a blower according to another example of the present technology.
Figure 129:
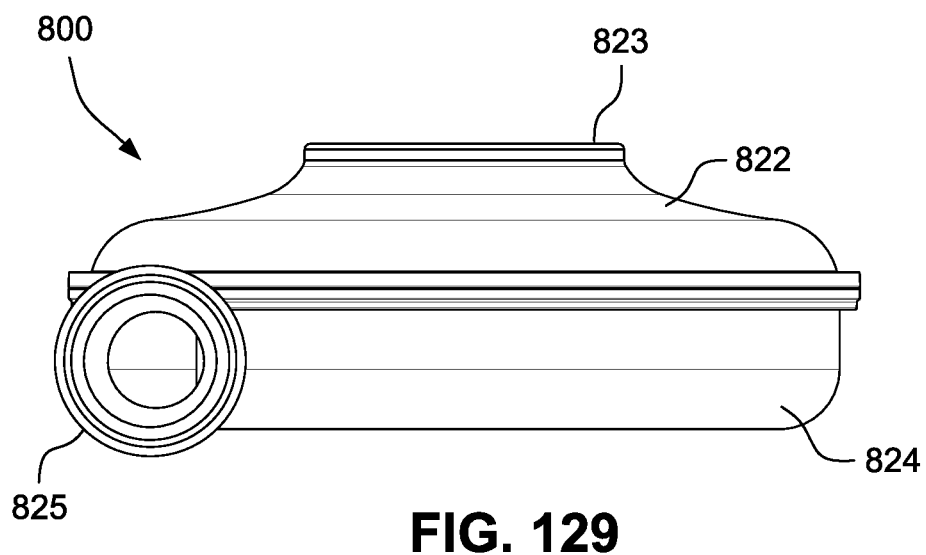
Figure 130:
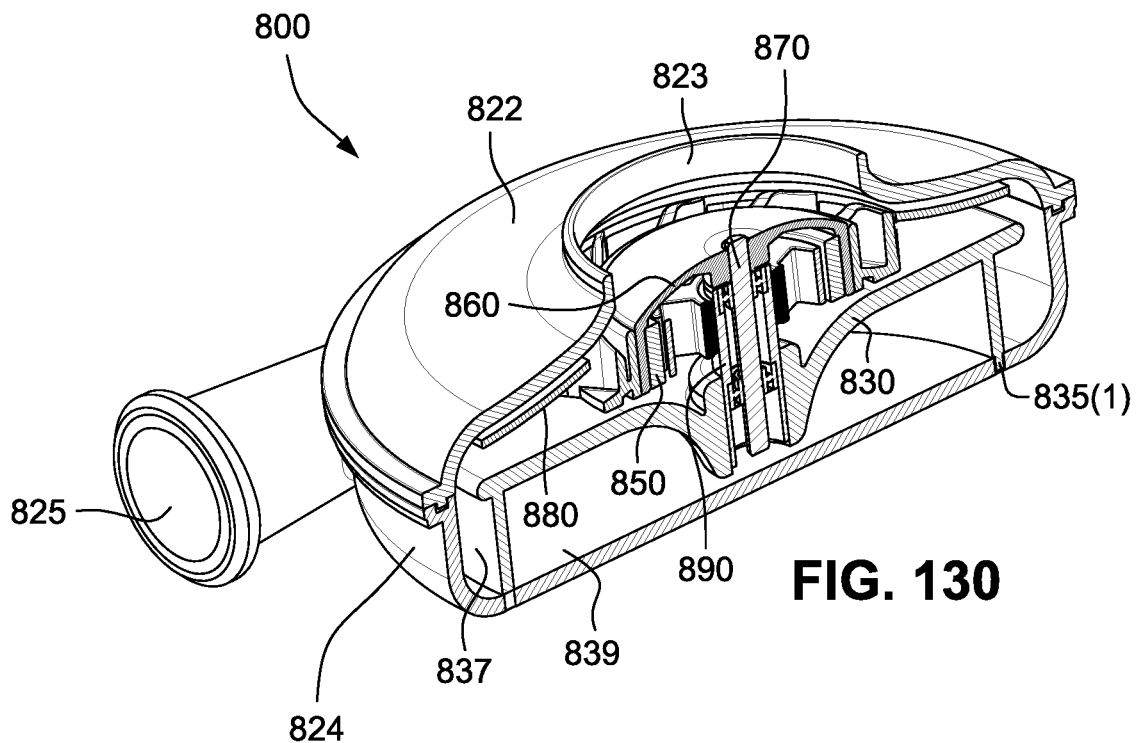
Figure 131:
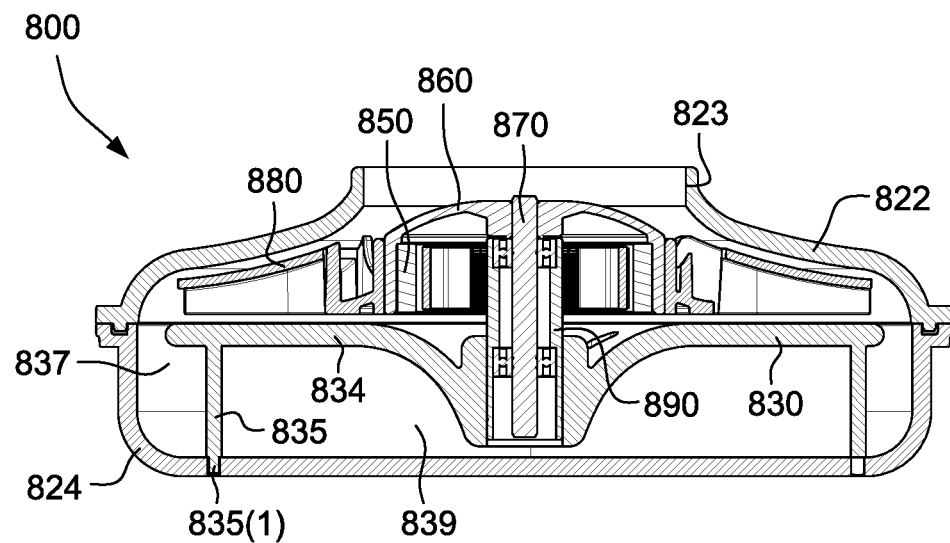
Figure 132:
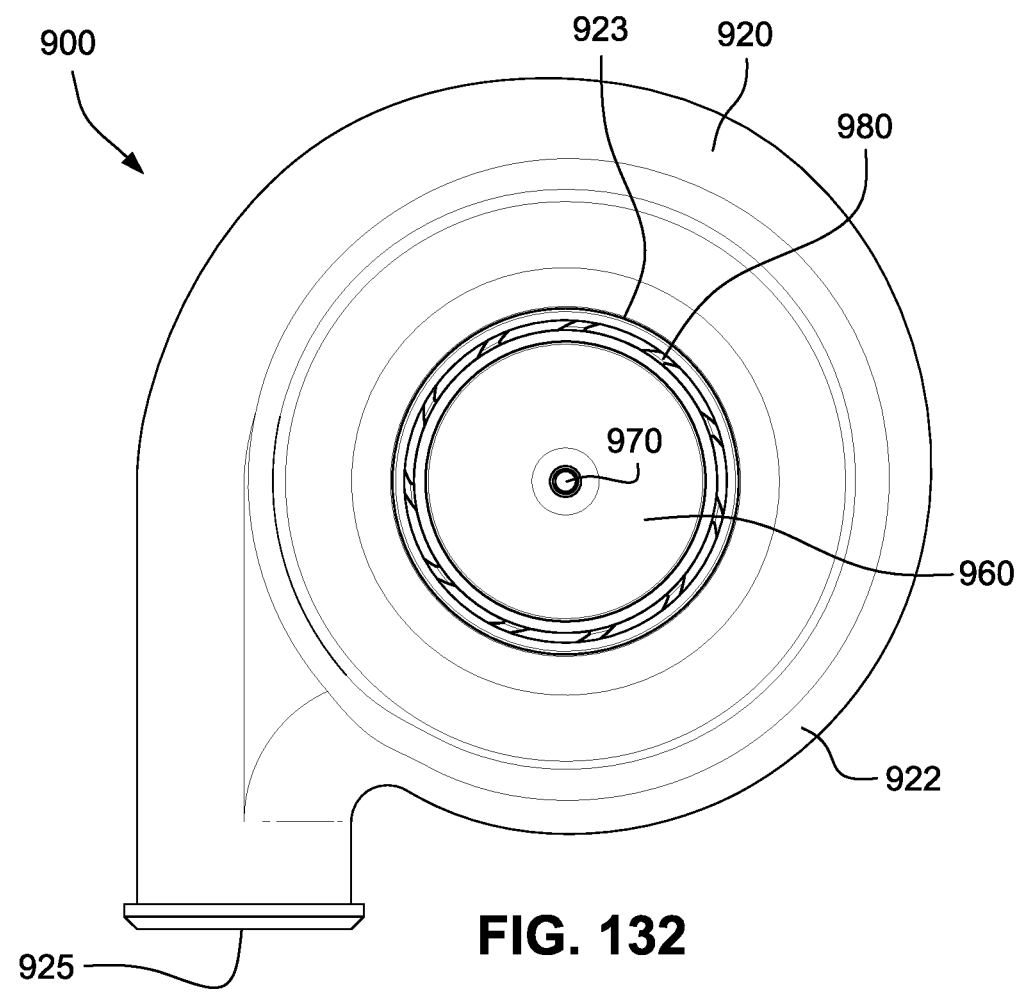
FIGS. 132 to 138 show various views of a blower according to another example of the present technology.
Figure 133:
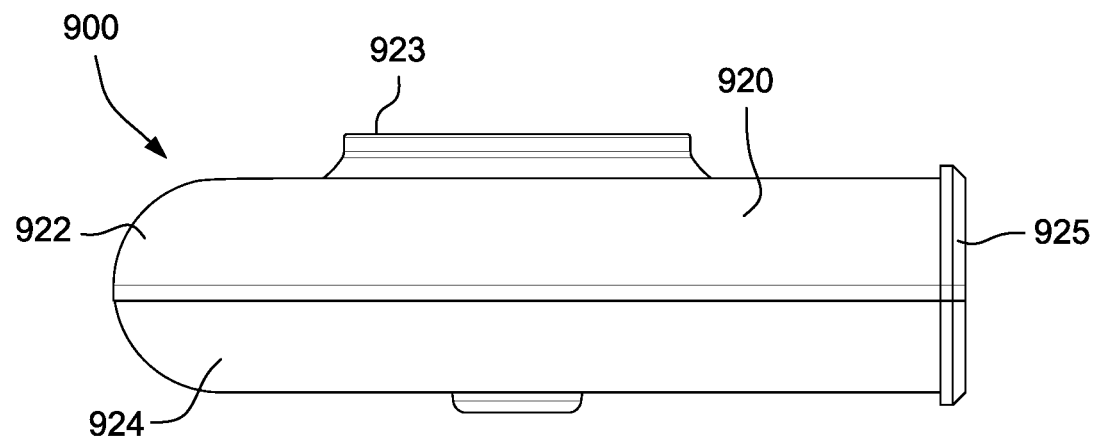
Figure 134:
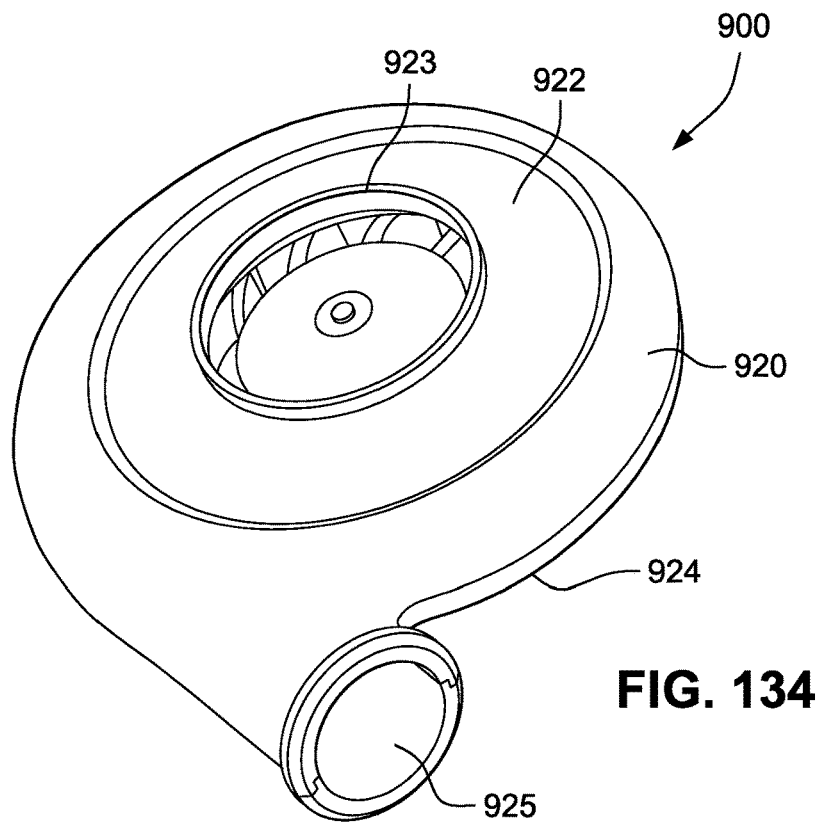
Figure 135:
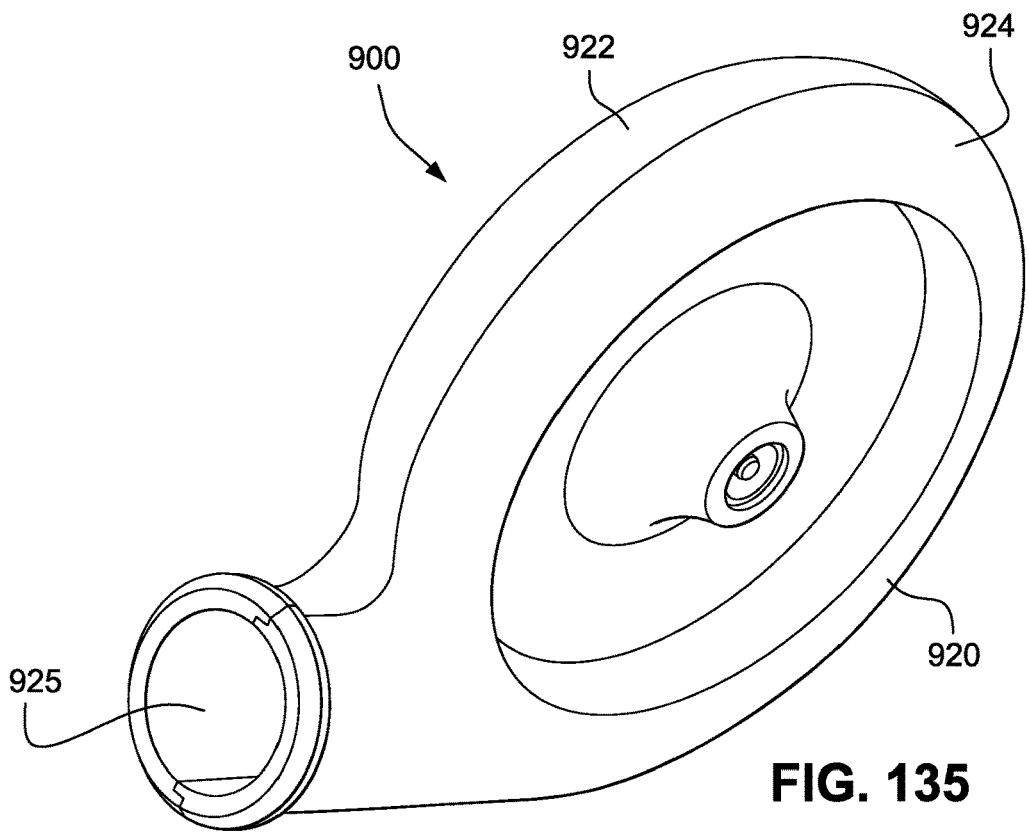

In an example, as shown in FIG. 124, the clearance A between the rotor cap 360 and inner portion 312 of the inlet cap 310 is substantially similar to the clearance A between the impeller 380 and top cover 322, e.g., clearance A greater than 0.1 mm, e.g., greater than about 0.1 mm to 1.0 mm, such as between 0.3 mm and 0.5 mm, or between 0.35 mm to 0.4 mm, or greater than 0.381 mm, such as greater than about 0.381 mm to 1.0 mm. Also, in an example, as shown in FIG. 124, the thickness B of the inner portion 312 of the inlet cap 310 is substantially similar to the thickness B of the top cover 322.

In the illustrated example, the inlet cap includes three spokes or connectors 316, however it should be appreciated that more or less spokes may be provided, e.g., 2, 4, 5, 6 or more spokes. Also, it should be appreciated that the spokes or connectors may include other configurations and may be arranged in other suitable manners to interconnect the inner and outer portions 312, 314.

Figure 120:
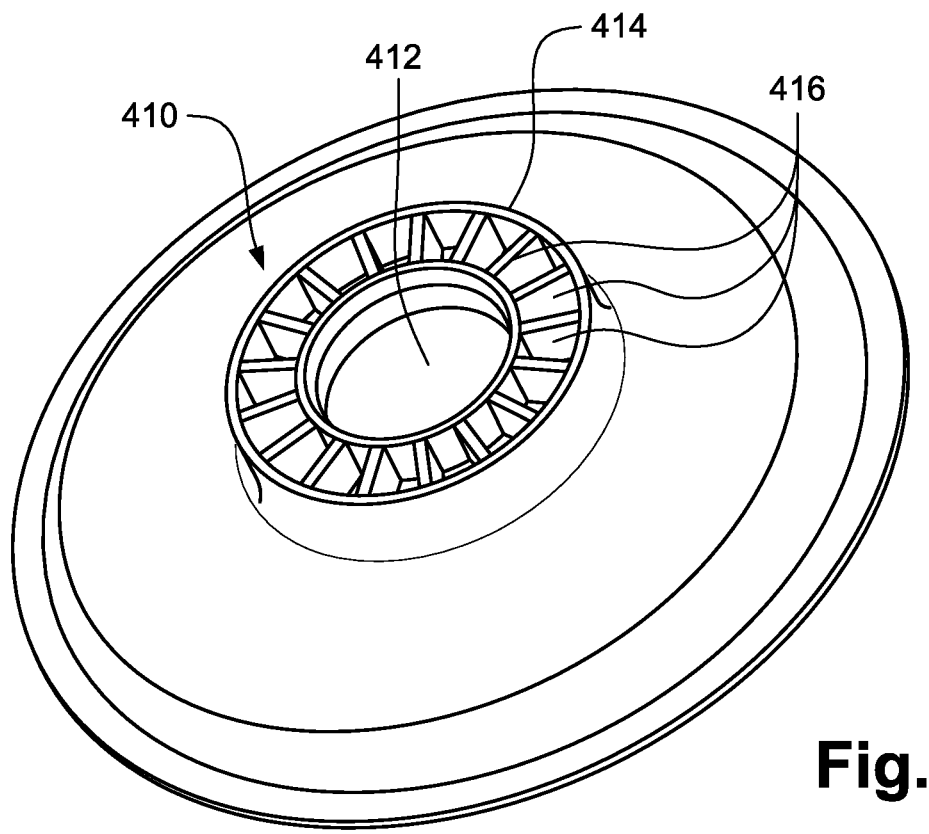
FIG. 120 is a perspective view of a top cover for a blower including an inlet cap according to an example of the present technology.

For example, FIGS. 120 to 123 show inlet caps according to alternative examples of the present technology. In FIG. 120, the inlet cap 410 includes a larger number of radially extending connectors 416, e.g., 17 connectors, than the inlet cap 310 described above interconnecting the inner and outer portions 412, 414. However, it should be appreciated that more or less connectors are possible.

Figure 121:
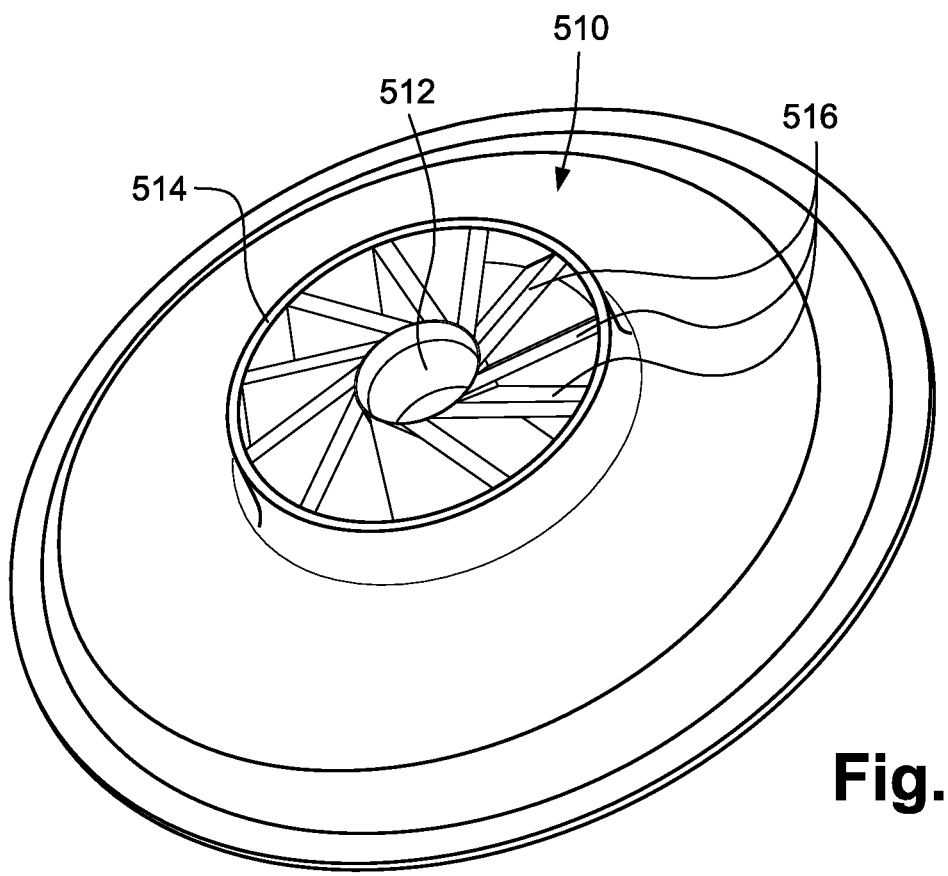
FIG. 121 is a perspective view of a top cover for a blower including an inlet cap according to another example of the present technology.

In FIG. 121, the inlet cap 510 includes a plurality of connectors 516, e.g., 10 connectors, that extend tangentially from the inner portion 512 to interconnect the inner portion 512 with the outer portion 514. Also, the connectors may be skewed or angled towards horizontal, e.g., to enhance noise reduction.

Figure 122:
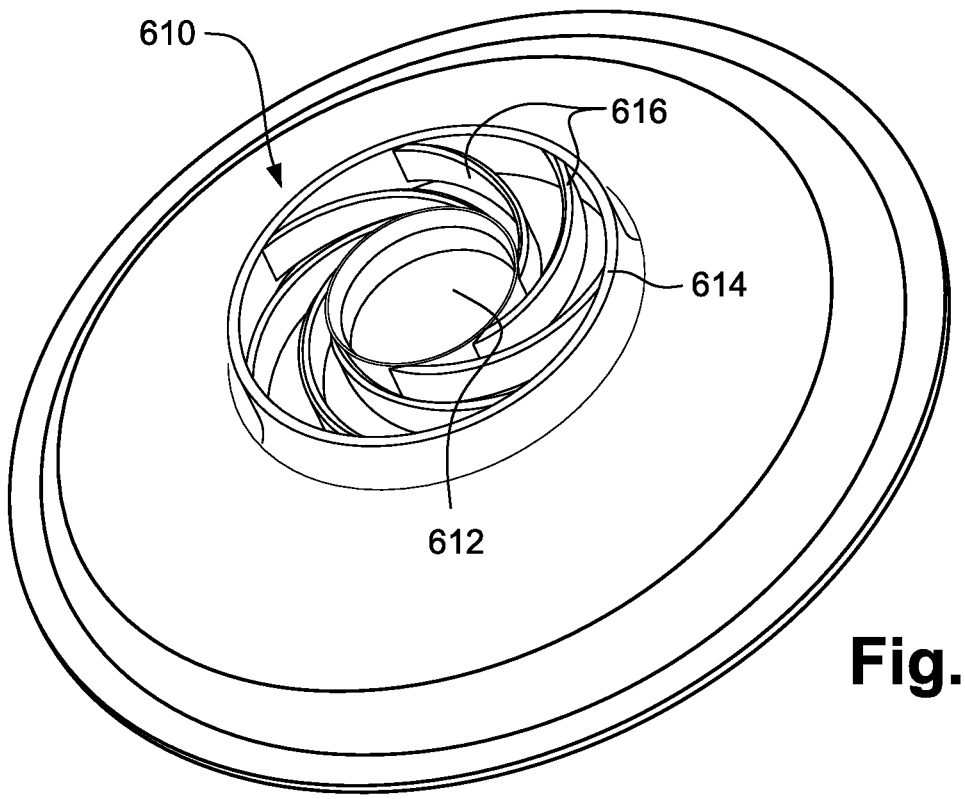
FIG. 122 is a perspective view of a top cover for a blower including an inlet cap according to another example of the present technology.

In FIG. 122, the connectors 616, e.g., 7 connectors, between the inner and outer portions 612, 614 of the inlet cap 610 include a generally curved configuration.

Figure 123:
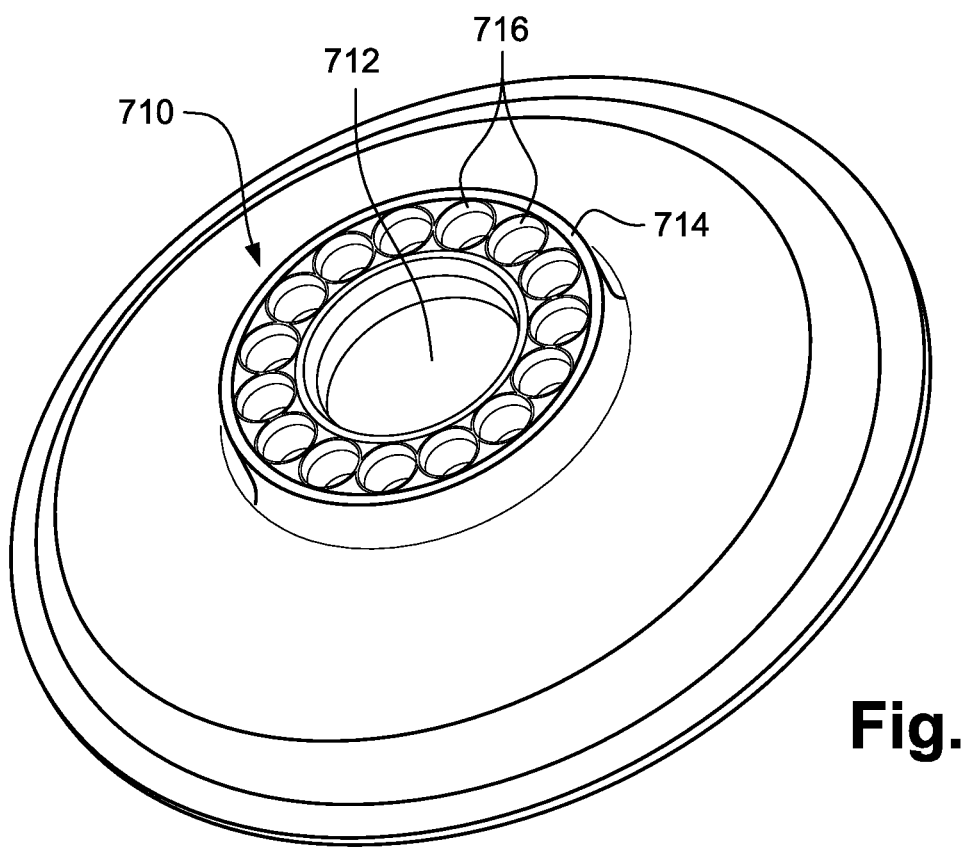
FIG. 123 is a perspective view of a top cover for a blower including an inlet cap according to another example of the present technology.

In FIG. 123, the connectors 716, e.g., 15 connectors, between the inner and outer portions 712, 714 of the inlet cap 710 are in the form of cylinders.

It should be appreciated that the number of connectors 416, 516, 616, 716 may be varied and the above numbers are only exemplary, thus more or less connectors 416, 516, 616, 716 may be utilized, such as 2, 3, 4, 5, 6, 7, 8, 9, 10, 11, 12, 13, 14, 15, 16, 17, 18 or more connectors.

Bearing-Housing Structure

In an example, the blower does not require or use ball bearings to rotatably support the rotor. Rather, the bearing-housing structure 130 (rotatably supports the rotor 170 along with the rotor cap 160 and retains the stator assembly 145 of the motor 140. The bearing-housing structure 130 may also comprise a shielding disk between the impeller blades and the stator vanes. The bearing-housing structure 130 is constructed of a lubricous material such as sintered bronze, an engineered plastic material, e.g., a polyamide-imide resin such as a Torlon™, and/or other very low friction materials or a combination of materials including a lubricous material or a material having a very low coefficient of friction. For example, a first material such as an aluminum, steel, brass, bronze or other metal or plastic may be coated with a lubricous material or material having a very low coefficient of friction such as a ceramic based or a nickel based coating material. In certain examples, the coating may be applied only to the critical wear surfaces of the bearing-housing such as the shaft receiving surface. Alternatively or additionally, the shaft may be coated with such materials to reduce friction.

Figure 10:
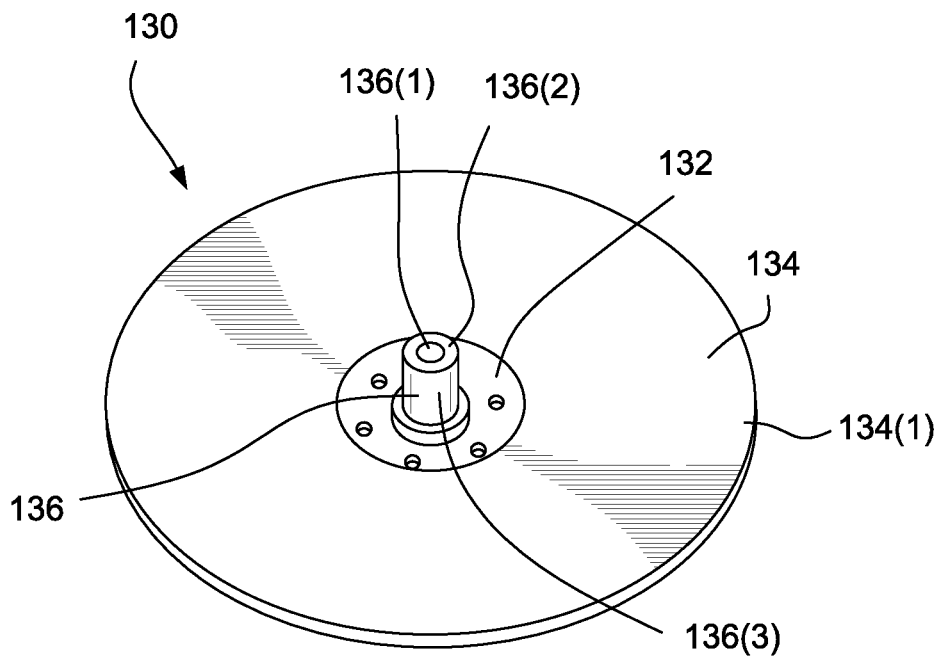
FIG. 10 is a perspective view of a bearing-housing structure of the blower of FIG. 2.
Figure 11:
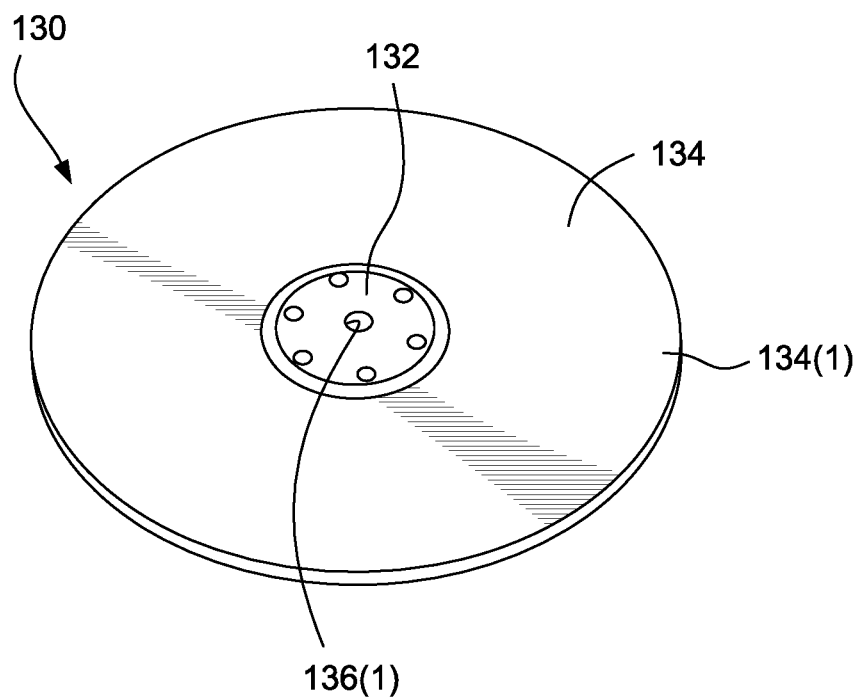
FIG. 11 is a reverse perspective view of the bearing-housing structure of FIG. 10.
Figure 12:
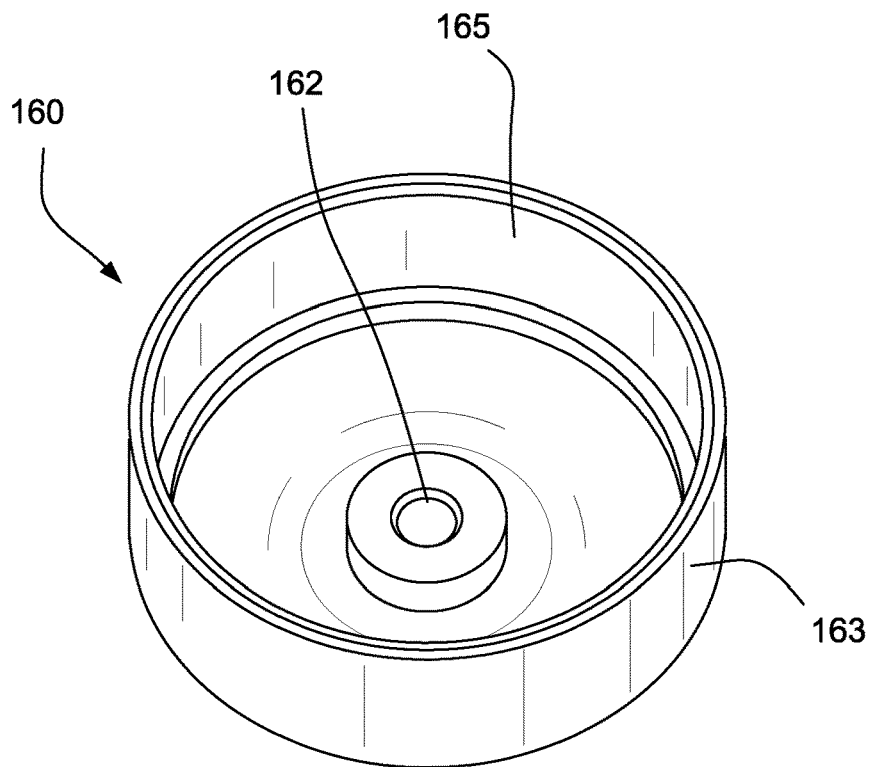
FIG. 12 is a perspective view of a rotor cup of the blower of FIG. 2.
Figure 13:
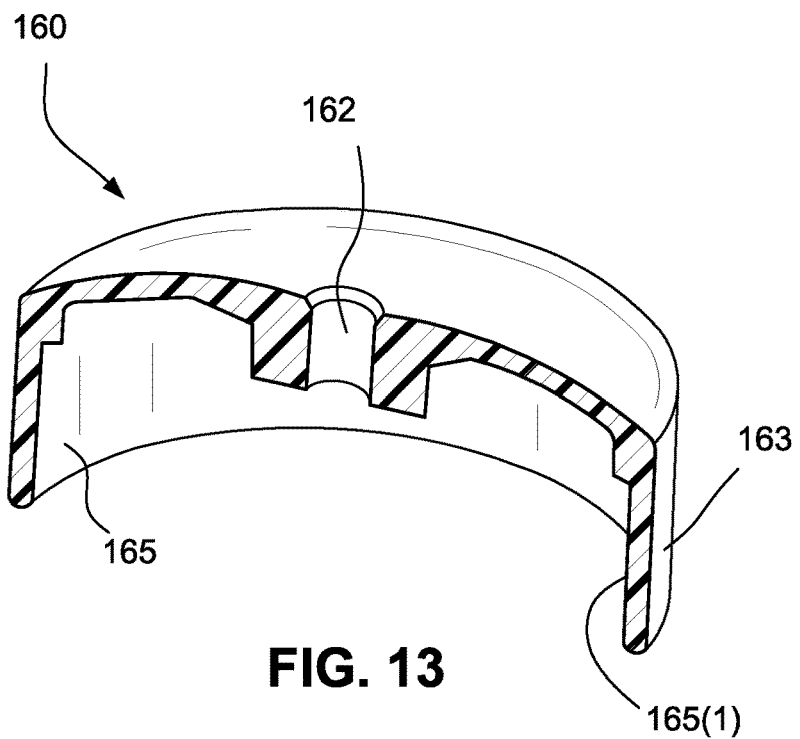
FIG. 13 is a cross-sectional view of the rotor cup of FIG. 12.

As shown in FIGS. 10 and 11, the bearing-housing structure 130 includes a base 132, an annular flange or disk 134 extending from the base, and a rotor or bearing shaft 136 that rotatably supports the rotor 170. The bearing shaft 136 includes a radial or sleeve bearing portion 136(1) and a thrust bearing portion 136(2). The thrust bearing portion 136(2) is at the top surface of the bearing-housing structure 130 surrounding the rotor 170 and adjacent the rotor cap 160. The thrust bearing portion 136(2) provides a thrust surface to allow the rotor cap to rotate. The radial bearing portion 136(1) is configured as a sleeve bearing along the surface of the rotor and provides a radial surface along the rotor to facilitate rotation of the rotor 170. The rotor may be polished to provide a desired surface finish at the rotor cap thrust surface. The surface finish may be attained using one or more techniques including grinding, diamond burnishing, lapping and polishing and/or chemical tumbling or any other surface generation techniques. The surface finish may be provided with a micro finish of between 3 micro-inches root mean square (RMS) to 40 micro-inches RMS, such as 3 micro-inches RMS to 32 micro-inches RMS, such as 8 micro-inches RMS to 16 micro-inches RMS. In certain examples, the surface finish may not be super highly polished as this may create some friction. Alternatively, the surfaces may be coated with a lubricous or very low coefficient of friction material as described above rather than being polished. The bearing shaft provides a single bearing incorporating both radial and thrust bearing properties which assists in reducing the height of the blower. A thrust load may be provided to the thrust bearing portion 136(2) of the bearing-housing structure 130. The thrust load is provided by the rotor cap 160 on a top surface or thrust surface 136(2) of the bearing shaft in use. As there is only a single bearing, the motor only requires balancing in one plane and not two planes.

The disk 134 of the bearing-housing structure provides support to the rotor. The outer edge 134(1) of the disk 134 substantially aligns with or extends radially beyond the outer edge of the impeller 180 to prevent a line of sight between the tips of the impeller blades and the de-swirling vanes 129. The outer edge 134(1) of the disk 134 provides a shielding function to prevent blade pass tonal noise from being generated from the de-swirling vanes of the bottom cover 124 when the impeller spins in use. The disk 134 provides a narrow annular gap 135, e.g., about 0.75 mm, between its outer edge and the side wall of the cover 120, which is sufficient to allow enough gas to flow towards the outlet without significant loss in pressure and motor efficiency. In certain examples, the gap may be between 0.4 mm and 100 mm, e.g., between 0.4 mm and 2 mm, such as 0.5 mm, 0.75 mm, 1 mm or 1.5 mm. Also, the disk may include one or more openings for guiding the motor wire to outside of the air path, e.g., see FIGS. 28, 29, and 35 showing motor wire 203 routed through opening 144 in disk 134.

In certain examples, the bearing-housing structure 130 may have a split configuration that is assembled from a separate disk component 134 and a separate bearing component 136, e.g., also including the base 132. In this split configuration, the disk component 134 and the bearing component 132, 136 may be constructed of different materials. For example, the bearing component 132, 136 may be constructed of a lubricous material as described above and the disk component 134 may be constructed of a plastic, polycarbonate or similar materials. The separate disk component 134 may be coupled to the bearing component 132, 136 using a range of different coupling systems. The coupling system between the disk component 134 and the bearing component 132, 136 may include one or more of the following systems: over molding one component onto the other component, e.g., over molding the disk component 134 onto the base 132 or vice versa; using a snap-fit or clip arrangement; using an interference fit; using a screw or bayonet connection; using an elastomeric component coupled between the disk component 134 and the base 132 such that no direct fastening of the disk component to the base 132 is required, the elastomeric component, e.g., TPE, may be over molded onto the end of the disk component, or the base 32 or both; or any other coupling system. One or more elastomeric or complaint components, such as TPE over molds or o-rings, may be included in any of the above coupling systems between the disk component 134 and the base 132 to reduce the transmission of vibration.

Figure 39:
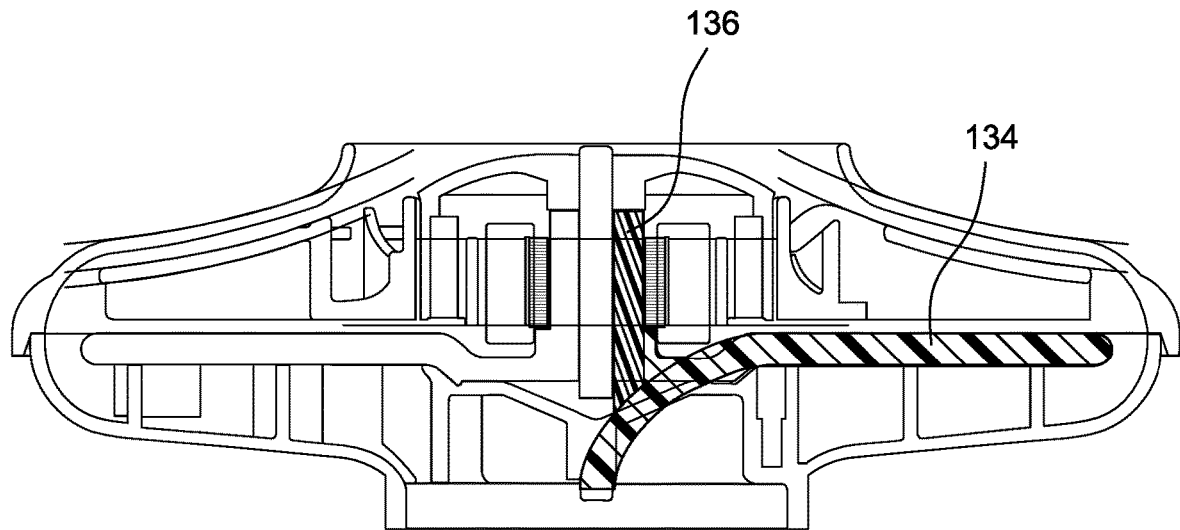
FIG. 39 is a cross-sectional view showing a bearing-housing structure with a split configuration according to an example of the present technology.
Figure 40:
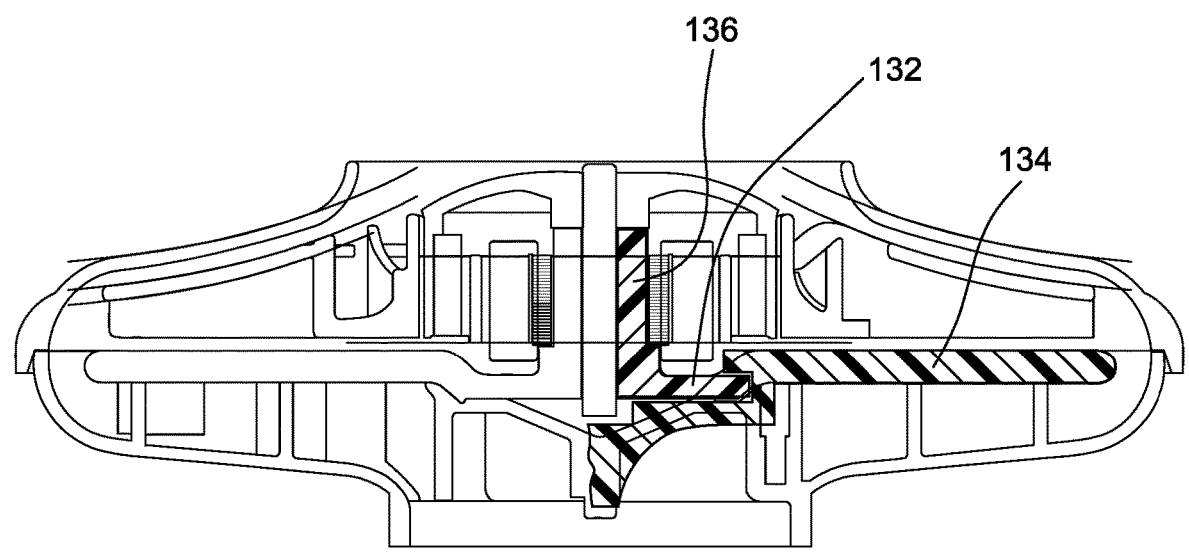
FIG. 40 is a cross-sectional view showing a bearing-housing structure with a split configuration according to another example of the present technology.
Figure 41:
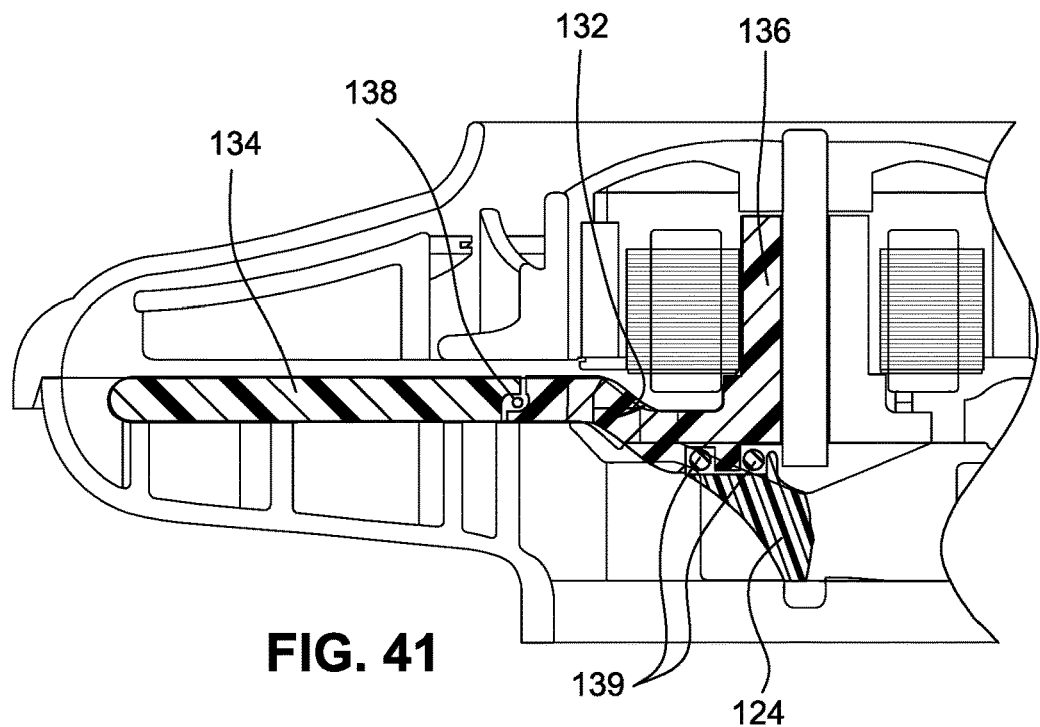
FIGS. 41 and 42 are a cross-sectional views showing a bearing-housing structure with a split configuration according to another example of the present technology.
Figure 42:
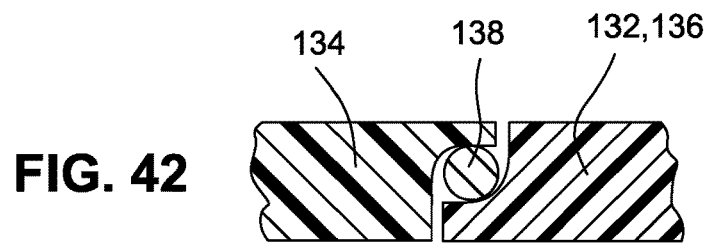
Figure 45:
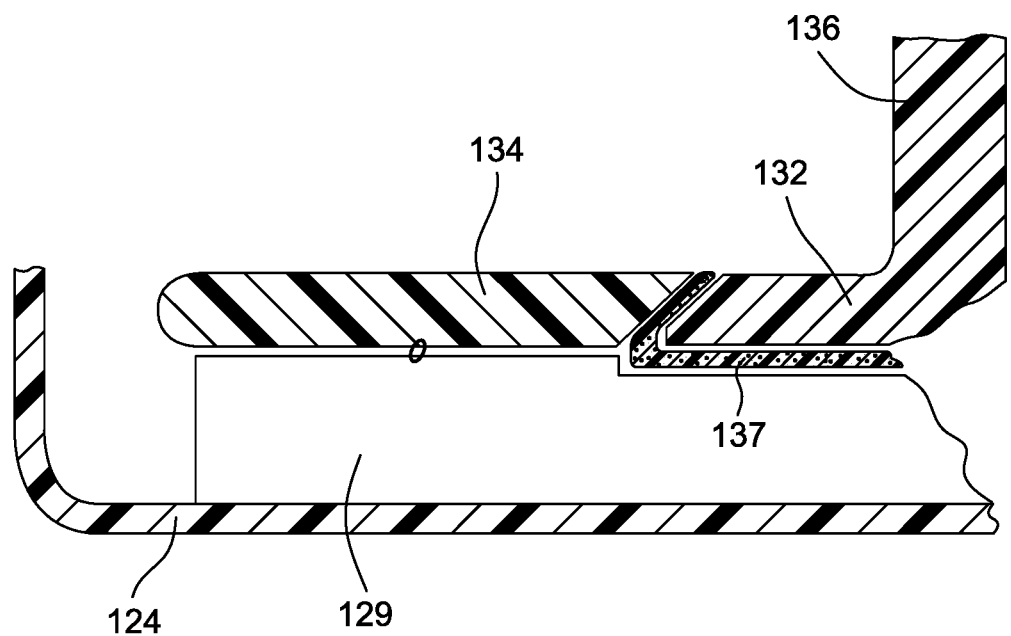
FIG. 45 is a cross-sectional view showing a bearing-housing structure with a split configuration according to another example of the present technology.

For example, FIG. 39 shows an example of a separate disk component 134 coupled to a separate, cylindrical bearing component 136, e.g., overmolded with one another. In FIG. 40, the base 132 of the separate bearing component 136 is interlocked within a groove provided to the separate disk component 134, e.g., to enhance connection between components. In FIGS. 41 and 42, an o-ring 138 is provided between the separate disk component 134 and the separate bearing component 132, 136, e.g., to minimize vibration transmission. Also, one or more o-rings 139 may be provided between the bearing component 132, 136 and the bottom cover 124 to minimize vibration transmission. FIG. 45 shows a separate bearing component 132, 136 with an elastomer 137 overmolded along the edge of the base 132. The separate disk component 134 (e.g., constructed of plastic) may be ultrasonically welded or heat staked to vanes 129 of the bottom cover 124.

Figure 43:
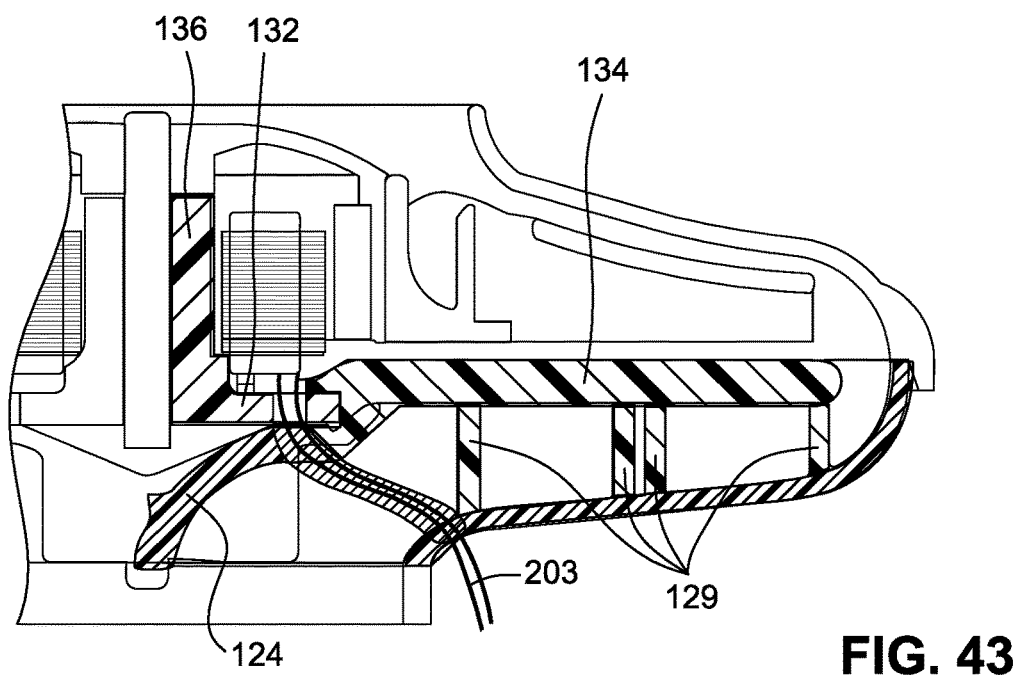
FIG. 43 is a cross-sectional view showing a bearing-housing structure with a split configuration according to another example of the present technology.

In such split configuration examples, the plurality of stator vanes or de-swirling vanes 129 positioned below the disk component 134 may be either located on the disk component or on the bottom cover 124 as described above or both, such that some of the stator vanes 129 are located on the disk component 134 and some of the stator vanes 129 are located on the bottom cover 124 to provide the complete set of stator vanes 129. The stator vanes 129 may be integrally formed or molded with the disk component 134 and/or the bottom cover 124. For example, FIG. 43 shows a separate bearing component 132, 136 overmolded with a separate disk component 134, the disk component 134 including stator vanes 129 integrally formed or molded therewith. The bottom cover 124 supports the end portion of the vanes, e.g., end portion of vanes molded into the bottom cover.

Figure 44:
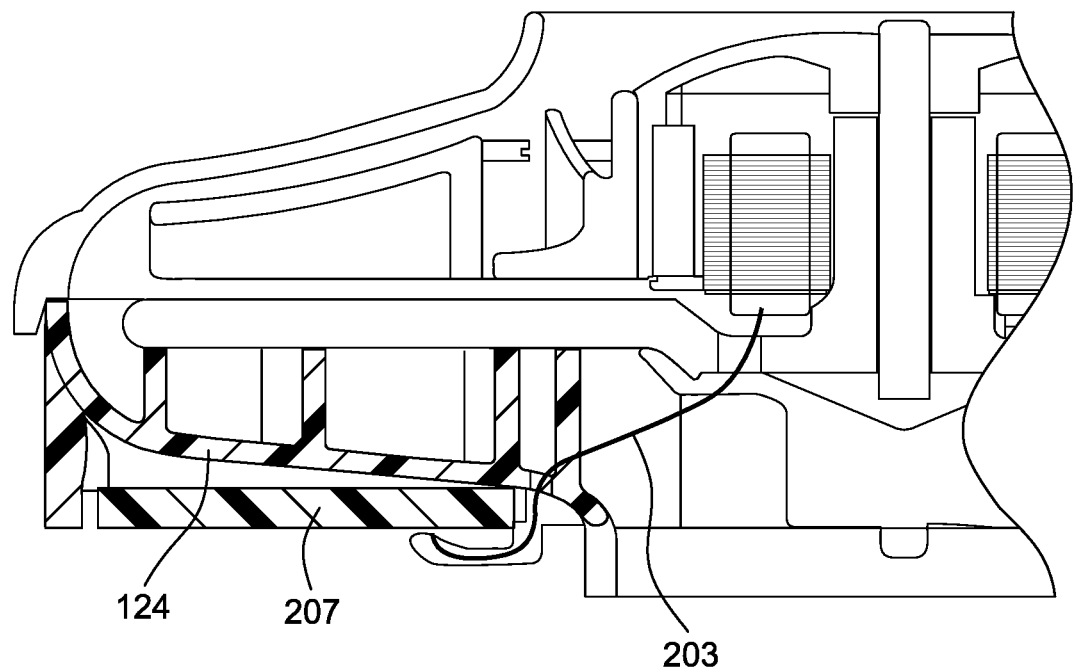
FIG. 44 is a cross-sectional view of a blower showing motor wire routing and PCB mounting according to an example of the present technology.

Such split configurations allow motor wires or stator wires to be routed out of the blower assembly between the disk 134 and base 132, e.g., see FIG. 43 showing motor wires 203 routed between disk component 134 and bearing component 132, 136 and through an exit in the bottom cover 124. The motor wires may be routed to an exit within the bottom cover and attached to a PCB Assembly or driver, e.g., see FIG. 44 showing motor wires 203 routed through bottom cover 124 and to the PCB assembly or driver 207. The motor wires may also be routed through at least some of the stator vanes 129 as described above. In certain examples, the PCB assembly or driver may be mounted to the bottom cover outside the air path, e.g., see FIG. 44 in which PCB assembly or driver 207 mounted to exterior portion of the bottom cover 124 outside the air path.

In other certain examples, the disk 134 may be a separate component that acts as a shield as described in U.S. Pat. No. 7,866,944 entitled "Compact low noise efficient blower for CPAP devices," which is incorporated herein by reference in its entirety.

The bearing-housing structure may be coupled to the bottom cover 124 to facilitate assembly of the blower. The bearing-housing structure 130 may be coupled to the bottom cover 124 at 2 or more positions, such as 3-6 positions or more. At least some of the stator vanes 129 on the bottom cover may be coupled to the disk 134 of the bearing-housing structure 130. However, if the stator vanes are located on the disk 134, at least some of the stator vanes 129 may be coupled to the bottom cover. The stator vanes 129 may be coupled to the disk 134 and/or the bottom cover by any means including one or more of the methods described below or combinations thereof or any other coupling method.

Figure 46:
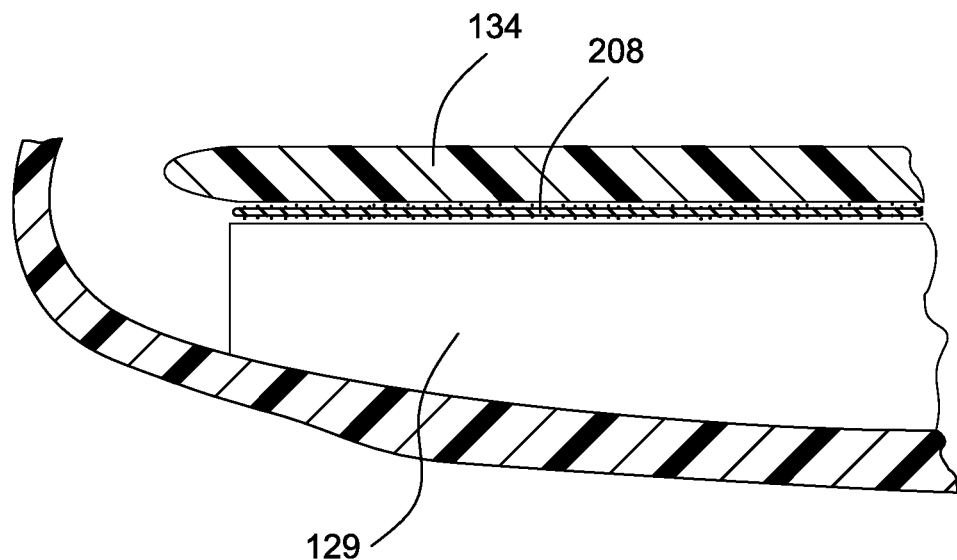
FIG. 46 is a cross-sectional view showing a bearing-housing structure coupled to vanes of the bottom cover according to an example of the present technology.
Figure 47:
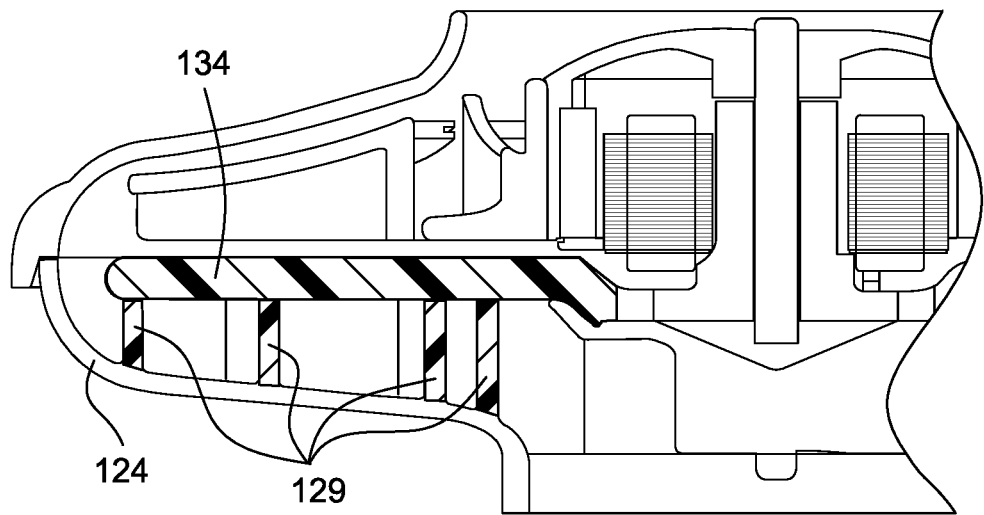
FIG. 47 is a cross-sectional view showing a bearing-housing structure coupled to vanes of the bottom cover according to another example of the present technology.

In certain examples, at least some of the stator vanes 129 may be adhesively coupled to the disk 134 and/or bottom cover 124, such as using a glue or double side tape. For example, FIG. 46 shows the disk 134 coupled to stator vanes 129 by double side tape 208. FIG. 47 shows an example, in which the stator vanes 129 of the bottom cover 124 are overmolded TPE or hard plastic which may be adhesively bonded to the disk 134. In other examples, the stator vanes 129 may be coupled to the disk 134 and/or bottom cover 124 by heat staking or ultrasonic welding. For example, FIG. 29 shows the bearing-housing structure 130 heat-staked onto the bottom cover 124. In such example, the vanes 129 are overmolded with an elastomer 129-5, e.g., to minimize vibrations. In other examples, the stator vanes 129 may be coupled to the disk 134 and/or bottom cover 124 using a press-fit arrangement wherein protrusions on an edge of the stator vanes are received within complementary apertures in the disk 134 or bottom cover 124 or vice versa in that the protrusions are on the disk 134 and/or bottom cover 124 and the complementary apertures are on the stator vanes 129. Further examples may utilize a snap-fit, interference fit, clip or boss arrangement to couple the stator vanes 129 to the disk 134 and/or bottom cover 124.

Figure 48:
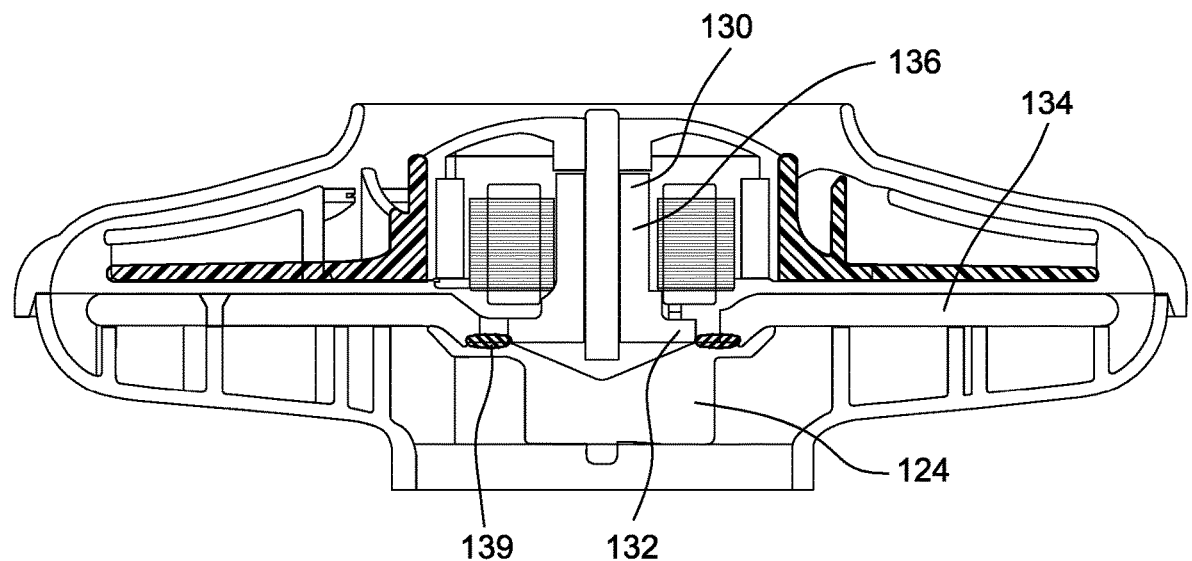
FIG. 48 is a cross-sectional view of a blower with elastomeric material between the bearing-housing structure and the bottom cover according to an example of the present technology.

The top or bottom edges of the stator vanes 129 may include an elastomeric material to minimize vibration transmission from the bearing housing structure 134 to the bottom cover 124. The elastomeric material may be overmolded, adhesively attached, or inserted on to the edges of the stator vanes 129. The elastomeric material, such as an o-ring, may be retained between the coupled stator vanes 129 and the disk 134 and/or bottom cover due to coupling means. For example, FIG. 48 illustrates an o-ring or TPE overmold 139 placed between the bearing housing structure 130 and the bottom cover 124 for vibration isolation. The bearing housing structure may be heat staked onto the bottom cover to retain the o-ring in position.

Figure 49:
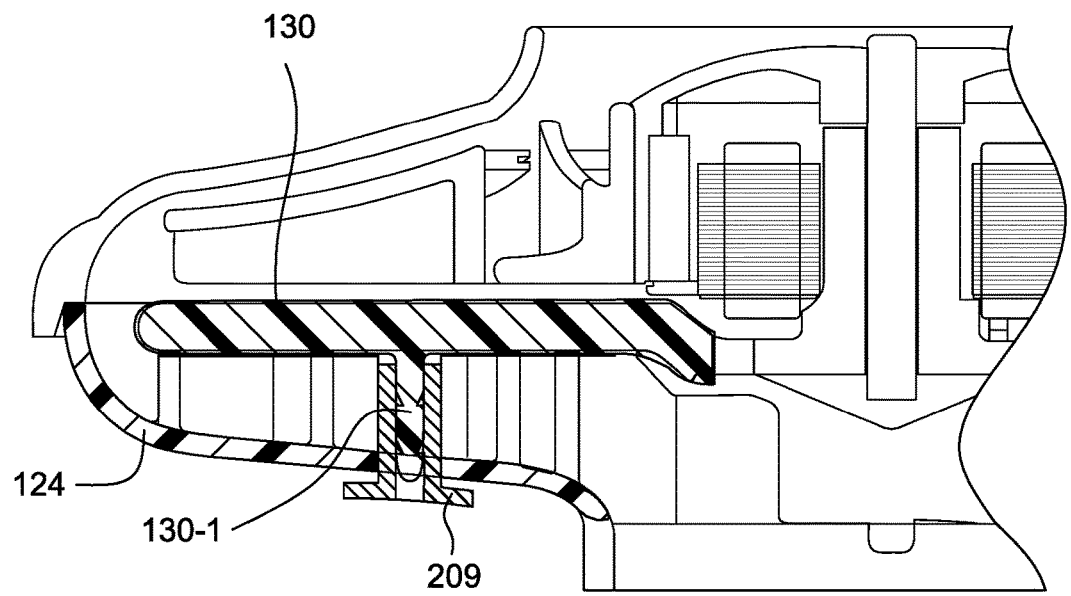
FIGS. 49 and 50 are cross-sectional views showing a bearing-housing structure coupled to the bottom cover by a fastener according to an example of the present technology.
Figure 50:
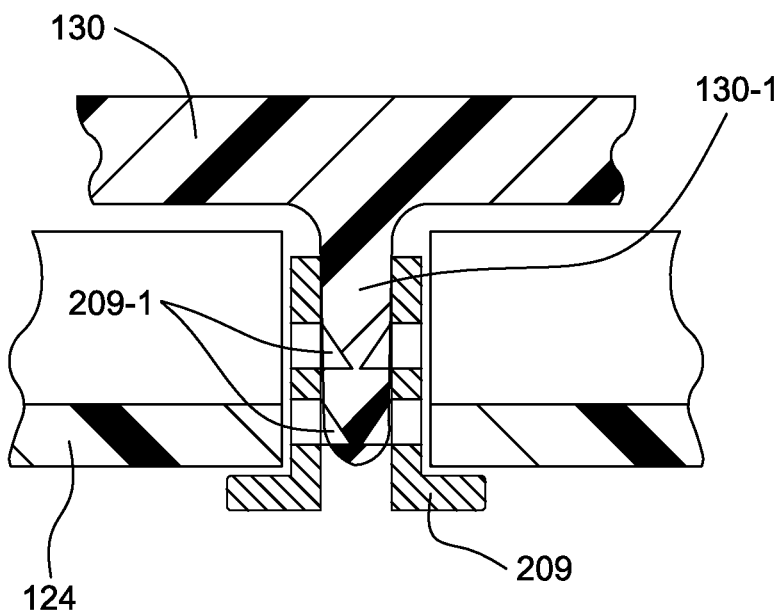
Figure 51:
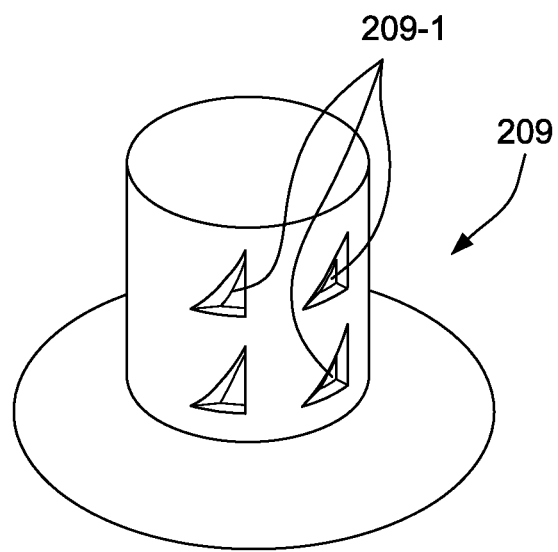
FIGS. 51 and 52 are various views of the fastener of FIGS. 49 and 50.
Figure 52:
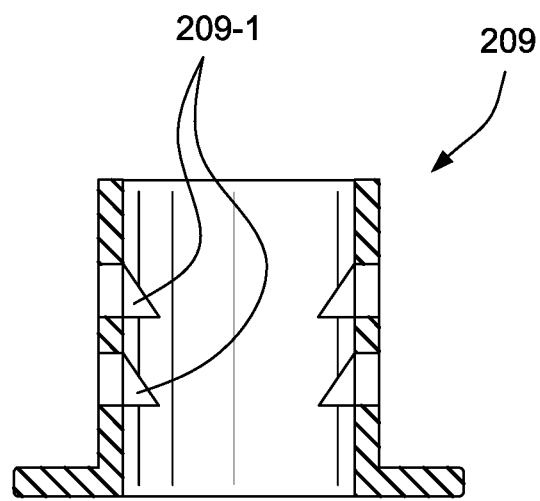

In certain examples, the bearing-housing structure 130 may be coupled additionally or alternatively directly to the bottom cover 124, i.e., not via the stator vanes 129. In an example as shown in FIGS. 49 and 50, the bearing-housing structure 130 may comprise a boss 130-1 that is engaged with a fastener 209 at the bottom cover 124. As best shown in FIGS. 50 to 52, the fastener 209 may include a plurality of teeth-like protrusions 209-1 that grip or bite into and retain the boss 130-1. The teeth-like protrusions may be angled to allow ease of insertion of the boss in one direction but prevent or hinder release of the boss in the opposing direction. The fastener may be a separate component that is inserted through the bottom cover to couple the bottom cover 124 and housing-bearing structure 130. Alternatively, the boss may be located on the bottom cover 124 and the fastener on the bearing-housing structure 130.

Figure 53:
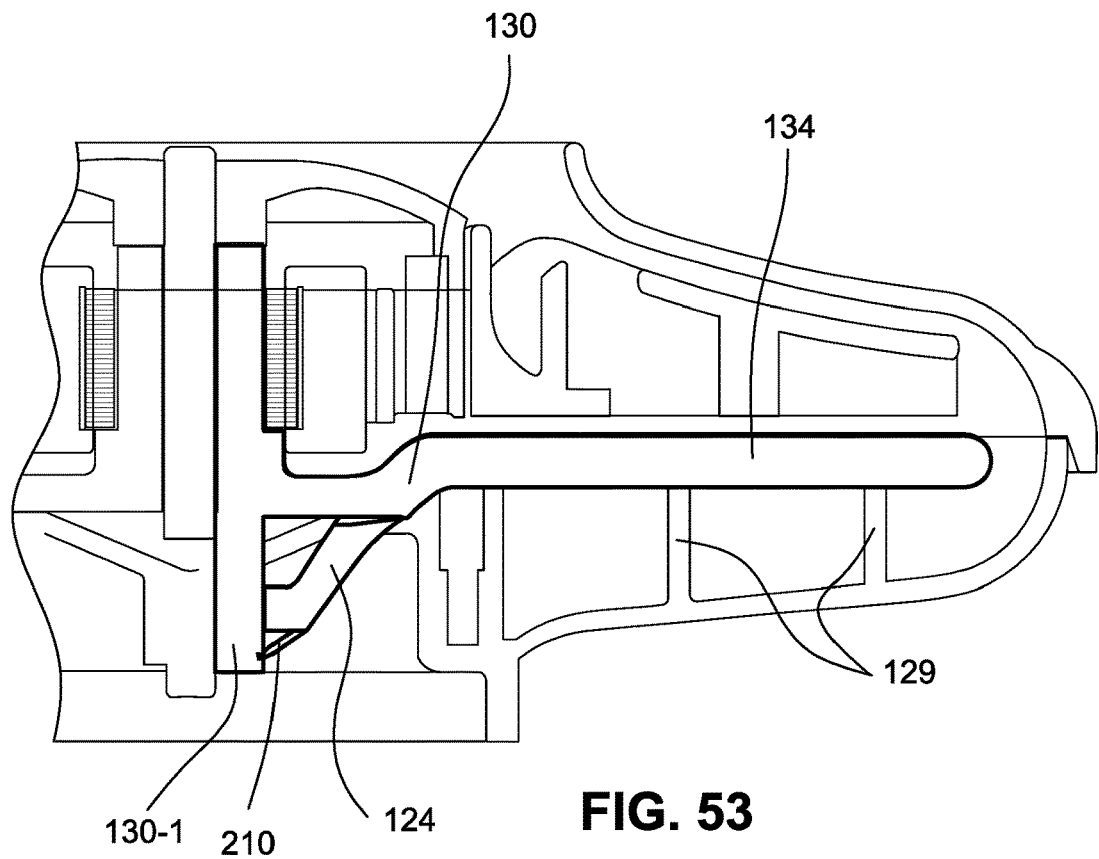
FIG. 53 is a cross-sectional view showing a bearing-housing structure coupled to the bottom cover according to another example of the present technology.
Figure 54:
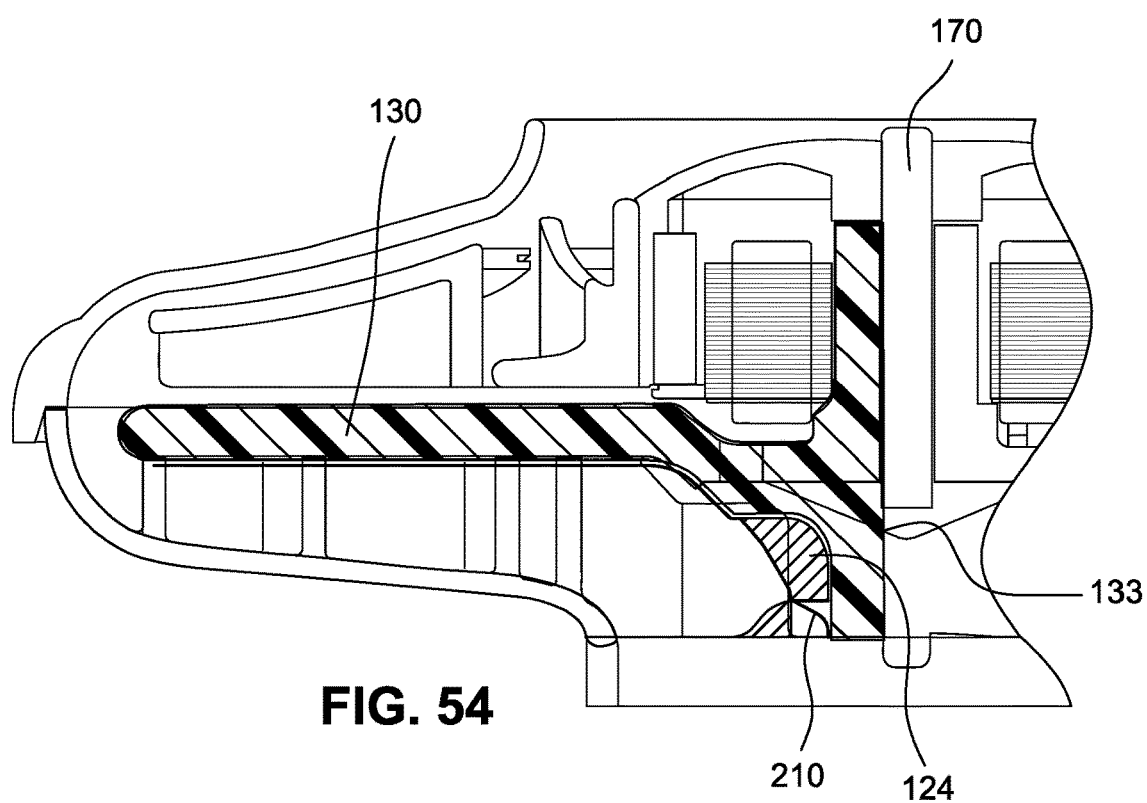
FIG. 54 is a cross-sectional view showing a bearing-housing structure coupled to the bottom cover according to another example of the present technology.

In another arrangement, as shown in FIG. 53, the boss 130-1 may be integrated with the bearing housing structure 130 and configured to press-fit into the bottom cover 124 until at least a portion of some of the stator vanes 129 contact the disk 134 of the bearing housing structure 130. A fastener 210, such as a Tinnerman clip, pal nut, speed nut, push nut or other fastener, may secure the bearing housing structure to the bottom cover. FIG. 54 shows another example of the bearing housing structure 130 secured to the bottom cover 124 by a fastener 210, e.g., Tinnerman clip. In this example, the bearing bore or through hole 133 in the bearing housing structure in the area of the bottom cover (i.e., lower portion of bore 133) may be slightly larger in diameter as compared to area of the bearing sleeve or rotor support (i.e., upper portion of bore 133 that supports rotor 170) to minimize compressive shrink due to press fit of fastener, e.g., Tinnerman clip.

In other certain examples, the boss of the bearing-housing structure 130 may comprise a protrusion including one or more lips that are configured to engage with a fastener at the bottom cover 124. The fastener may have one or more mating grooves adapted to receive the lip(s) in a snap fit arrangement. Alternatively, the protrusion may be located on the bottom cover 124 and the fastener on the bearing-housing structure 130. Other fasteners that may be used include Tinnerman clips, pal nuts, speed nuts, push nuts and other such fasteners.

Figure 55:
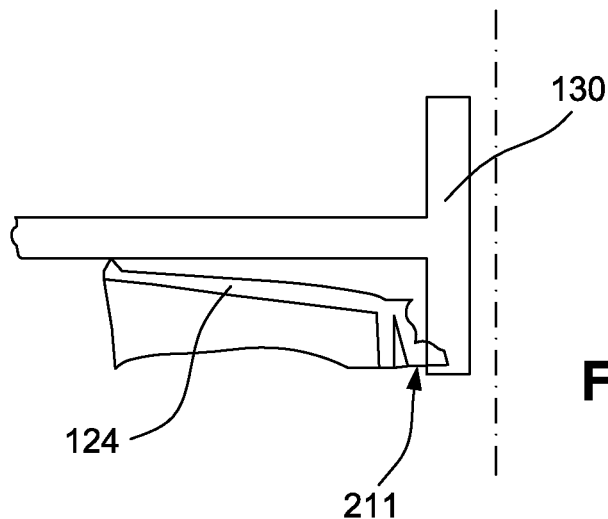
Figure 56:
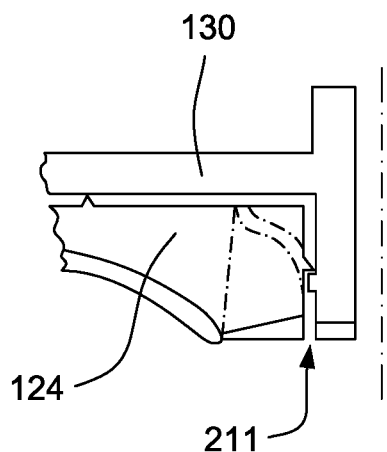
Figure 57:
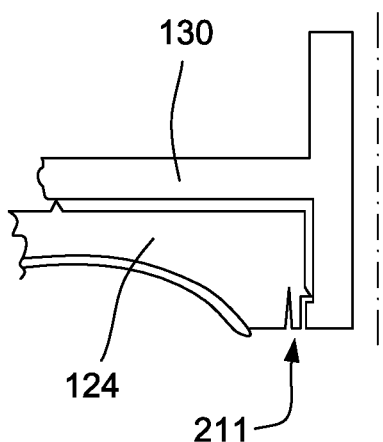
Figure 58:
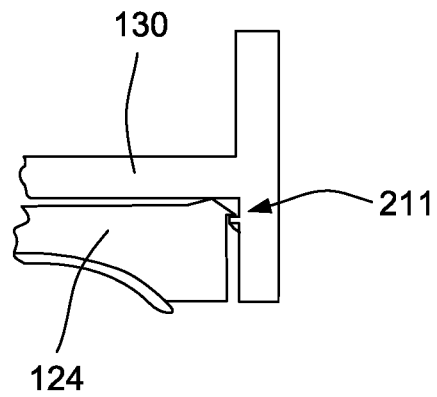
Figure 63:
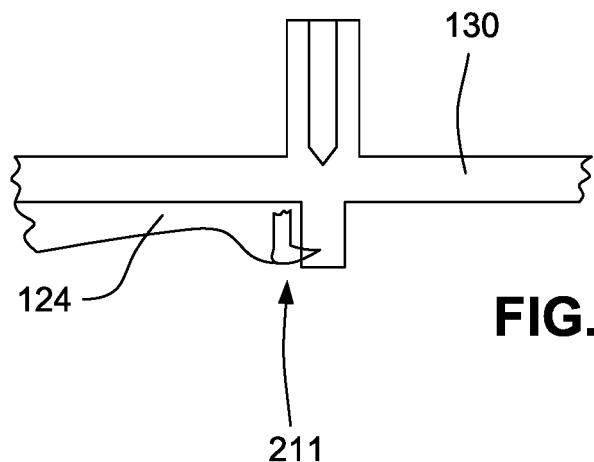
Figure 64:
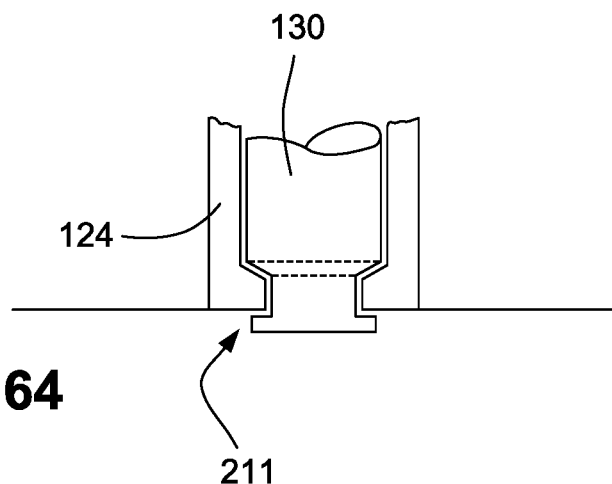
Figure 65:
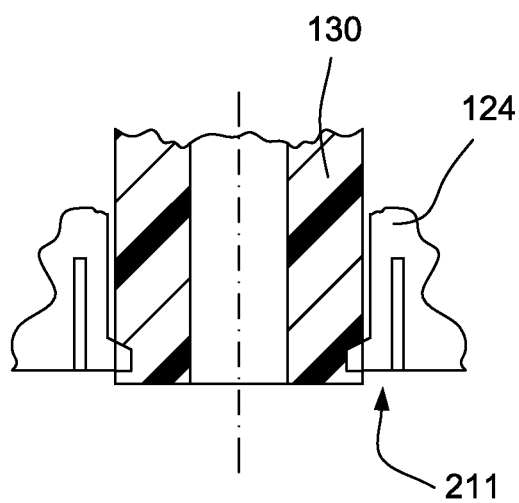

In other examples, the base 132 of the bearing-housing structure 130 may be directly coupled to the bottom cover 124 via a snap feature that snaps into a groove. The snap feature may be located on the bottom cover 124 and the groove on the bearing-housing structure 130 or vice versa. For example, FIG. 55 shows a bottom cover 124 including a snap feature 211 structured to snap into a groove provided on the bearing housing structure 130 to attach the bottom cover the bearing housing structure. FIGS. 56 to 65 show alternative examples of snap features 211 for attaching the bottom cover 124 to the bearing housing structure 130.

Figure 66:
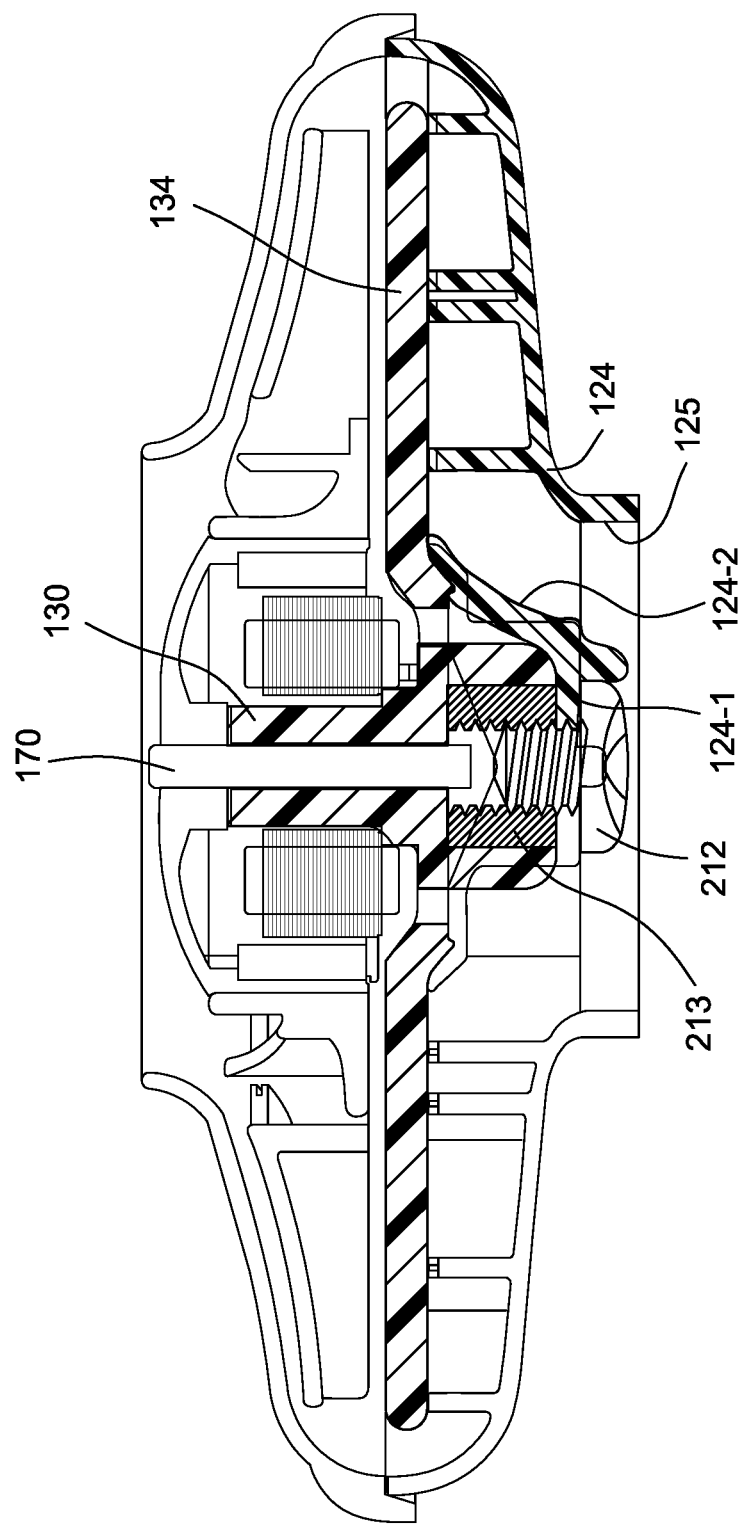
FIG. 66 is a cross-sectional view showing a bearing-housing structure coupled to the bottom cover by a screw arrangement according to an example of the present technology.
Figure 67:
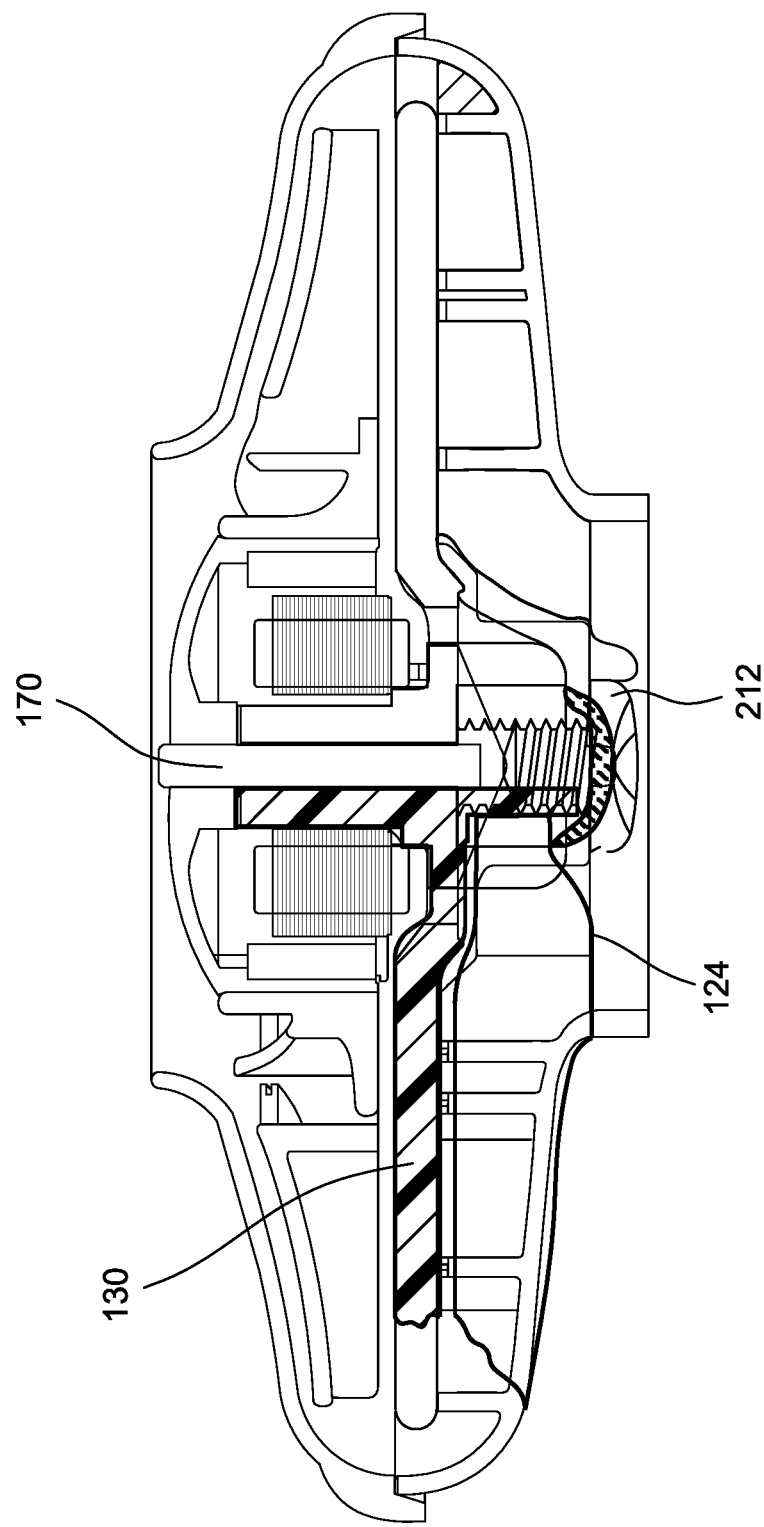
FIG. 67 is a cross-sectional view showing a bearing-housing structure coupled to the bottom cover by a screw arrangement according to another example of the present technology.

In certain examples, as shown in FIG. 66, the bottom cover 124 may be coupled to the bearing-housing structure 130 using a screw arrangement. A central screw 212 may be inserted via the outlet 125 through a portion of the bottom cover 124 and into a threaded anchor 213 provided to the bearing-housing structure 130 (e.g., anchor integrally molded or bored). The screw 212 may be inserted into an anchor portion 124-1 of the bottom cover 124 which further comprises at least one arm 124-2 that extends upwards towards the disk 134 of the bearing-housing structure 130 to provide support. The at least one arm 124-2 may be configured to couple with the disk 134, e.g., interlocking engagement. This may facilitate dampening the bottom cover by clamping. Optionally, the screw may be sealed over after assembly to prevent the screw from falling out or being removed or tampered with. The screw may seal the bottom of the bearing spindle and assist in preventing air flow therethrough and any bearing grease or lubricant from drying out. Bearing grease or lubricant may be added to the bearing spindle prior to installing the screw. FIG. 67 shows another example of the bottom cover 124 coupled to the bearing-housing structure 130 by a central screw 212.

Figure 68:
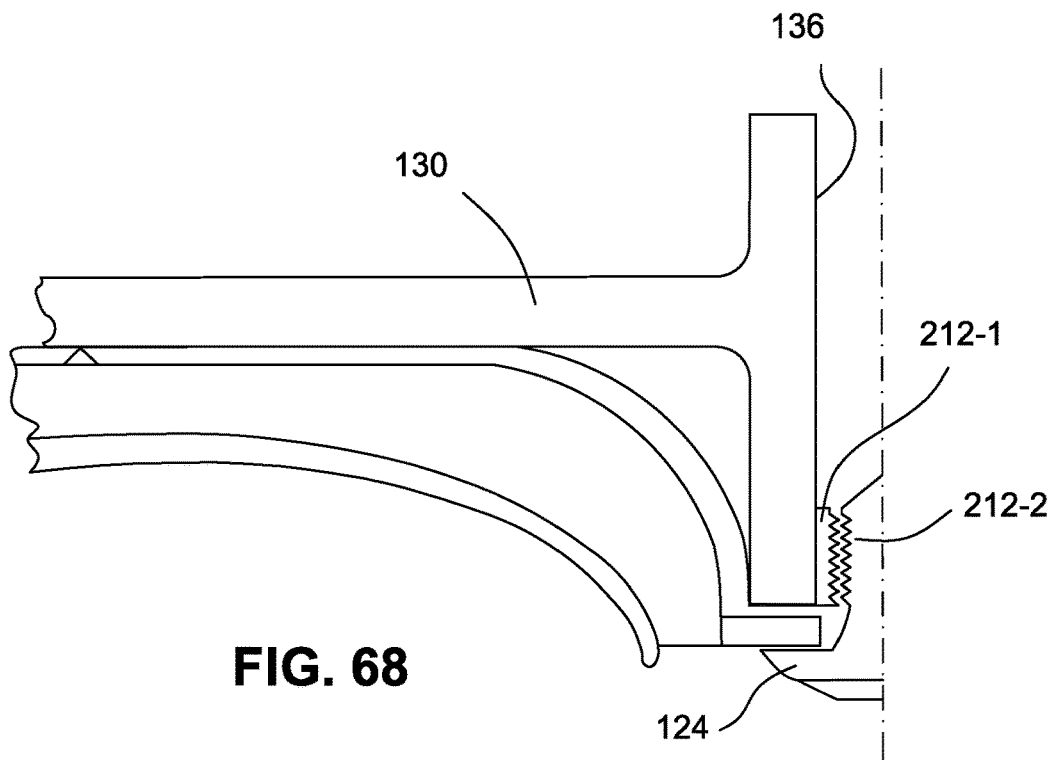
FIG. 68 is a cross-sectional view showing a bearing-housing structure coupled to the bottom cover by an integrated screw arrangement according to an example of the present technology.

In certain examples, the screw arrangement may be integrated into the bottom cover 124 and/or the bearing-housing structure 130. For example, as shown in FIG. 68, the bearing-housing structure 130 may be configured to comprise a threaded screw portion 212-1 (e.g., male screw portion) at the end of the bearing shaft 136 that is received within a corresponding threaded screw receiving portion 212-2 (e.g., female screw portion) in the bottom cover 124. Alternatively, the male screw portion may be located on the bottom cover 124 and the female screw portion on the bearing-housing structure 130. The screw portions allow the bearing-housing structure and the bottom cover to be screwed together.

Figure 70:
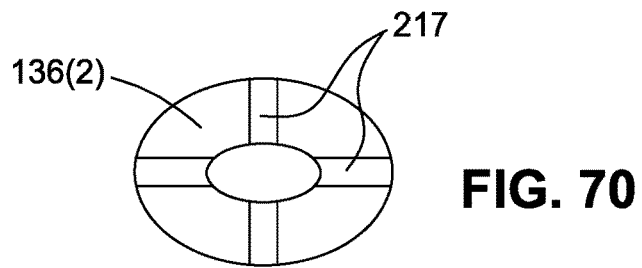
FIGS. 69 and 70 are various views of a bearing-housing structure including a reservoir and channels to retain lubricant according to an example of the present technology.
Figure 69:
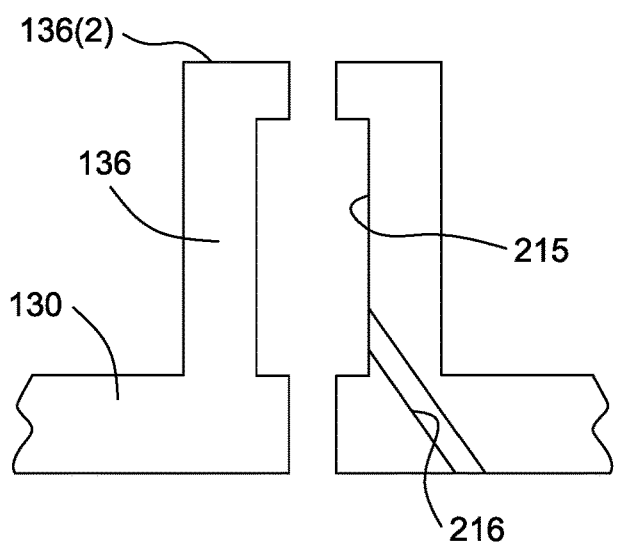
Figure 71:
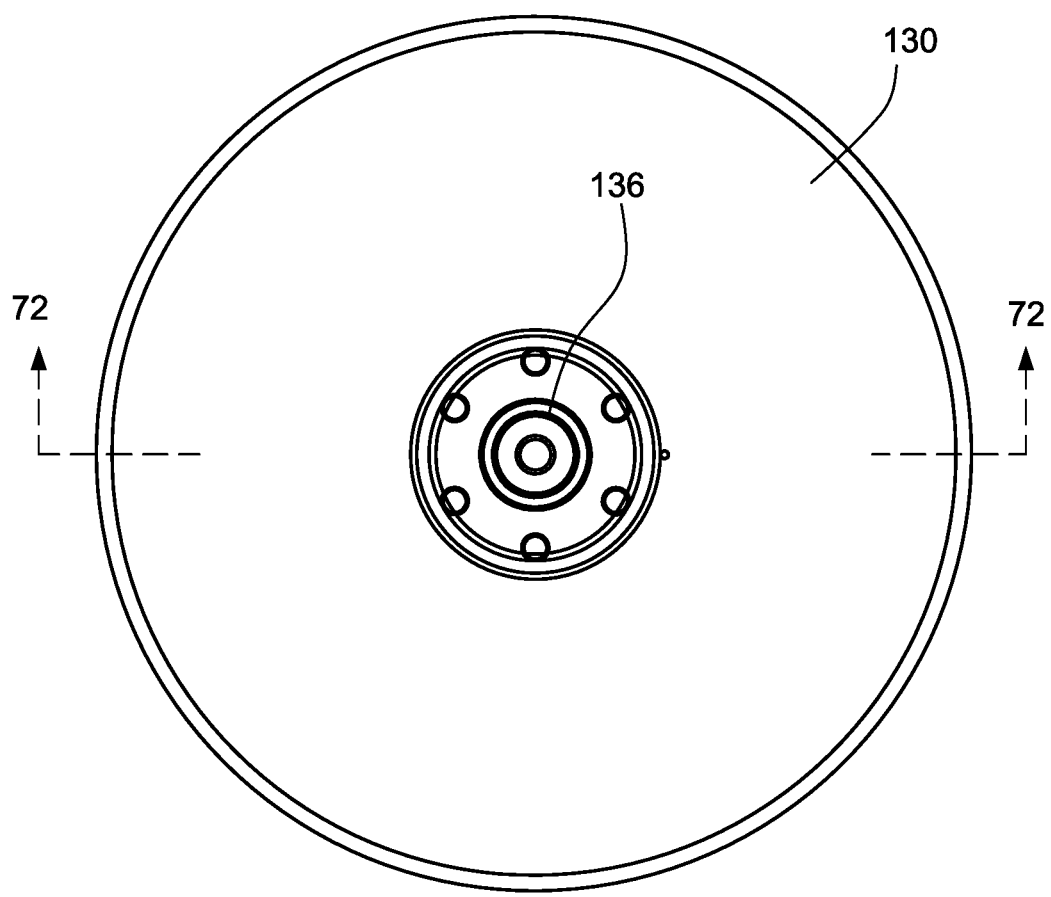
FIGS. 71 to 74 are various views of a bearing-housing structure including a lubricant reservoir according to an example of the present technology.
Figure 72:
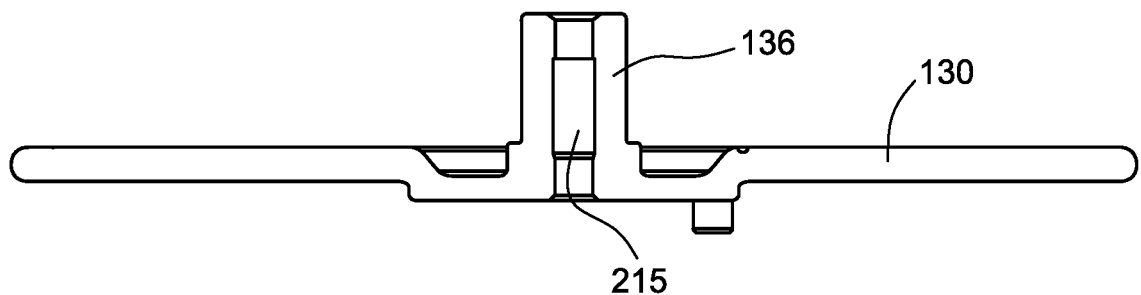

Bearing grease or lubricant is used to assist in stabilizing the rotor assembly in the bearing-housing structure. Thus, means of retaining the lubricant may be incorporated within the motor assembly. As shown in FIG. 69, a lubricant reservoir 215 may be built into the bearing shaft 136 of the bearing-housing structure 130 that is designed to supply the lubricant to the bearing thrust surface 136(2). A supply of lubricant may be fed to the reservoir 215 via an aperture 216 through the bearing-housing structure. The bearing shaft 136 may include one or more recessed channels 217 (e.g., see FIG. 70), e.g., 3-10 channels, 4-8 channels, 4-6 channels, 4, 5, or 6 channels, etc., along the bearing thrust surface 136(2) to focus pressure points at the top and/or bottom of the bearing shaft 136. The recessed channel(s) assist in retaining the lubricant at the rotating surface.

Figure 73:
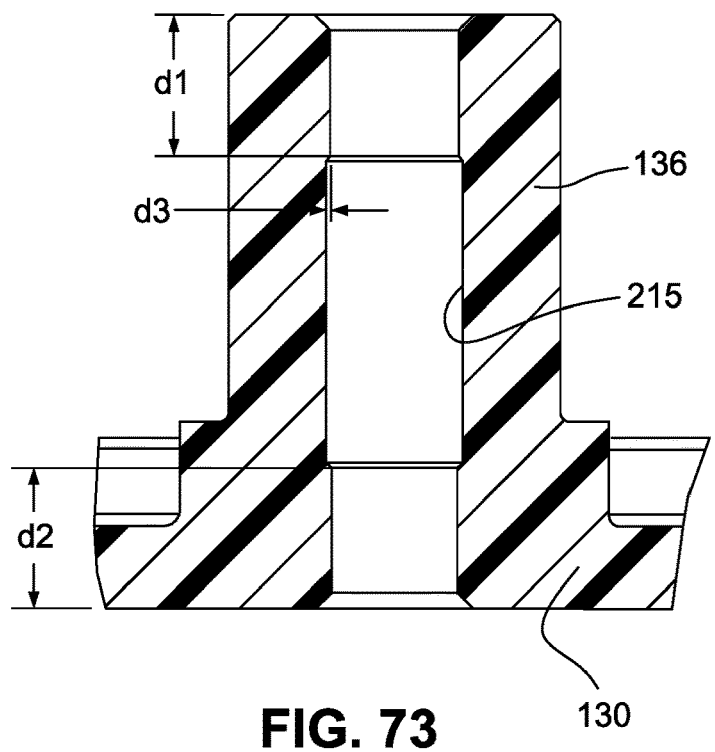
Figure 74:
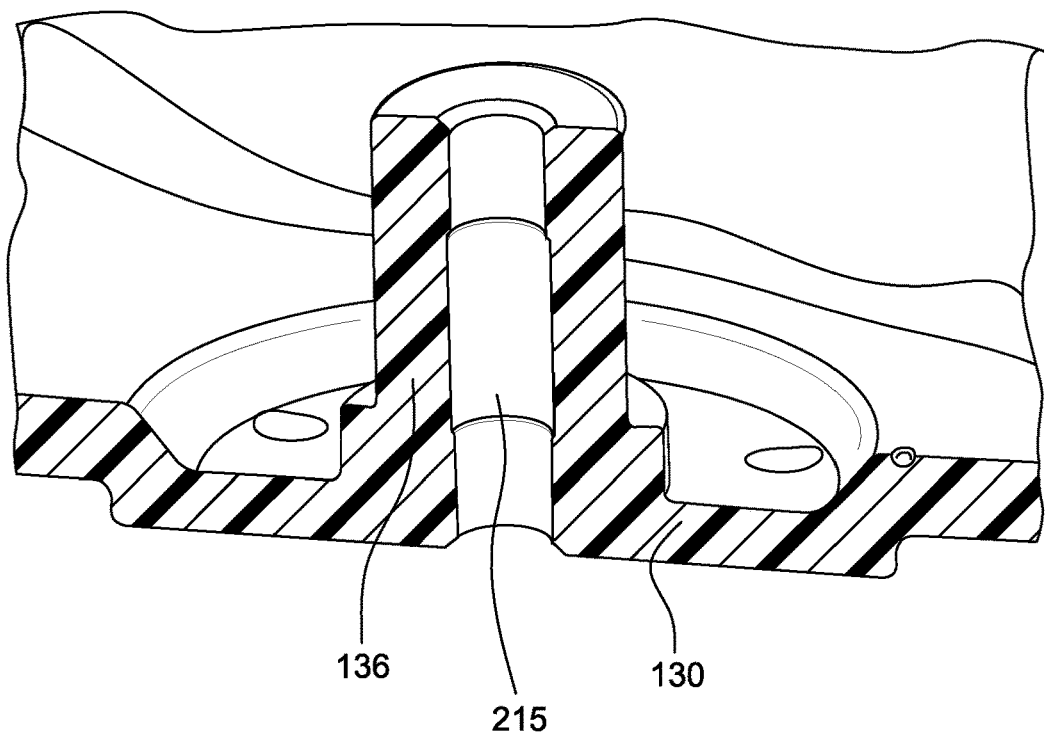
Figure 75:
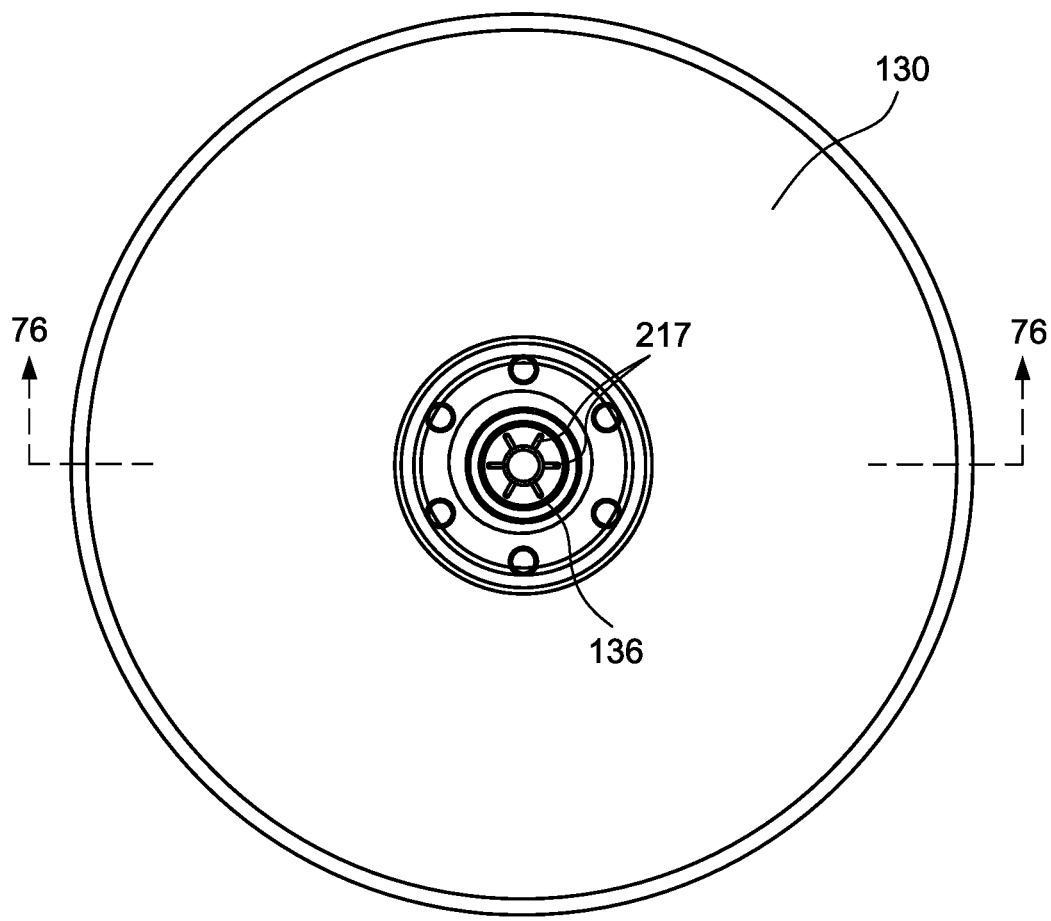
FIGS. 75 to 79 are various views of a bearing-housing structure including recessed channels for lubricant according to an example of the present technology.
Figure 76:
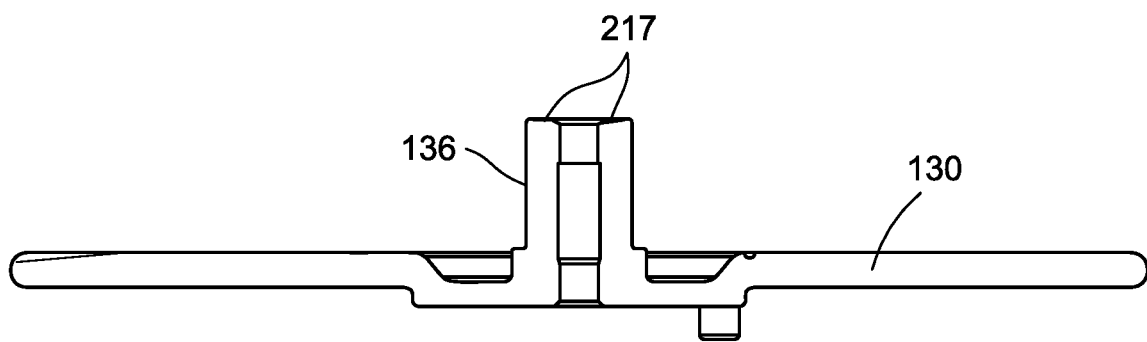

FIGS. 71 to 74 illustrate an example of a bearing-housing structure 130 including a lubricant reservoir 215 within the bearing shaft 136. In an example, as shown in FIG. 73, the lubricant reservoir 215 may be substantially centrally located within the bearing shaft 136, e.g., d1 and d2 about 1.5 to 3.0 mm, e.g., about 2.25 mm. In an example, as shown in FIG. 73, the depth d3 of the reservoir is about 0.05 to 0.1 mm, e.g., about 0.08 mm or about 0.003 inches.

Figure 77:
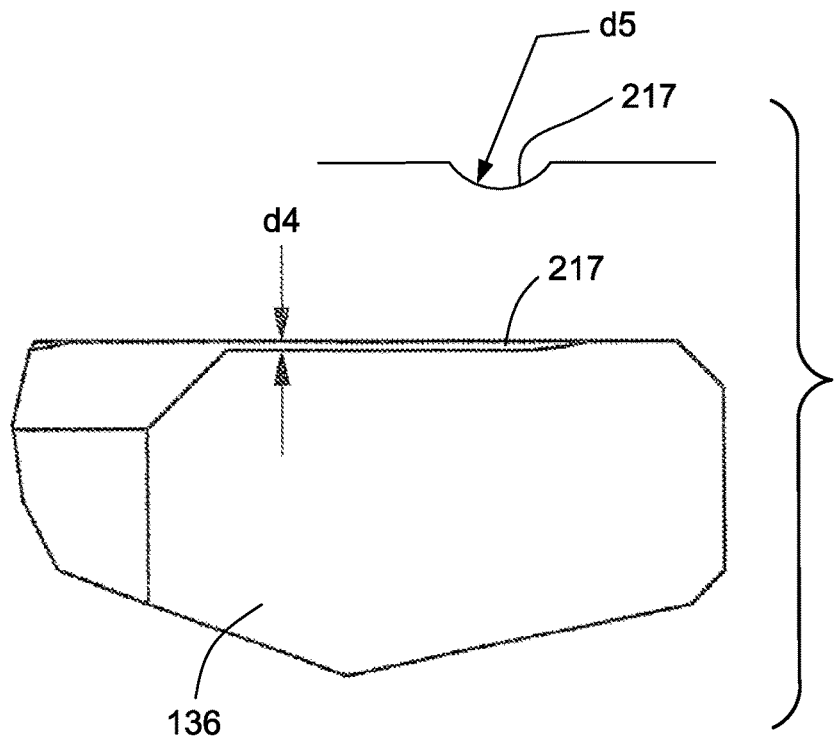
Figure 78:
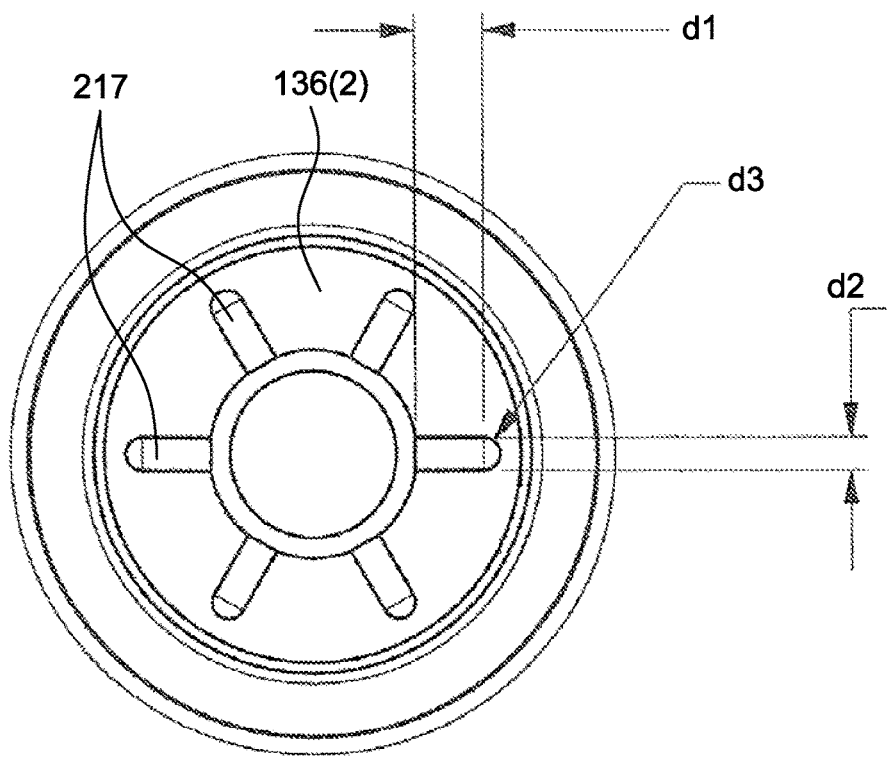
Figure 79:
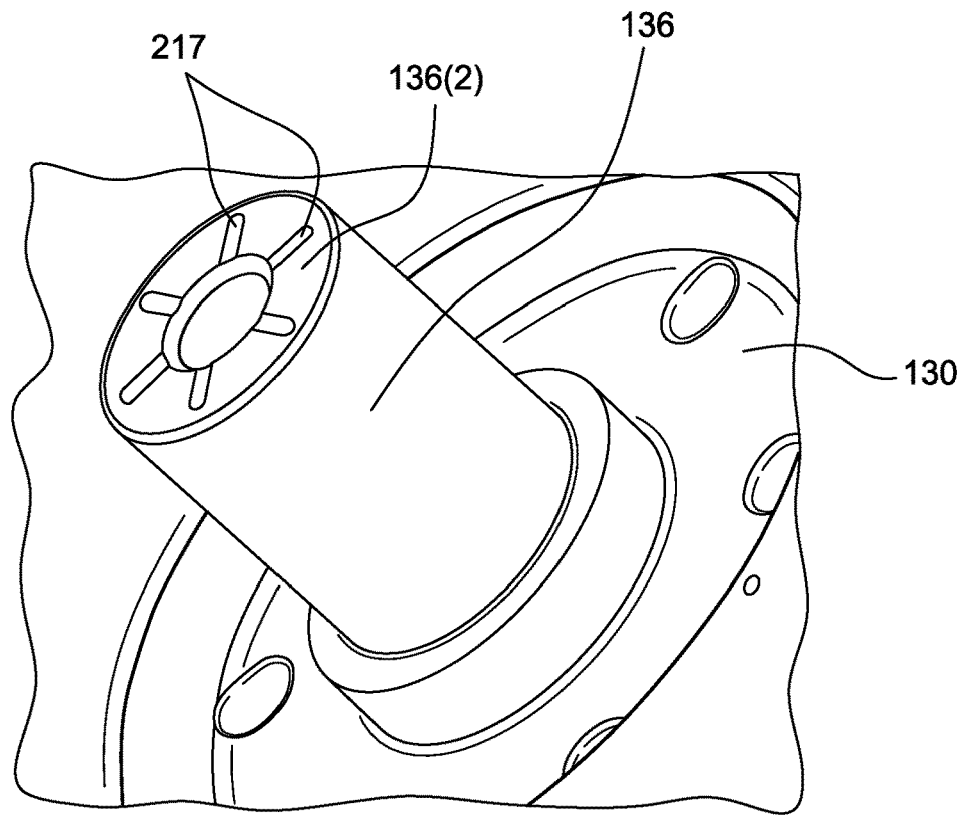
Figure 80:
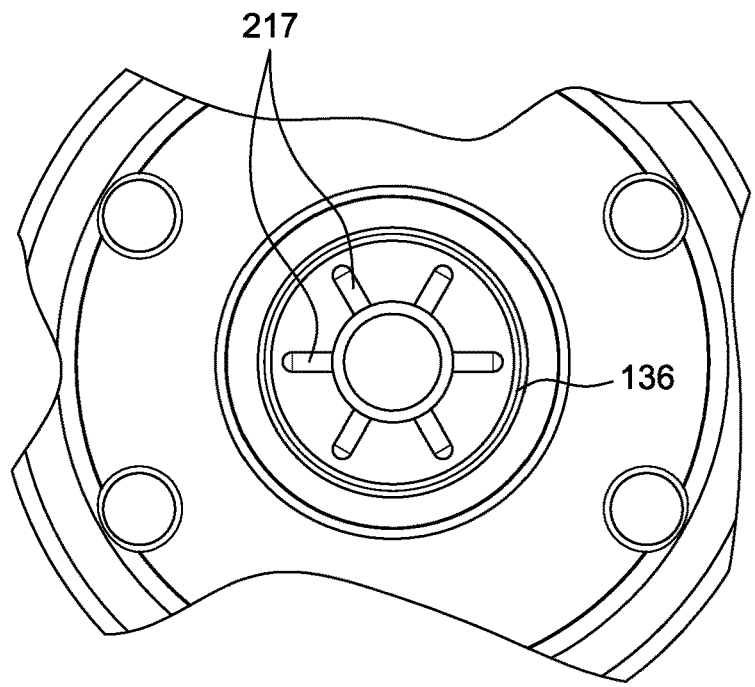
FIGS. 80 and 81 are plan views of recessed channels for a bearing-housing structure according to alternative examples of the present technology.
Figure 81:
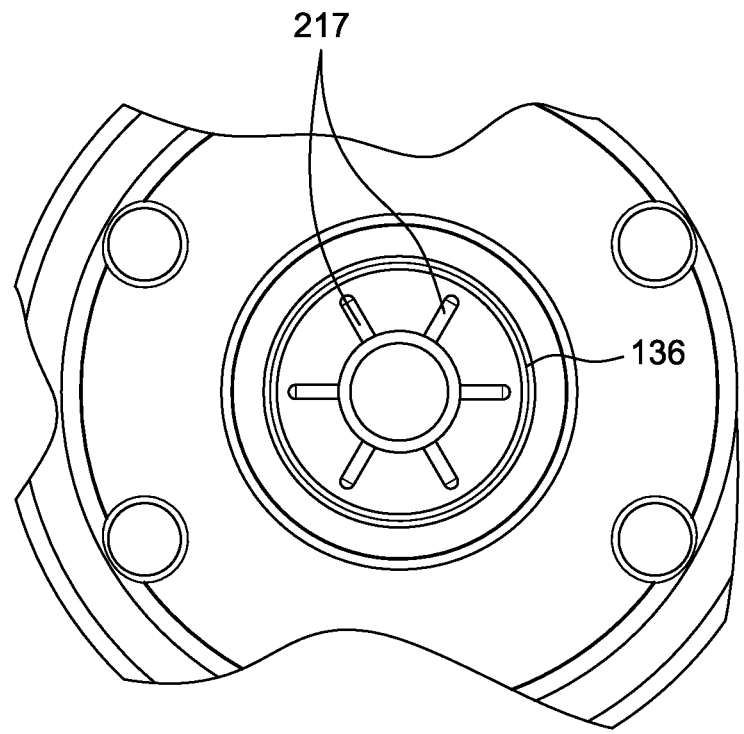

FIGS. 75 to 79 illustrate an example of a bearing-housing structure 130 including one or more recessed channels 217 (also referred to as lands) along the bearing thrust surface 136(2) of the bearing shaft 136 to assist in retaining lubricant at the rotating surface. In an example, as shown in FIGS. 77 and 78, the length d1 of each channel is about 0.5 to 1.0 mm, e.g., 0.8 mm, the width d2 of each channel is about 0.2 to 0.6 mm, e.g., 0.4 mm, the radius of curvature d3 is about 0.2 mm, the depth d4 is about 0.01 to 0.05 mm, e.g., 0.025 mm (about 0.001 inches), and the radius of curvature d5 is about 0.0155 inches. However, it should be appreciated that other suitable dimensions for the channels are possible. For example, the dimensions may be selected to adjust the hydrodynamic pressure provided by the channels, e.g., FIG. 80 shows channels 217 each having a width of about 0.016 inches and FIG. 81 shows channels 217 each having a smaller width of about 0.011 inches.

Figure 82:
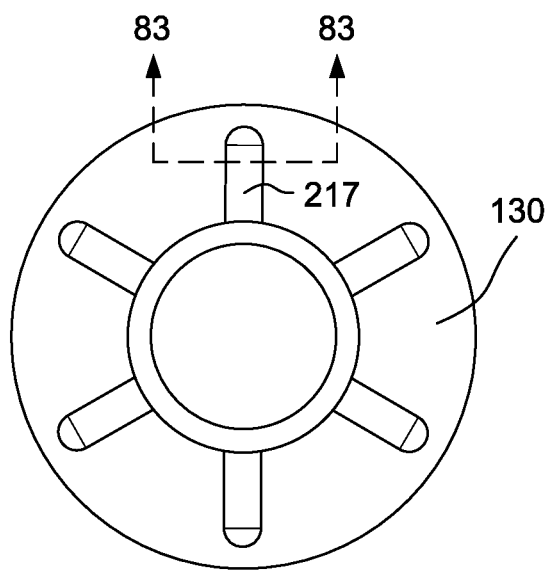
FIGS. 82 and 83 show hydrodynamic pressure concentration provided by recessed channels for a bearing-housing structure according to an example of the present technology.
Figure 83:
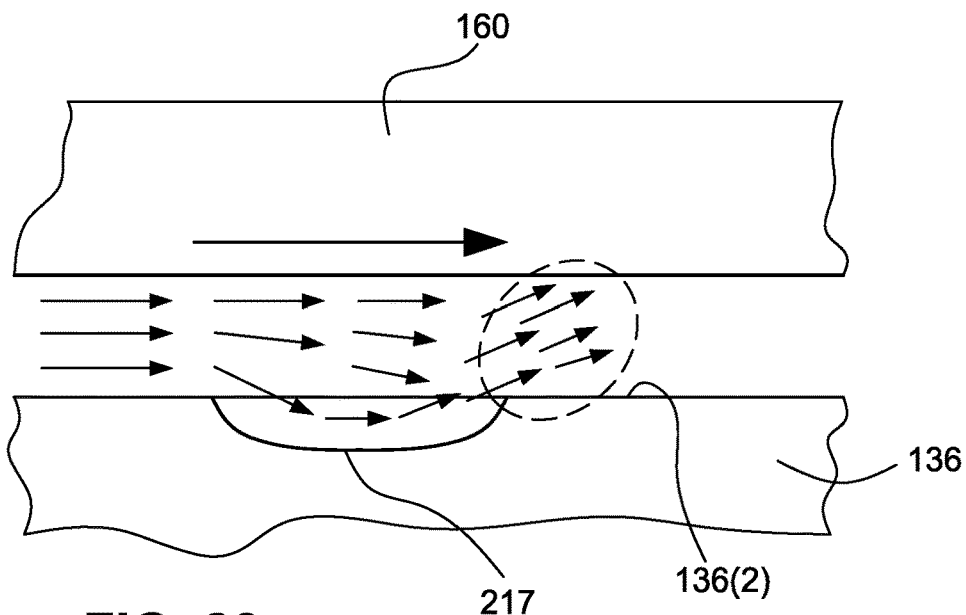
Figure 84:
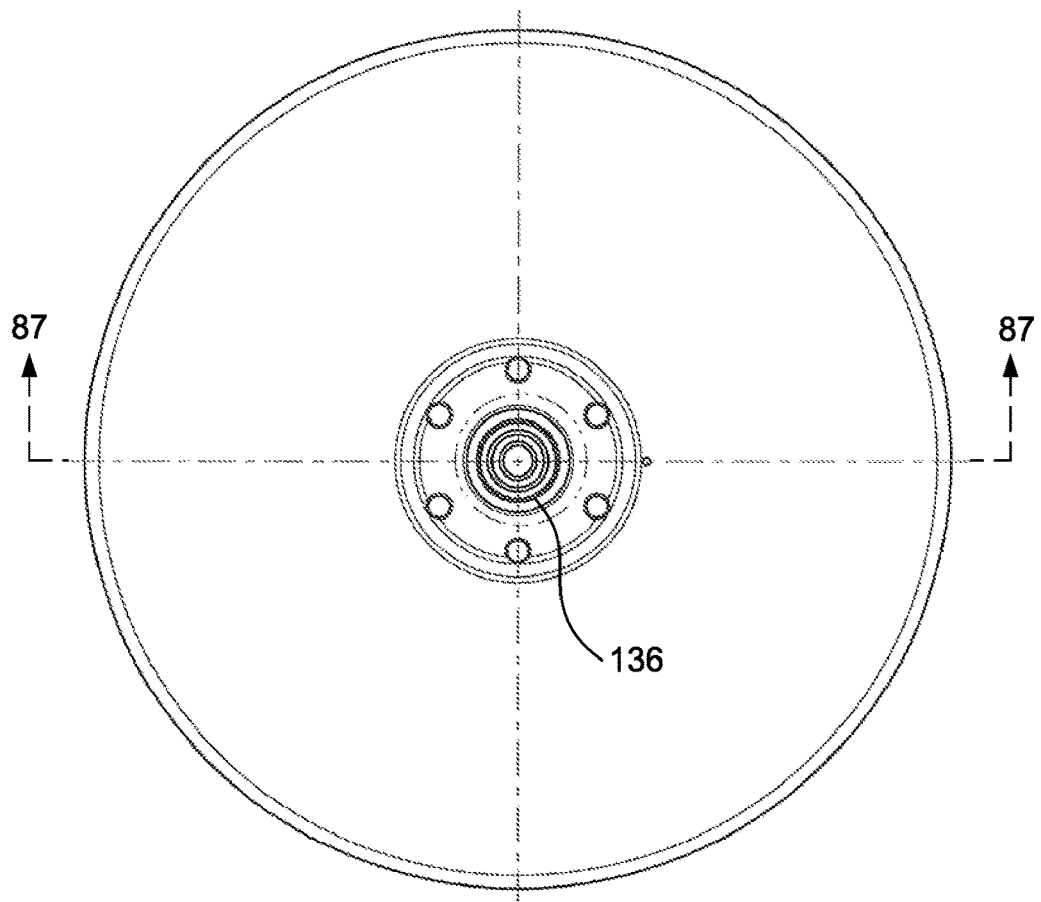
FIGS. 84 to 89 are various views of a bearing-housing structure including an annular recessed channel for lubricant according to an example of the present technology.
Figure 85:
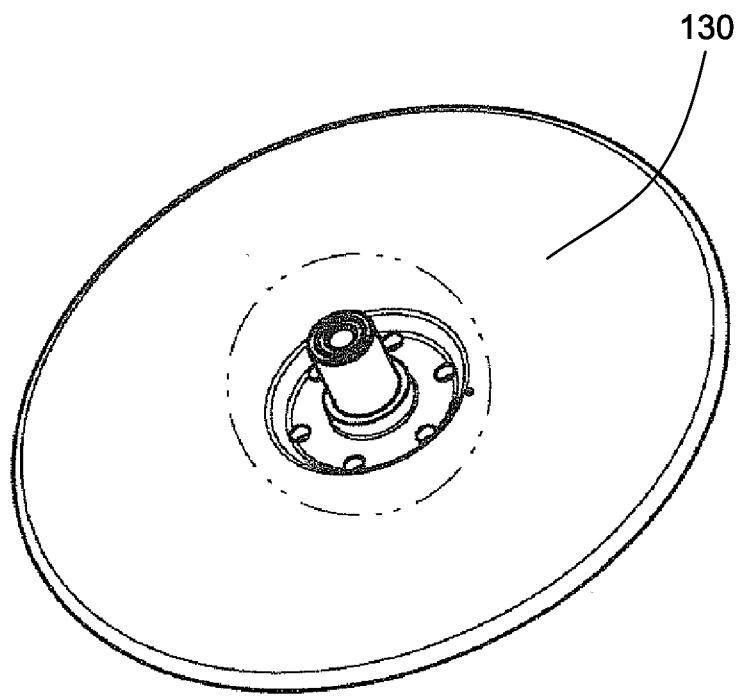
Figure 86:
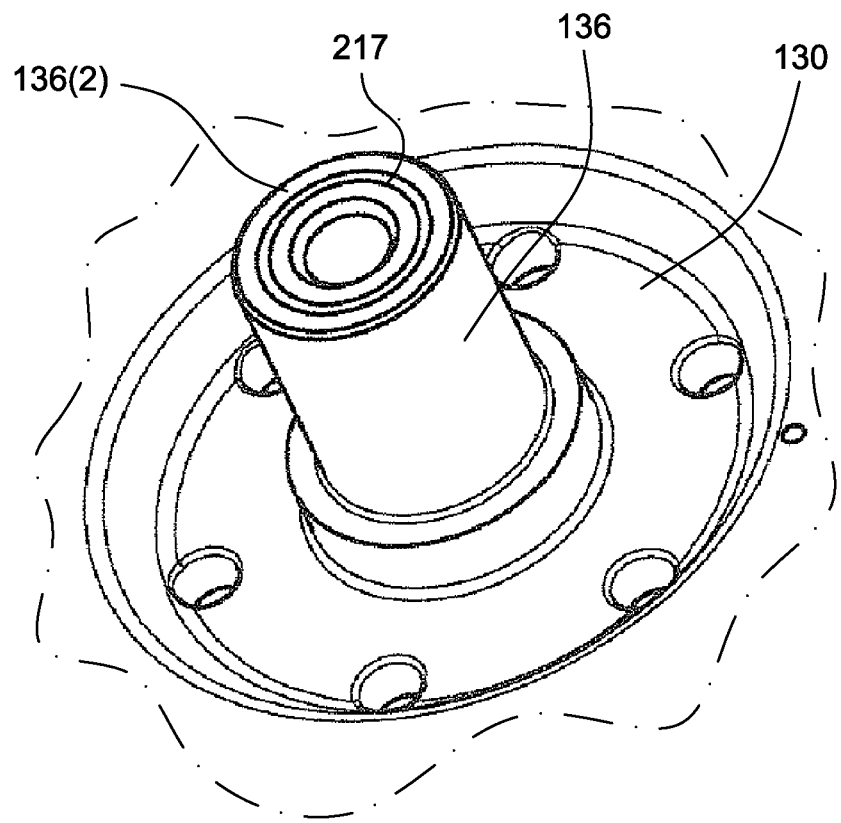
Figure 87:
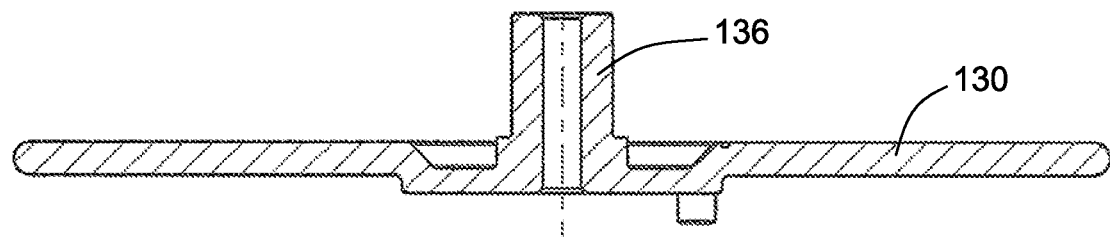

FIGS. 82 and 83 schematically illustrate the hydrodynamic pressure concentration (outlined in dashed lines) created by the channels 217 between the bearing shaft 136 and the rotor cap 160 in use.

Figure 88:
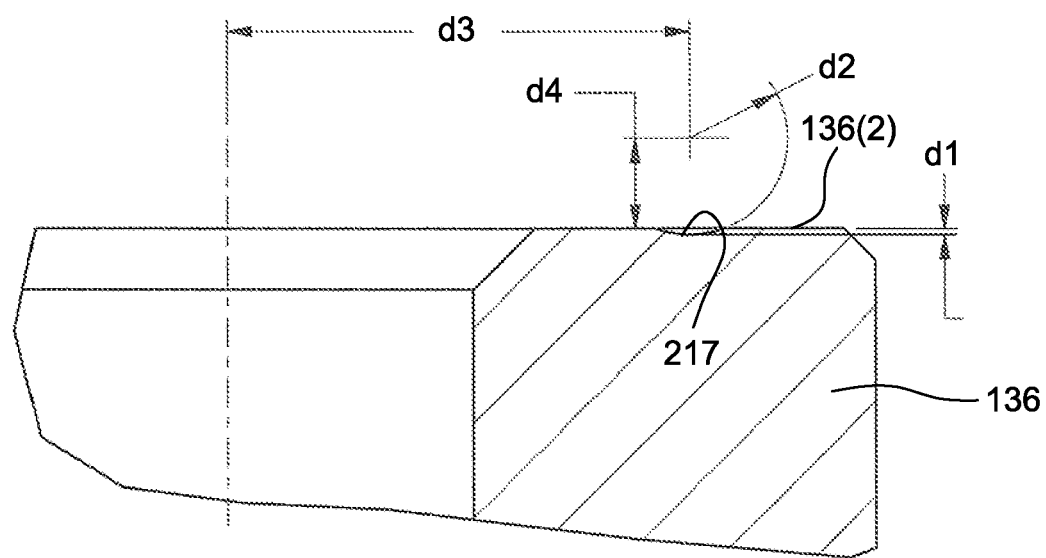
Figure 89:
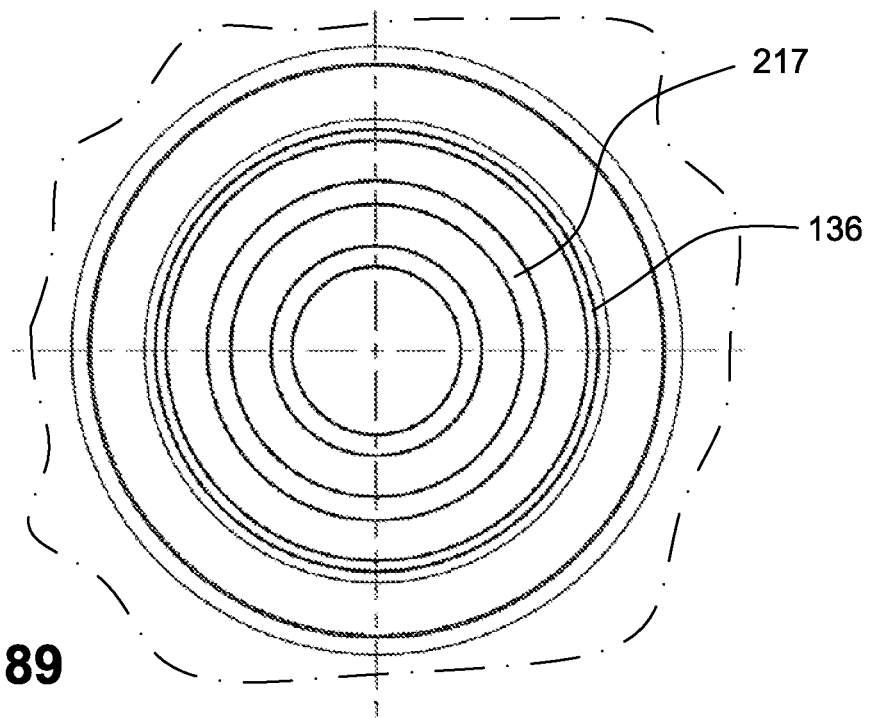

FIGS. 84 to 89 illustrate an example of a bearing-housing structure 130 including an annular recessed channel 217 along the bearing thrust surface 136(2) of the bearing shaft 136 to assist in retaining lubricant at the rotating surface. In an example, as shown in FIG. 88, the depth d1 of the channel is about 0.01 to 0.04 mm, e.g., 0.025 mm, the radius of curvature d2 is about 0.3 to 0.5 mm, e.g., about 0.4 mm, d3 is about 1.5 to 2 mm, e.g., about 1.9 mm, and d4 is about 0.25 to 0.5 mm, e.g., about 0.4 mm.

Figure 90:
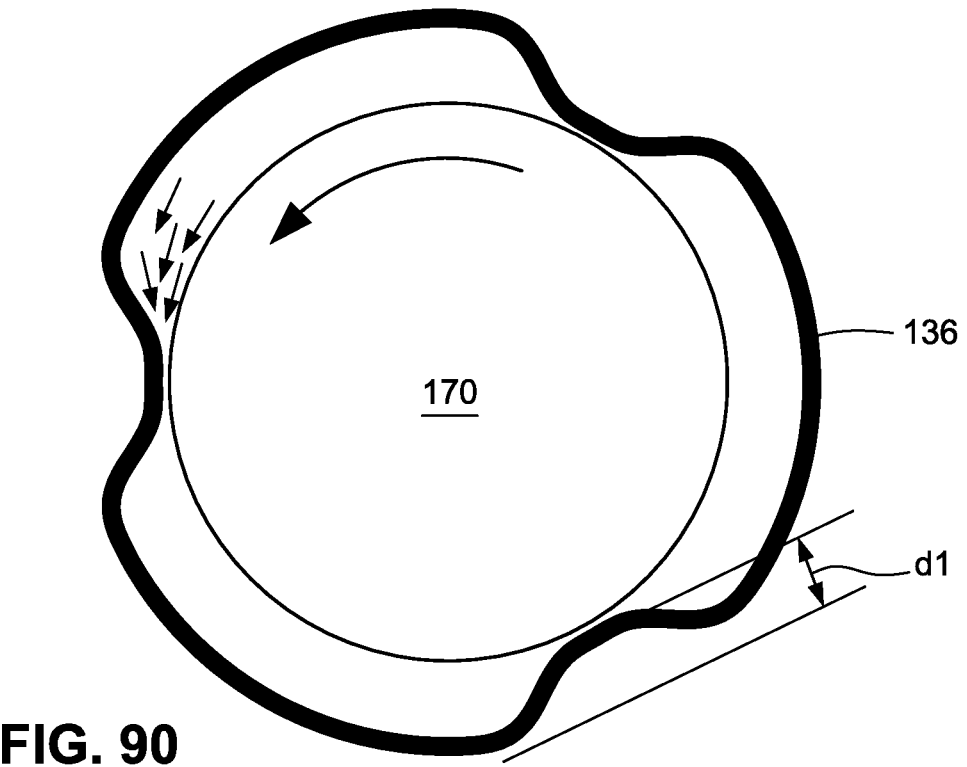
FIG. 90 is a schematic view of a bearing shaft with a trilobe configuration according to an example of the present technology.

Preferably, the bearing shaft or sleeve has a trilobe configuration rather than a circular configuration. For example, FIG. 90 shows an example of a bearing shaft with a trilobe configuration with respect to the rotor 170 in use. Each "lobe" increases the fluid dynamic or hydrodynamic pressure. In an example, the depth d1 of each lobe is about 0.0001 to 0.0005 inches.

Figure 91:
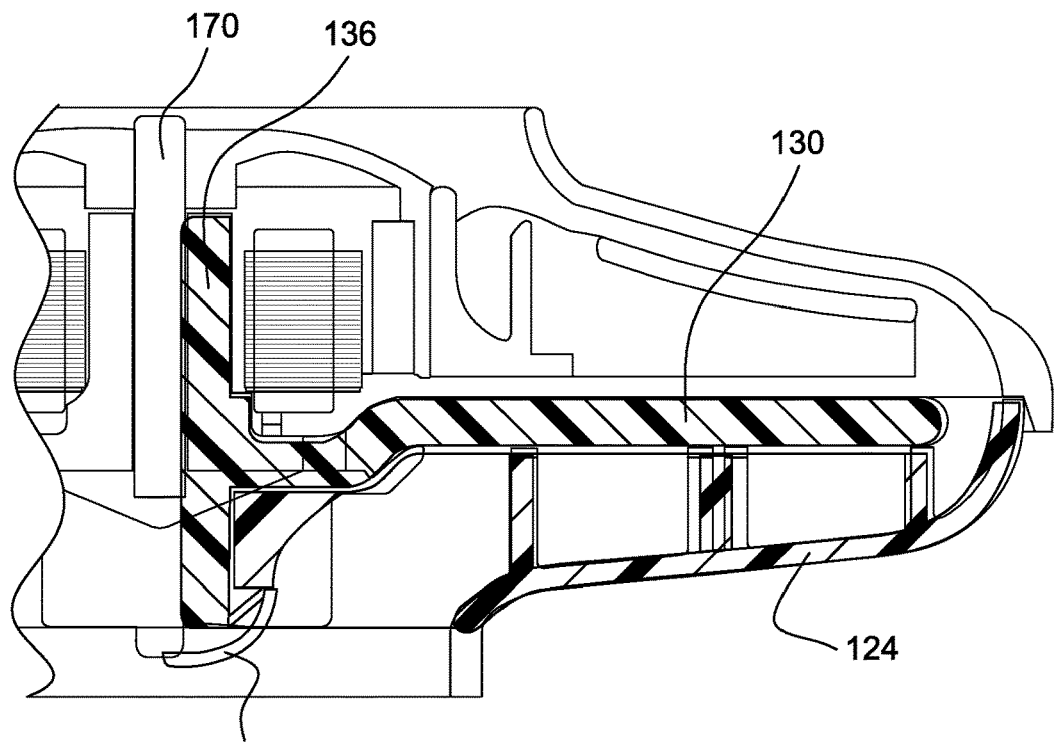
FIG. 91 is a cross-sectional view of a blower including a retaining ring to retain lubricant according to an example of the present technology.

In certain examples, as shown in FIG. 91, a retaining ring 218, such as an acorn shaped grooveless retaining ring, may be coupled to the bottom of the bearing shaft 136 to assist in retaining the lubricant around the bearing-housing structure 130.

Figure 92:
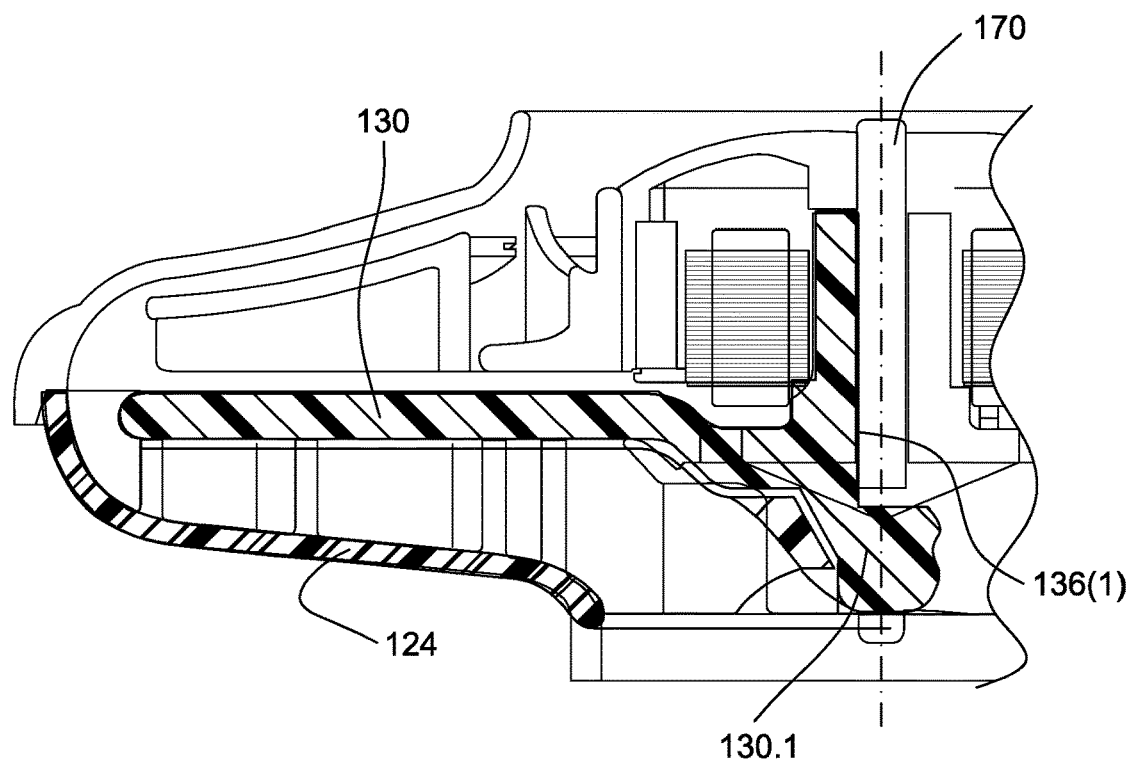
FIG. 92 is a cross-sectional view of a blower including a bearing-housing structure having structure to retain lubricant according to an example of the present technology.

In certain examples, as shown in FIG. 92, the bearing-housing structure 130 may be closed at one end, such as the lower end 130.1, of the radial bearing portion 136(1) to retain the lubricant within the bearing shaft.

The grease or lubricant may include a Kyoto Ushi Multem or other such lubricants. Alternatively, the bearing may be a dry bearing, i.e., the bearing-housing and/or rotating components are formed at least in part or coated with a low friction material such as a low coefficient of friction material, e.g., a ceramic based coating, a nickel based coating, Teflon™ or graphite, that provides lubricity and eliminates the requirement for a grease or lubricant.

Bearing Cartridge

In an alternative example, as shown in FIGS. 109-110 and 125-127, the bearing shaft of the bearing-housing structure may be replaced with a bearing cartridge 390 including bearings 394, 395 adapted to rotatably support the rotor 370.

Figure 112:
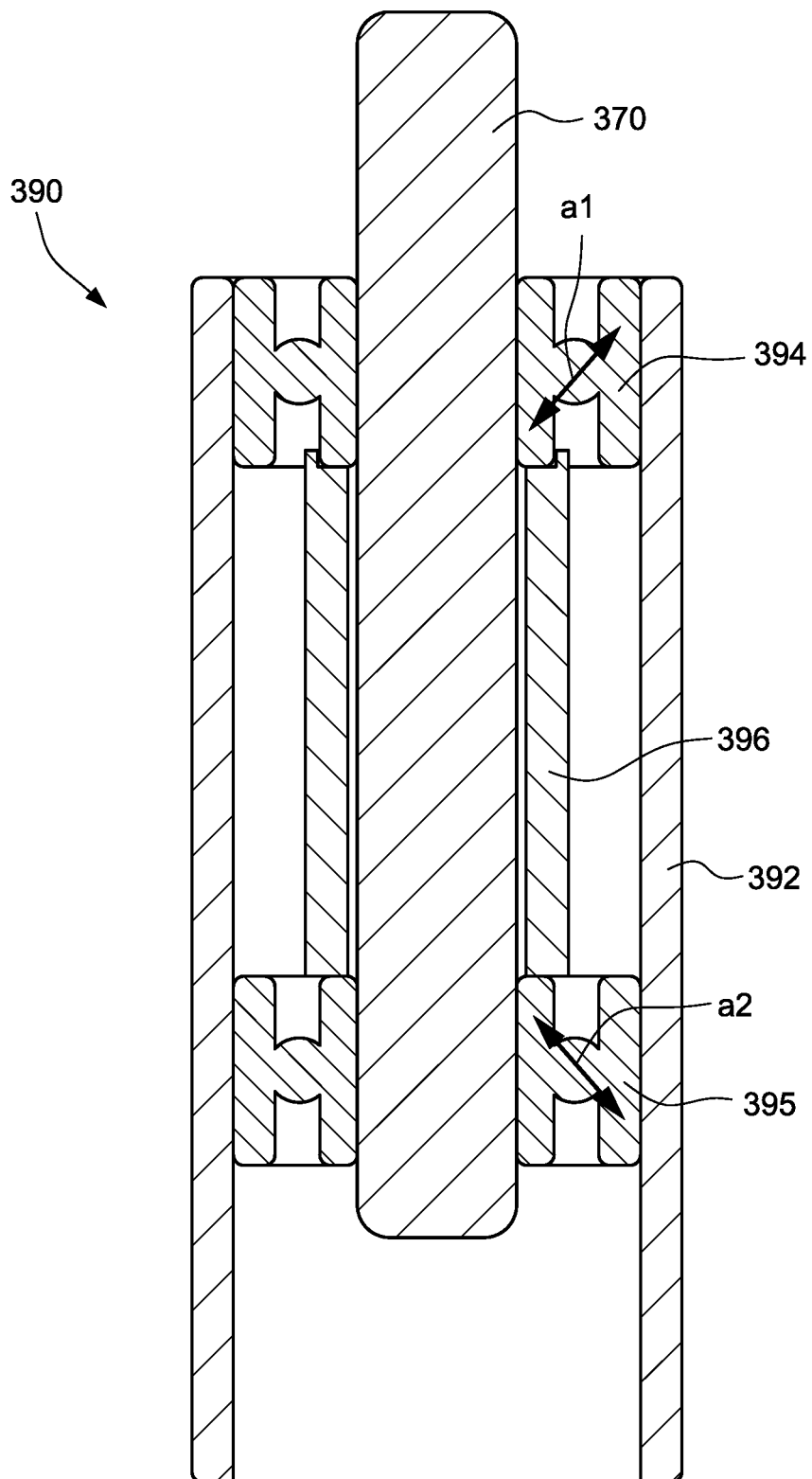
FIG. 112 is a cross-sectional view of a bearing cartridge according to an example of the present technology.

As illustrated, the bearing cartridge 390 includes a tubular sleeve or cartridge 392, two spaced-apart bearings 394, 395 supported within the sleeve 392, and a spacer 396 (which may be optional) between the bearings to provide a preload (e.g., direction of preload shown by arrows a1 and a2 in FIG. 112). Each bearing 394, 395 includes an outer race engaged with the interior surface of the sleeve 392 and an inner race engaged with the rotor 370, e.g., bonded using an adhesive. FIG. 112 is an isolated view of the bearing cartridge 390.

In this example, the bearing-housing structure 330 (e.g., injection molded of plastic material) includes a housing part providing a base 332 and an annular flange or disk 334 extending from the base 332. The base 332 provides a tube portion 333 that supports an end of the bearing cartridge 390, e.g., an exterior surface of the sleeve 392 of the bearing cartridge 390 is bonded in the tube portion 333, e.g., using adhesive. Also, the stator component 345 is provided (e.g., bonded using an adhesive) along the exterior surface of the sleeve 392.

Figure 109:
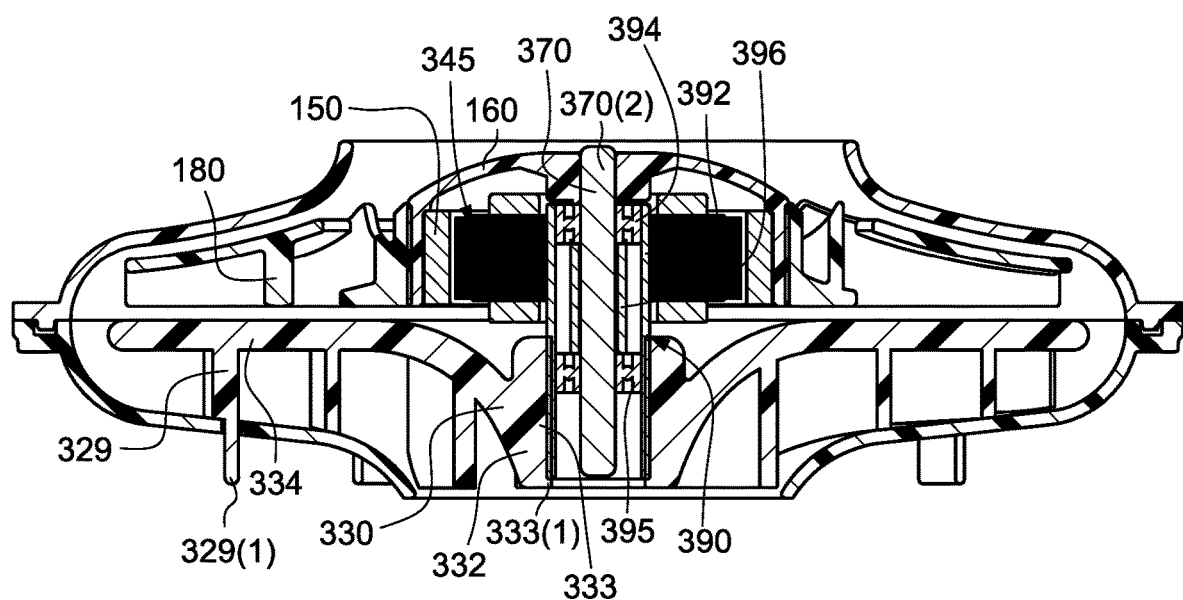
FIG. 109 is a cross-sectional view of a blower according to another example of the present technology.
Figure 110:
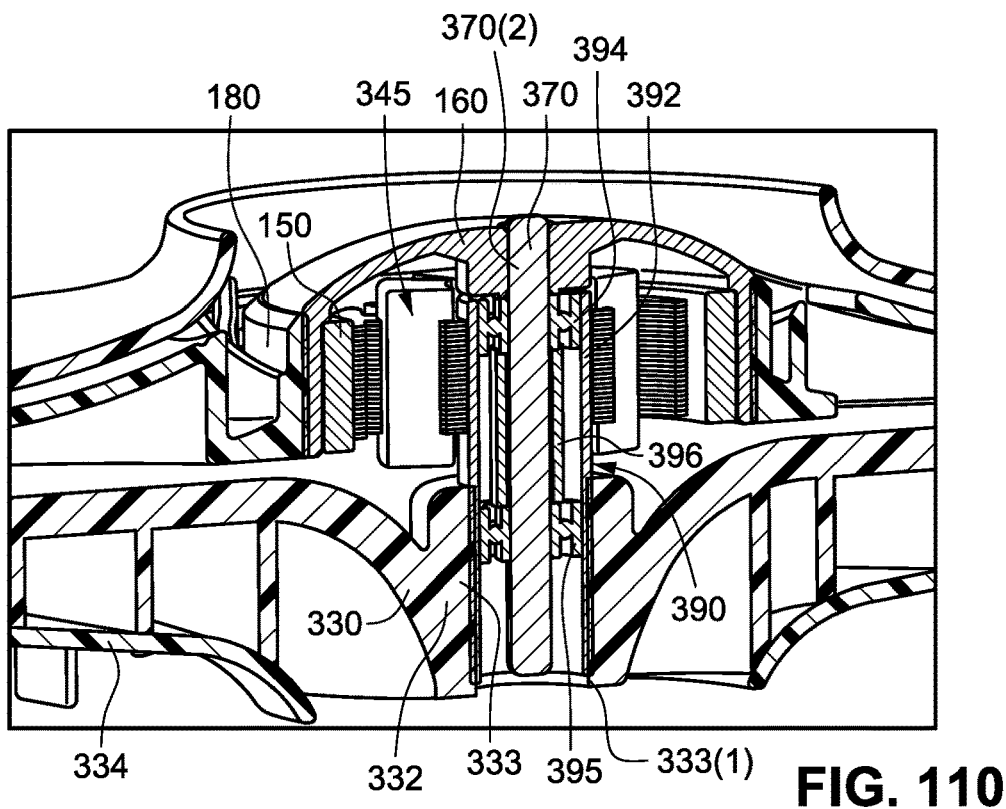
FIG. 110 is an enlarged cross-sectional view of a portion of the blower of FIG. 109.
Figure 111:
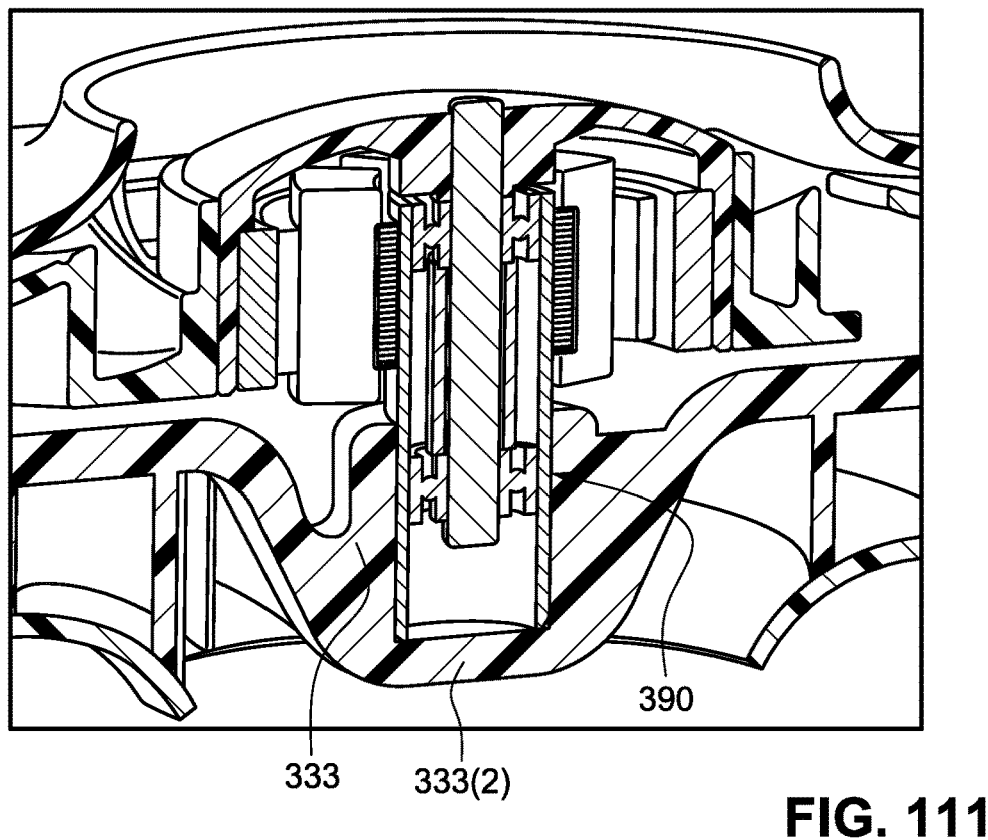
FIG. 111 is a cross-sectional view of a portion of a blower according to another example of the present technology.

In FIGS. 109 and 110, the tube portion 333 is open ended and provides a flange 333(1) along the opening to provide a stop surface for supporting the bearing cartridge 390 within the tube portion 333. In an example, such opening at the bottom of the tube portion may be capped or sealed off. In an alternative example, as shown in FIG. 111, the bottom of the tube portion 333 may be closed by an integral lower wall 333(2) to provide the stop surface for supporting the bearing cartridge 390 within the tube portion 333.

In this example, as shown in 109, 126, and 127, stator vanes 329 of the bearing-housing structure 330 provide tabs 329(1) that are adapted to engage within respective openings 324(1) in the bottom cover 324 (e.g., with a snap-fit, heatstake) to retain and align the bearing-housing structure 330 with respect to the bottom cover 324. The top cover 322 may be secured to the bottom cover 324, e.g., by adhesive or ultrasonic welding or using other known methods.

As described above, the rotor cap 160 (supporting the magnet 150 and impeller 180) is provided to the end portion 370(2) of the rotor 370. In an example, the magnet may be centered on the stator assembly to remove magnetic preload or thrust from the rotor cap to the bearing cartridge.

In an example, the rotor cap 160 may be provided to the rotor 370 (e.g., press-fit) in a first assembly operation, and then the rotor 370 (with the rotor cap attached thereto) may be provided to the bearing cartridge 390 in a second assembly operation. Such assembly may impart less damage to the bearings of the bearing cartridge.

In an alternative example, the bearing cartridge may include a single bearing adapted to cooperate with another bearing supported in the housing for rotatably supporting the rotor.

In another alternative example, an air bearing arrangement may be provided to support the rotor.

Tangential Outlet

In an example, the blower may include an axial aligned inlet and an outlet that is tangential to the inlet or tangential to the direction of rotation of the impeller.

For example, FIGS. 128 to 131 show a blower 800 including a top cover 822 providing an inlet 823 and a bottom cover 824 providing an outlet 825 that is tangential to the inlet 823. Similar to examples described above, the blower includes a bearing-housing structure 830 structured to support a bearing cartridge 890 adapted to rotatably support the rotor 870. The rotor cap 860 (supporting the magnet 850 and impeller 880) is provided to an end portion of the rotor 870.

In this example, the bearing-housing structure 830 includes an annular side wall 835 that extends downwardly from an end portion of the disk 834. The free end of the side wall 835 provides tabs 835(1) that are adapted to engage within respective openings in the bottom cover 824 (e.g., with a snap-fit, heat stake, ultrasonic weld) to retain and align the bearing-housing structure 830 with respect to the bottom cover 824.

The side wall 835 along with the covers 822, 824 define a volute 837 for directing air towards the outlet 825. In this example, the volute 837 expands in cross-sectional area towards the outlet to generate pressure via static regain. The side wall 835 and bottom cover 824 also provide an open space 839 out of the air flow path, e.g., for electronic components such as a PCB or driver.

FIGS. 132-138 show another example of a blower including an outlet that is tangential to the inlet. In this example, the blower 900 includes a bearing-housing structure that is incorporated into or otherwise provided by the blower housing 920.

As illustrated, the blower housing 920 includes a top cover 922 providing an inlet 923 and a bottom cover 924 that cooperates with the top cover 922 to provide an outlet 925 that is tangential to the inlet 923.

The bottom cover 924 is also structured to support the bearing cartridge 990 and define the volute 937 for directing air towards the outlet 925. Specifically, the bottom cover 924 includes a base 932 providing a tube portion 933 that supports the bearing cartridge 990 and an annular flange or disk 934 that curves upwardly and then extends radially outwardly from the base 932. An annular side wall 935 extends downwardly from an edge of the disk 934 to define the volute 937. The rotor cap 960 (supporting the magnet 950 and impeller 980) is provided to an end portion of the rotor 970 rotatably supported by the bearing cartridge 990.

Figure 136:
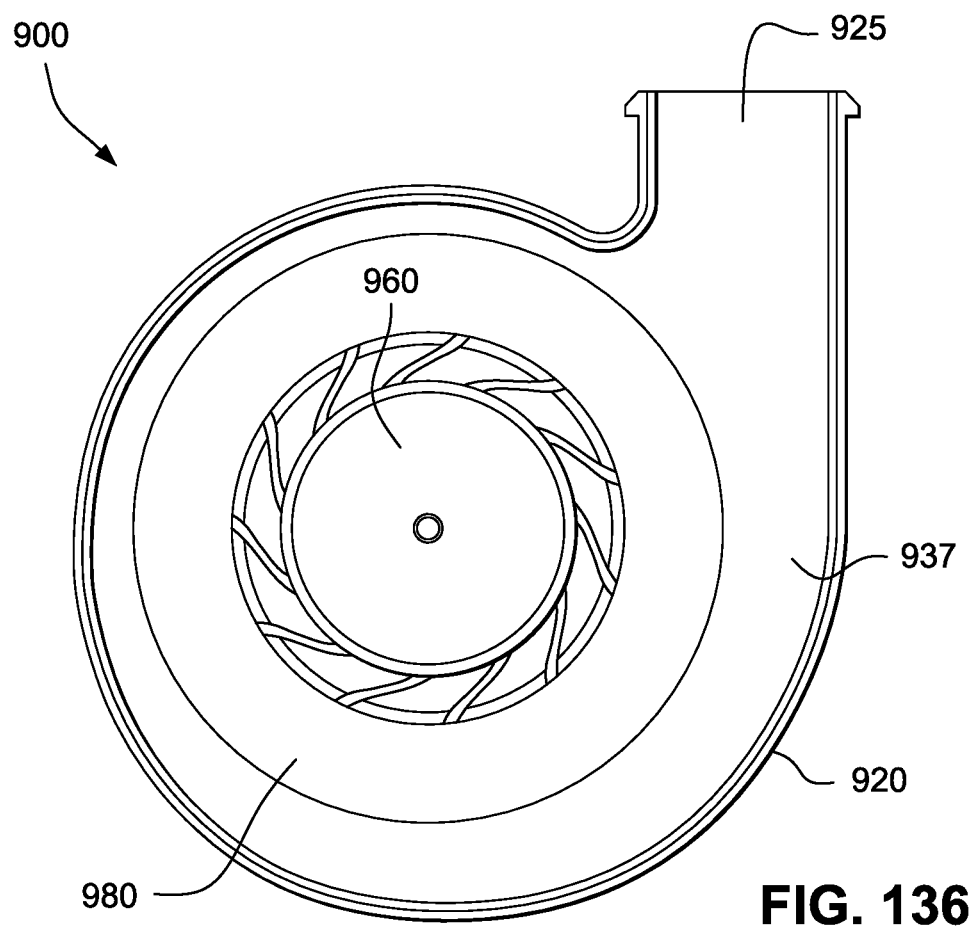
Figure 137:
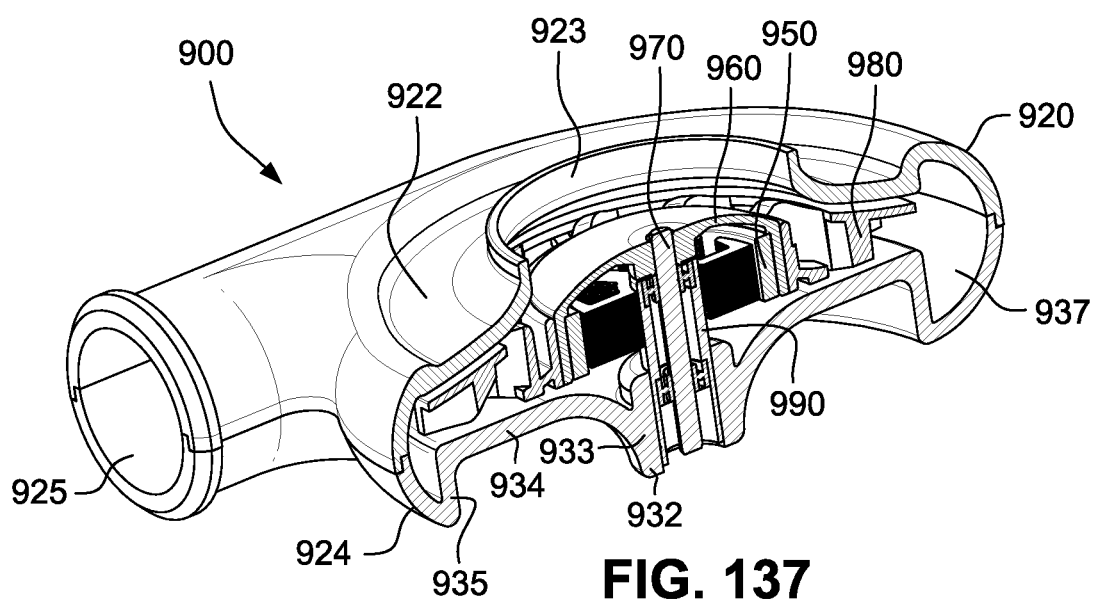
Figure 138:
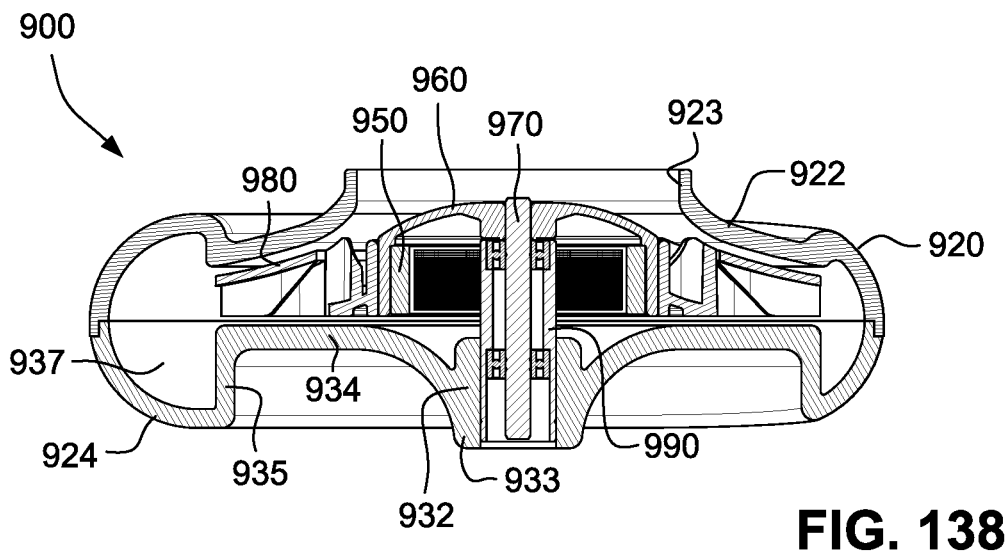
Figure 139:
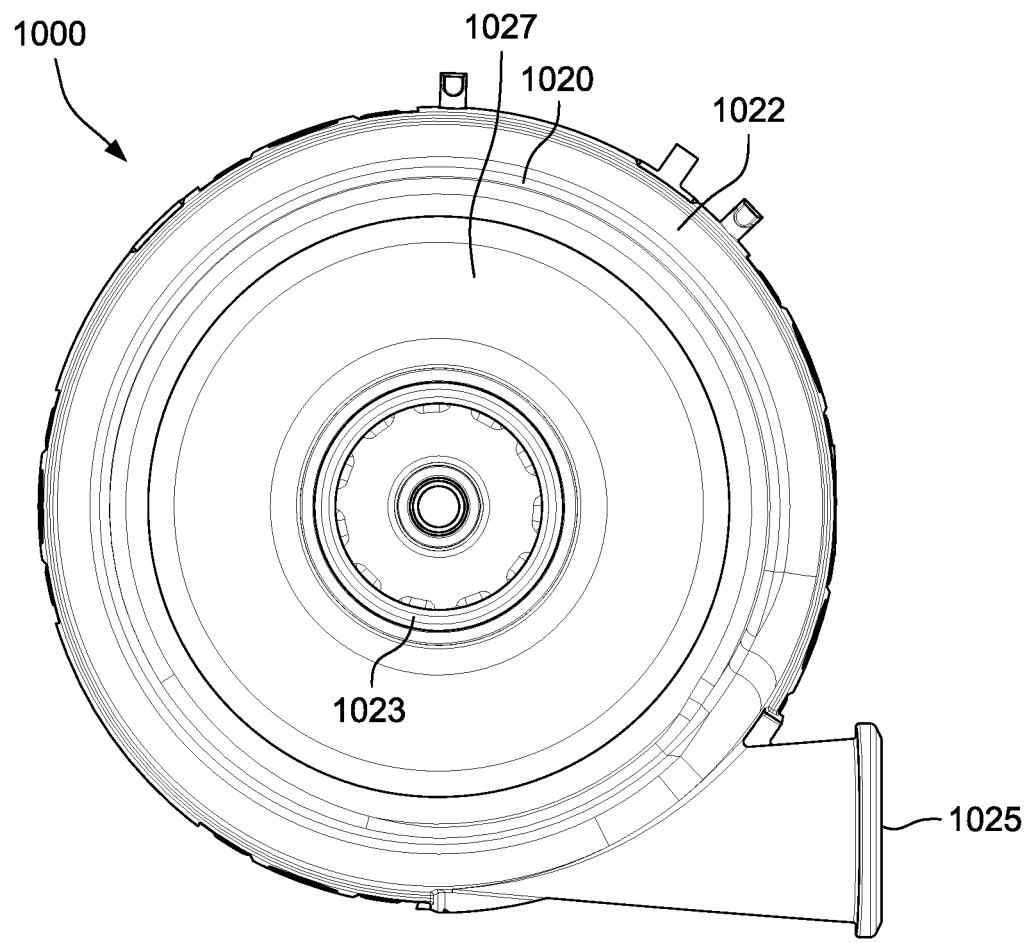
FIGS. 139 to 142 show various views of a blower according to another example of the present technology.
Figure 140:
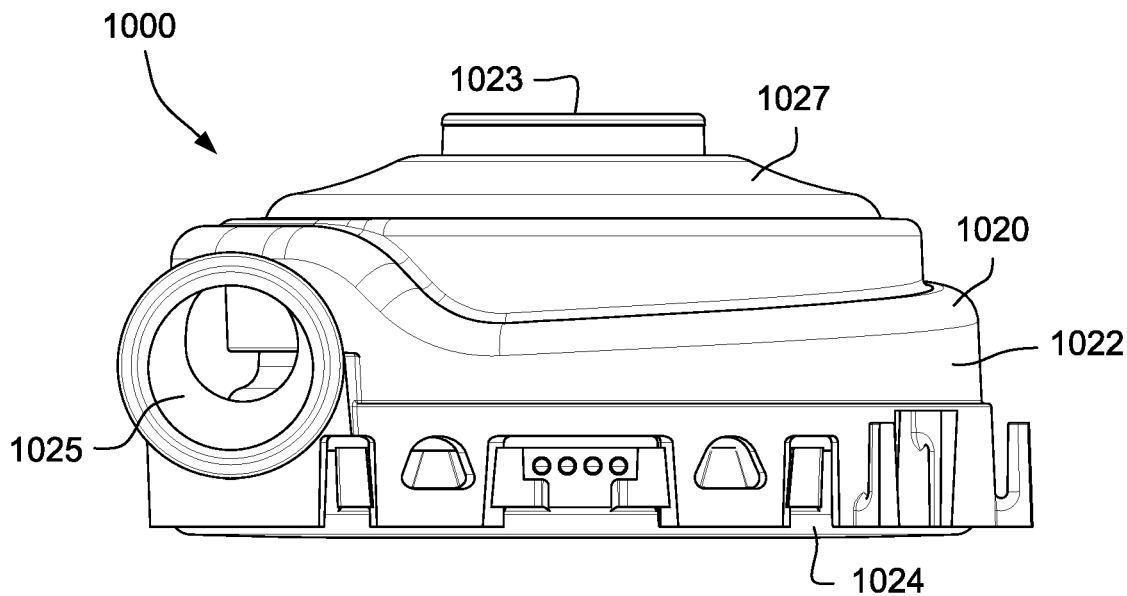
Figure 141:
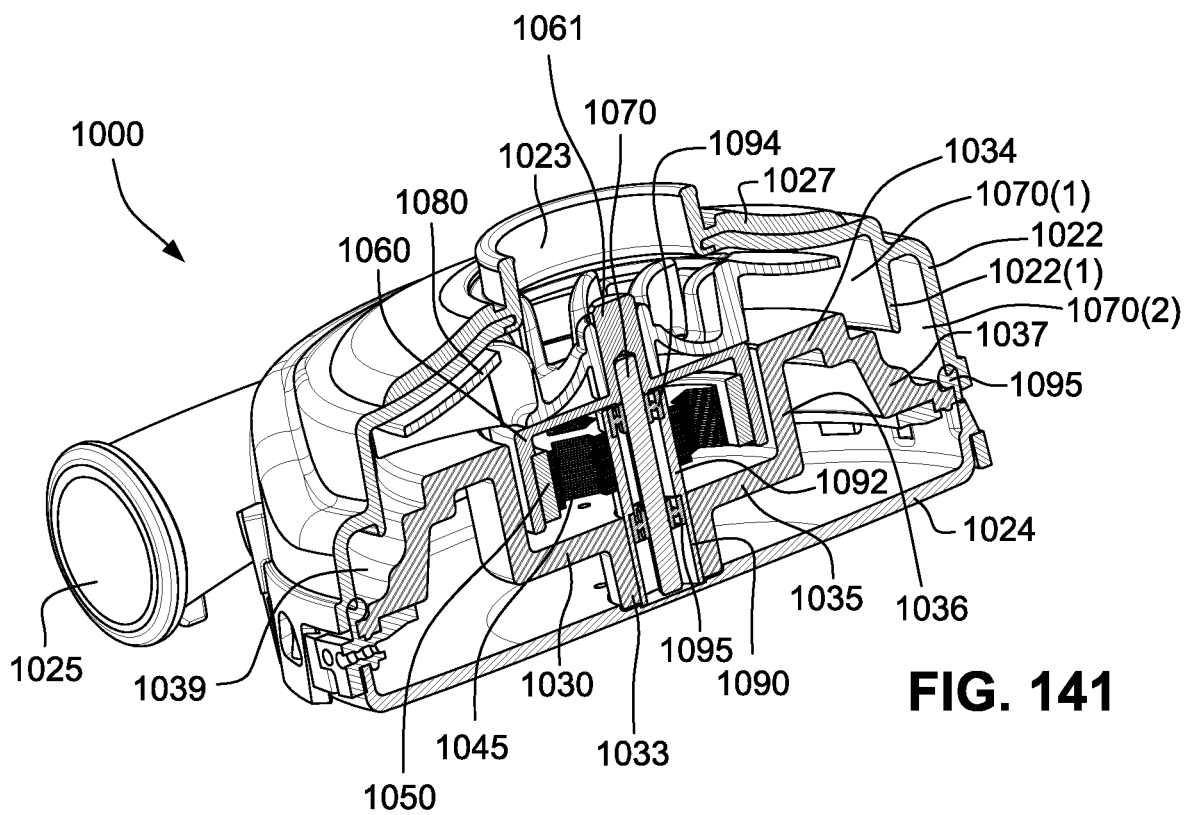
Figure 142:
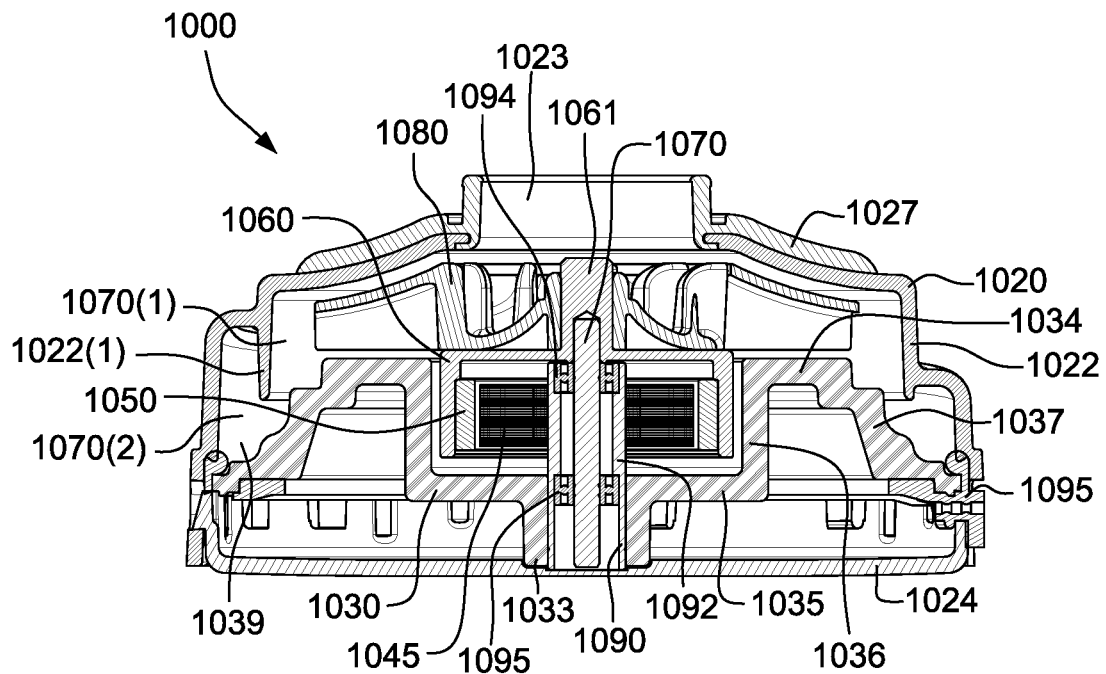

In this example, the volute 937 expands in cross-sectional area towards the outlet to generate pressure via static regain, e.g., see FIG. 136. In the illustrated example, the volute includes a generally semi-circular cross-section configuration, e.g., see FIGS. 137 and 138, however other suitable volute shapes are possible.

FIGS. 139 to 142 show another example of a blower including an outlet that is tangential to the inlet. The blower 1000 includes housing 1020 having a top cover 1022 and a bottom cover 1024. The top cover 1022 provides the inlet 1023 and also provides the outlet 1025 that is tangential to the inlet 1023. In this example, a chimney or inlet tube portion 1027 is provided to the inlet 1023.

A bearing-housing structure or stationary component 1030 is provided to the housing 1020 and is structured to support a bearing cartridge 1090 and define a volute 1039 for directing air towards the outlet 1025.

The bearing-housing structure 1030 includes a tube portion 1033 that supports the bearing cartridge 1090, outwardly and upwardly extending wall portions 1035, 1036 that defines a recess to receive motor components, an annular flange or disk 1034, and a downwardly and outwardly extending end portion 1037 extending from the disk.

The tube portion 1033 supports an end of the bearing cartridge 1090, e.g., an exterior surface of the sleeve 1092 of the bearing cartridge 1090 is bonded in the tube portion 1033, e.g., using adhesive. Also, the stator component 1045 is provided (e.g., bonded using an adhesive) along the exterior surface of the sleeve 1092.

A rotor cap 1060 (supporting the magnet 1050 and impeller 1080) is provided to the rotor 1070 rotatably supported by bearings 1094, 1095 within the bearing cartridge 1090. In this example, the magnet 1050 is provided along an interior surface of the rotor cap 1060 and a peg or pin 1061 is provided to the upper wall of the rotor cap to retain the impeller 1080. In the illustrated example, the peg 1061 provides a diameter (e.g., 3-5 mm, e.g., 4 mm) that is larger than a diameter of the rotor 1070 (e.g., 1-3 mm, e.g., 2 mm). The recess provided by the outwardly and upwardly extending wall portions 1035, 1036 of the bearing-housing structure 1030 allow the rotor cap, magnet and stator component to at least be partially nested within the bearing housing structure to provide a lower profile blower.

The top cover 1022 cooperates with the bearing-housing structure 1030 to define the volute 1039 that directs air towards the outlet 1025. As illustrated, the top cover 1022 includes a cylindrical, separating wall or baffle 1022(1) and together with the stepped configuration of the end portion 1037 separate the volute 1039 into two regions, i.e., a high speed airpath region 1070(1) and a low speed airpath region 1070(2), e.g., to minimize pressure pulsations and/or acoustic noise.

A seal 1095 (e.g., constructed of silicone rubber or other suitable material) may be provided between the bearing-housing structure 1030 and the top and bottom covers 1022, 1024, e.g., to provide a seal along the volute, support a PCB, and/or provide wire grommet for guiding PCB wires.

Further details and examples of aspects of the blower 1000, e.g., high speed and low speed airpath regions, are disclosed in PCT Publication No. WO 2011/062633, which is incorporated herein by reference in its entirety.

Figure 143:
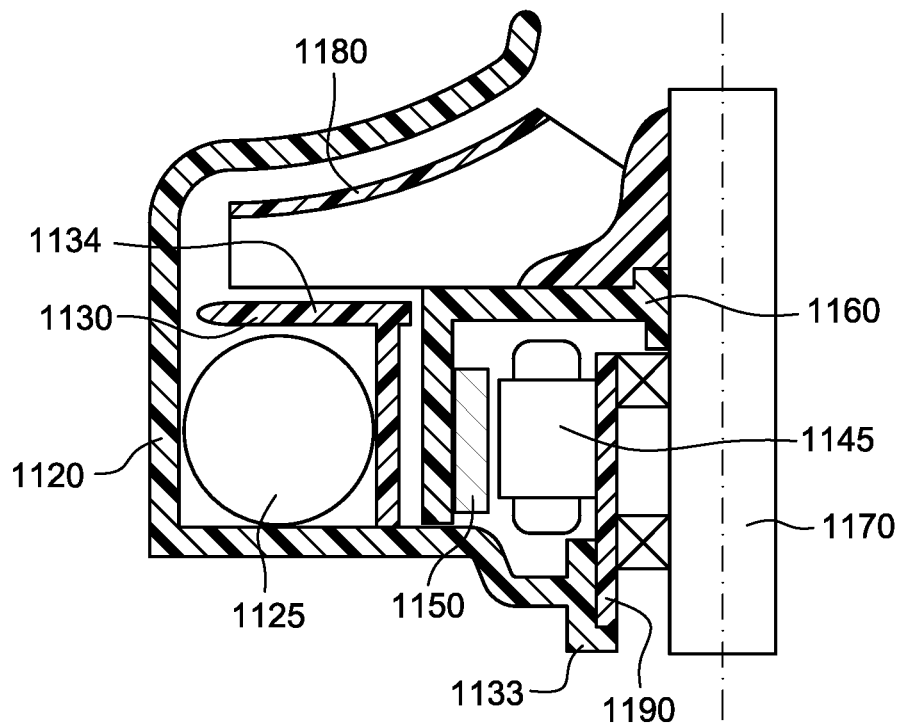
FIG. 143 is a cross-sectional view of a blower according to another example of the present technology.
Figure 147:
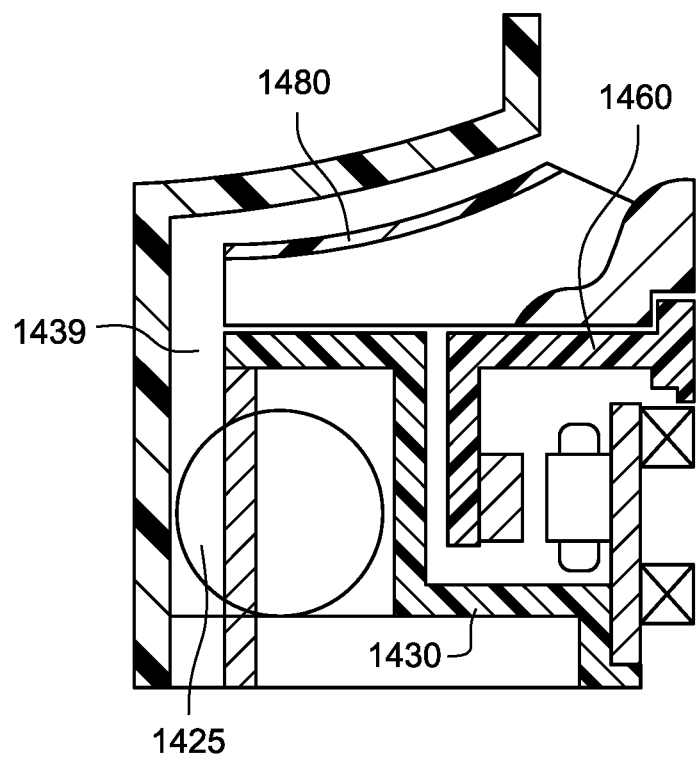
FIG. 147 is a cross-sectional view of a blower according to another example of the present technology.
Figure 148:
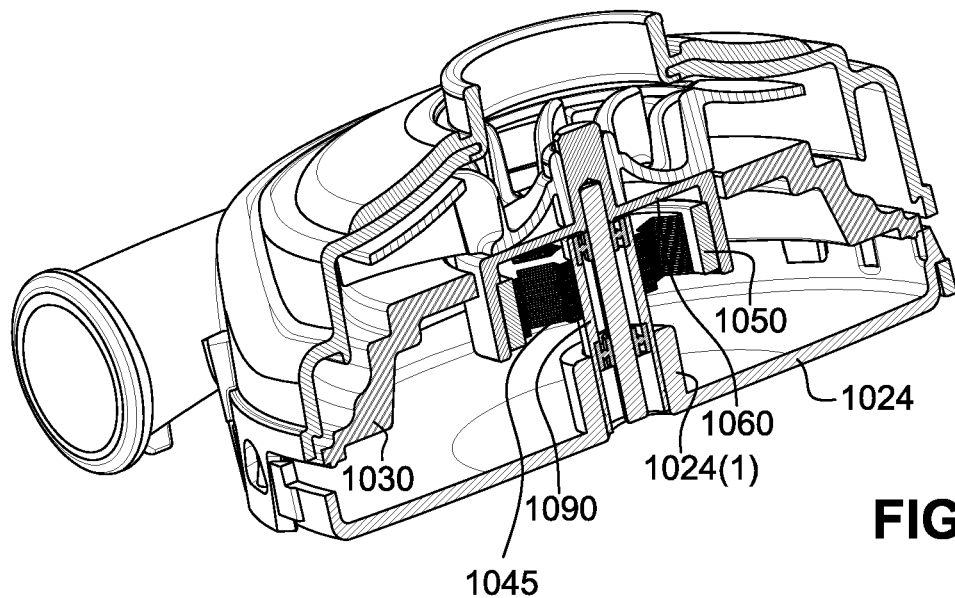
FIG. 148 is a cross-sectional view of a blower according to another example of the present technology.
Figure 149:
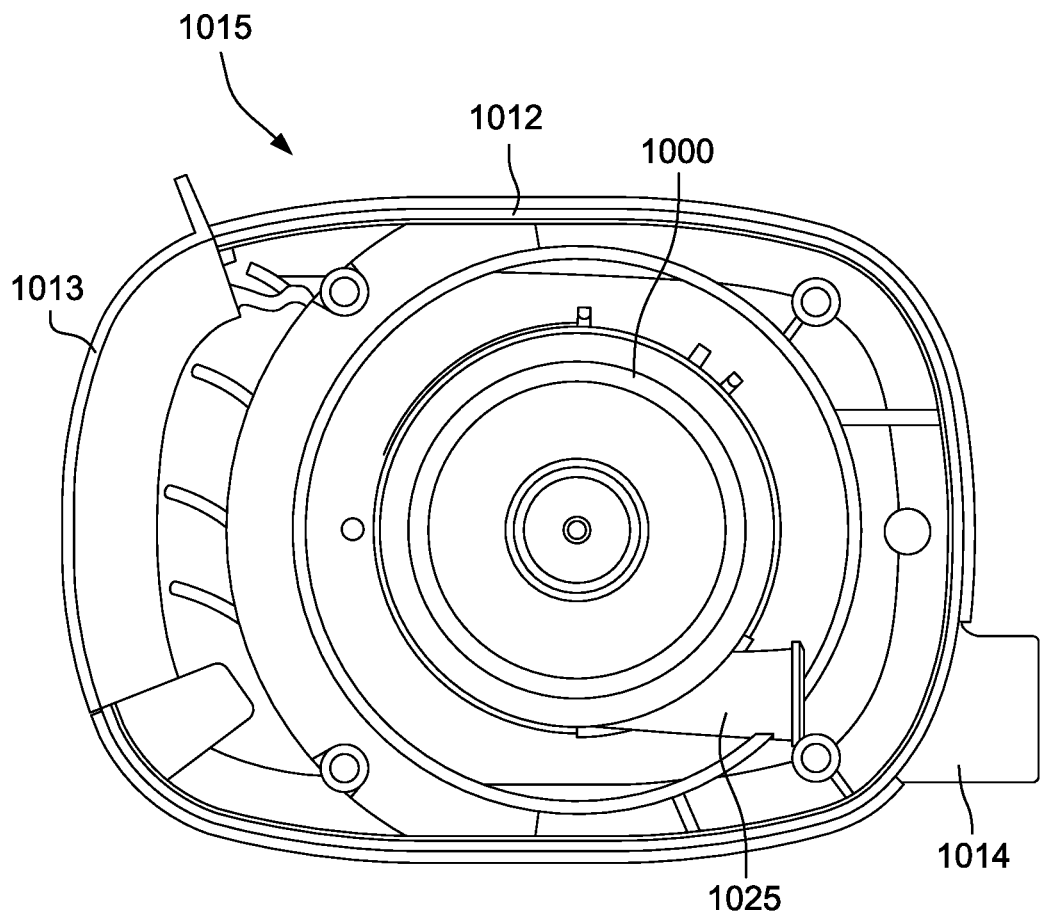
FIGS. 149 and 150 show a blower mounted within the casing of a PAP device according to an example of the present technology.
Figure 150:
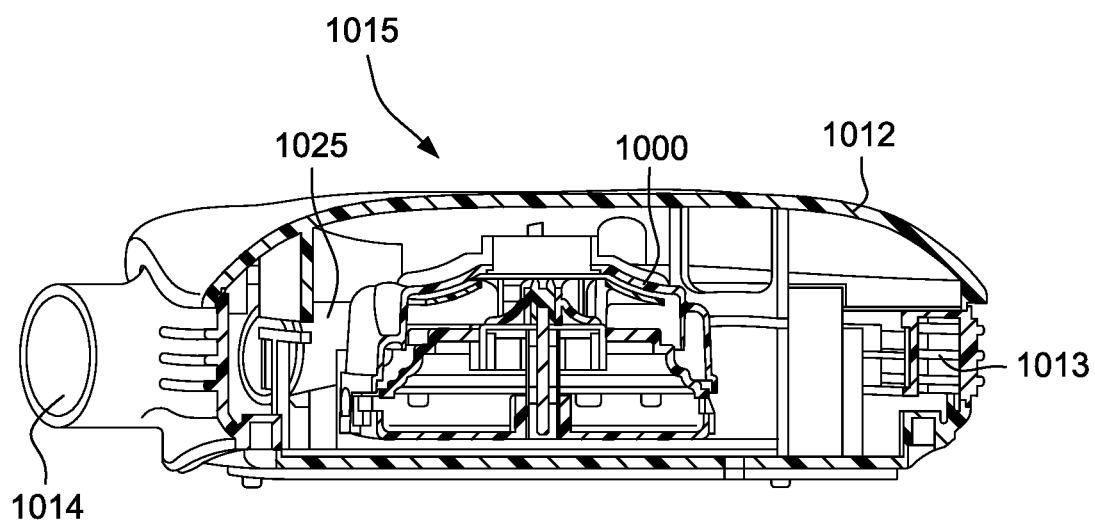

FIG. 148 shows another blower example similar to that shown in FIGS. 139 to 142. In contrast, the bottom cover 1024 of the blower 1000 provides a tube portion 1024(1) supports an end of the bearing cartridge 1090. In this example, the bearing-housing structure 1030 includes a central opening that allows the rotor cap 1060, magnet 1050 and stator component 1045 to at least be partially nested within the bearing housing structure. FIGS. 149 and 150 show such blower 1000 mounted within the casing 1012 of a PAP device 1015 according to an example of the present technology. As illustrated, the inlet 1013 and outlet 1014 are provided on opposite ends of the casing, FIGS. 143-147 and 151 show alternative examples of blowers including an outlet that is tangential to the inlet. In FIG. 143, the impeller 1180 is supported along the upper wall of the rotor cap 1160. The rotor cap 1160 (also supporting magnet 1150) is provided to the rotor 1170 rotatably supported by the bearing cartridge 1190. In this example, the housing 1120 includes a tube portion 1133 that supports the bearing cartridge 1190. The stator component 1145 is provided along the exterior surface of the bearing cartridge 1190. A stationary component 1130 is provided within the housing 1120 to provide a disk 1134 (e.g., to prevent blade pass tonal noise) and define the volute for directing air towards the outlet 1125.

Figure 144:
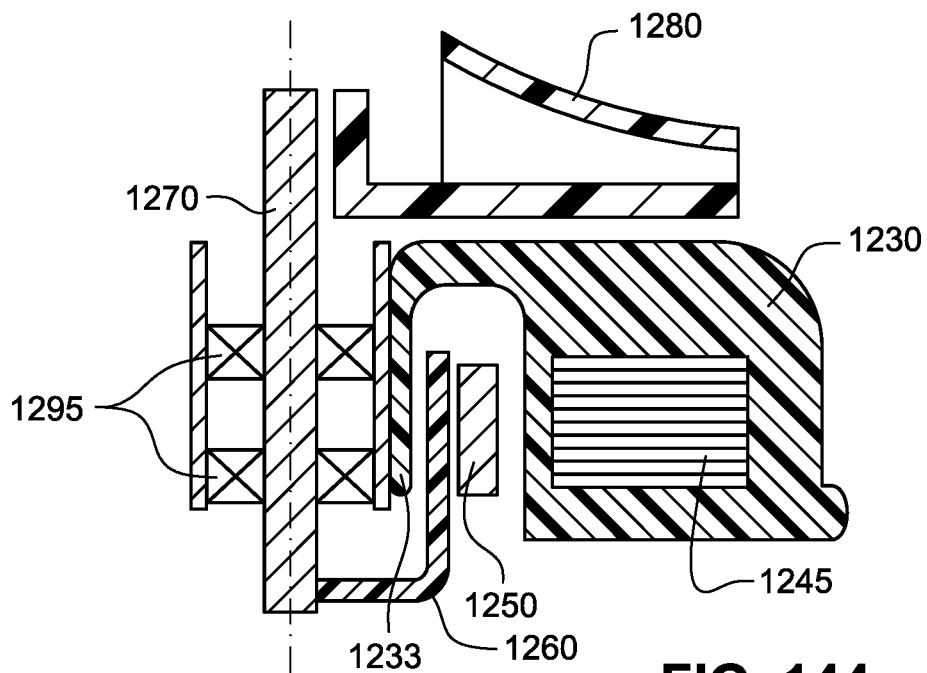
FIG. 144 is a cross-sectional view of a blower according to another example of the present technology.

In FIG. 144, the bearing-housing structure 1230 is integrated with the stator component 1245 of the motor, e.g., by overmolding, to form a one-piece structure. The bearing-housing structure 1230 provides a tube portion 1233 that supports bearings 1295 that rotatably support the rotor 1270. The rotor cap 1260 is provided to one end of the rotor 1270 and supports magnet 1250 in an operative position with respect to the stator component 1245 integrated with the bearing-housing structure 1230. The impeller 1280 is provided to the opposite end of the rotor 1270.

Figure 145:
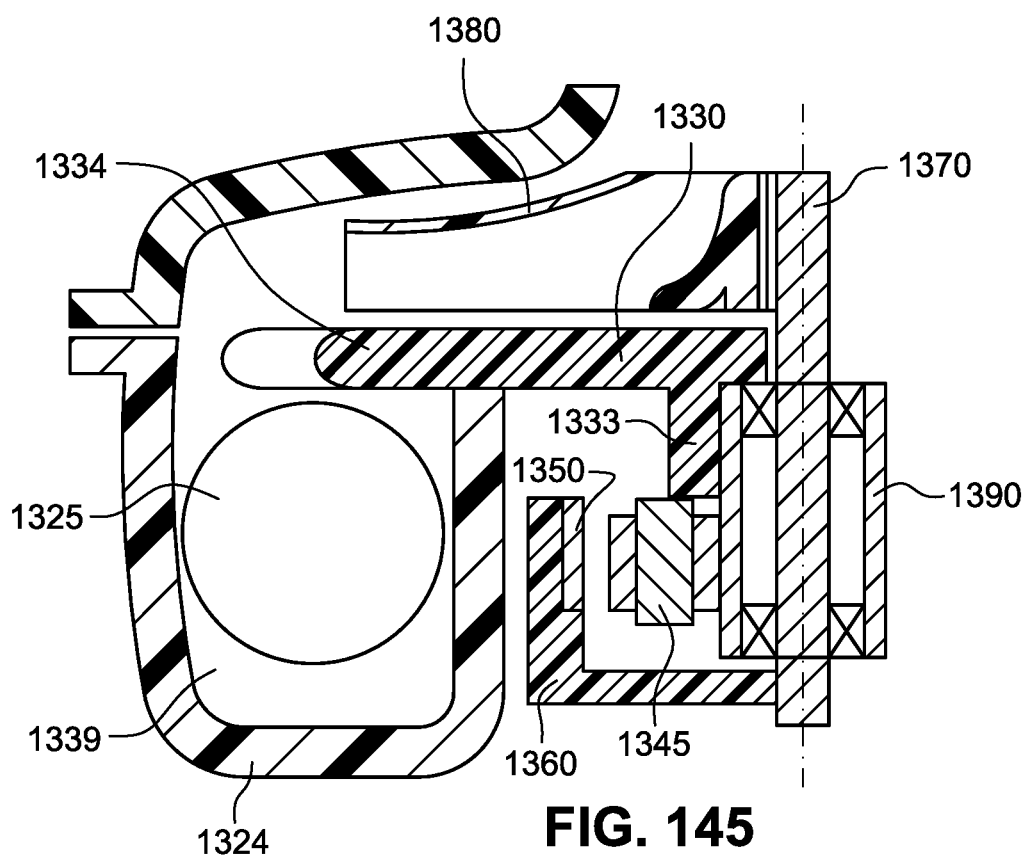
FIG. 145 is a cross-sectional view of a blower according to another example of the present technology.

In FIG. 145, the bottom cover 1324 of the housing is structured to define the volute 1339 for directing air towards the outlet 1325. The bottom cover 1324 also supports the bearing-housing structure 1330 including a tube portion 1333 that supports the bearing cartridge 1390 and a disk 1334. The stator component 1345 is provided along the exterior surface of the bearing cartridge 1390. The rotor cap 1360 (supporting magnet 1350) is provided to one end of the rotor 1370 and the impeller 1380 is provided to the opposite end of the rotor 1370.

Figure 146:
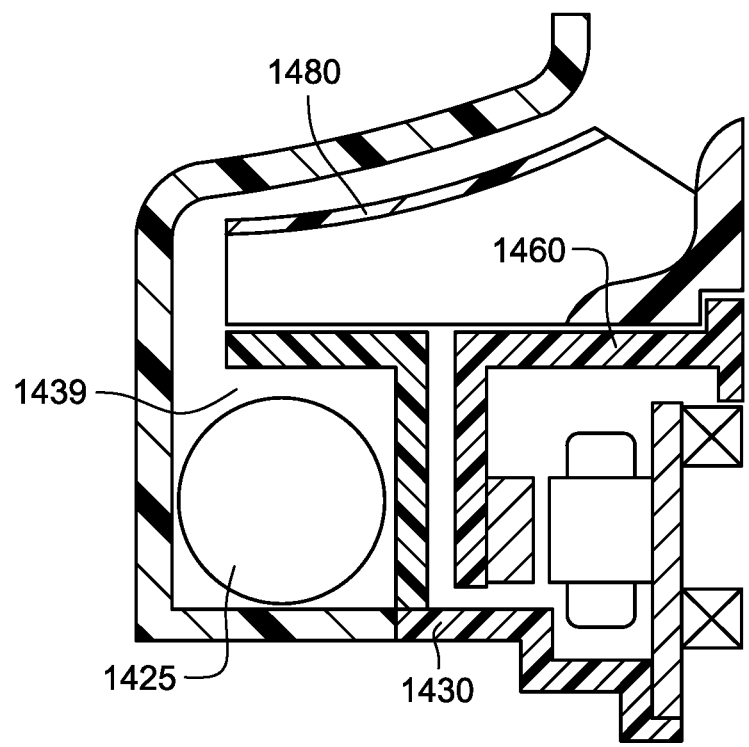
FIG. 146 is a cross-sectional view of a blower according to another example of the present technology.

FIGS. 146 and 147 show alternative examples of a bearing-housing structure 1430 including one or more walls defining the volute 1439 for directing air towards the outlet 1425. Similar to examples described above, the impeller 1480 is provided along the upper wall of the rotor cap 1460, and the motor components (e.g., rotor cap, magnet and stator component) are at least partially nested within the bearing housing structure.

Figure 151:
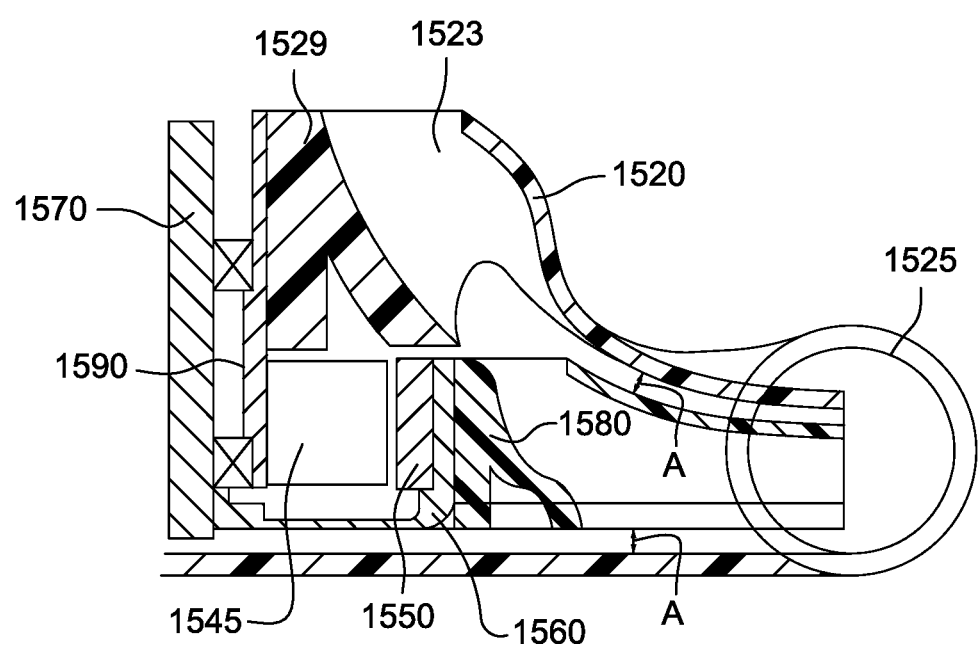
FIG. 151 is a cross-sectional view of a blower according to another example of the present technology.

In FIG. 151, the housing 1520 provides a generally annular-shaped inlet 1523 and an outlet 1525 that is tangential to the inlet. The inner housing part 1529 supports the bearing cartridge 1590 adapted to rotatably support the rotor 1570. The rotor cap 1560 (supporting the magnet 1550 and impeller 1580) is provided to an end portion of the rotor 1570. The stator component 1545 is provided along the exterior surface of the bearing cartridge 1590. In an example, the gap A between the impeller 1580 and an upper part of the housing 1520 and the gap A between the impeller 1580/rotor cap 1560 and a lower part of the housing 1520 is about 0.75 to 1.0 mm.

Impeller

Figure 14:
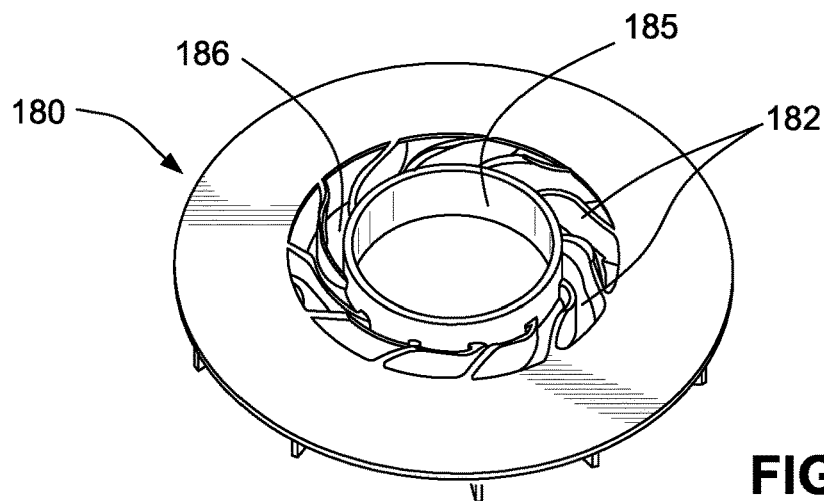
FIG. 14 is a perspective view of an impeller of the blower of FIG. 2.
Figure 15:
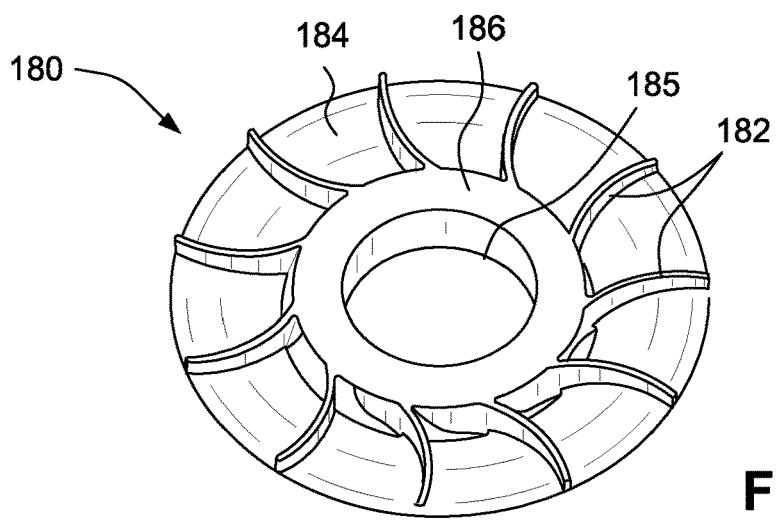
FIG. 15 is a reverse perspective view of the impeller of FIG. 14.

In the illustrated example, as shown in FIGS. 14 and 15, the impeller 180 (also referred to as a double-shrouded impeller or alternating-shroud impeller) includes a plurality of continuously curved or straight blades 182 sandwiched between a pair of disk-like shrouds 184, 186. As illustrated, the blades curve in towards the hub having an S-like shape. The shape is designed to reduce vortex shedding. Also, the shrouds may not fully cover the top and bottom surfaces of the blades. The lower shroud 186 incorporates the hub 185 that is adapted to receive the rotor cup 160, e.g., press-fit. Also, the impeller includes a tapered configuration wherein the blades taper towards the outer edge. In an example, the impeller may be constructed of a plastic material, e.g., Lexan®. Further details of impellers are disclosed in WO 2007/048206 A1, which is incorporated herein by reference in its entirety.

In certain examples, the impeller blades 182 may be curved in a generally clockwise direction. In an alternative example, the impeller blades 182 may be curved in a generally counter-clockwise direction.

Figure 93:
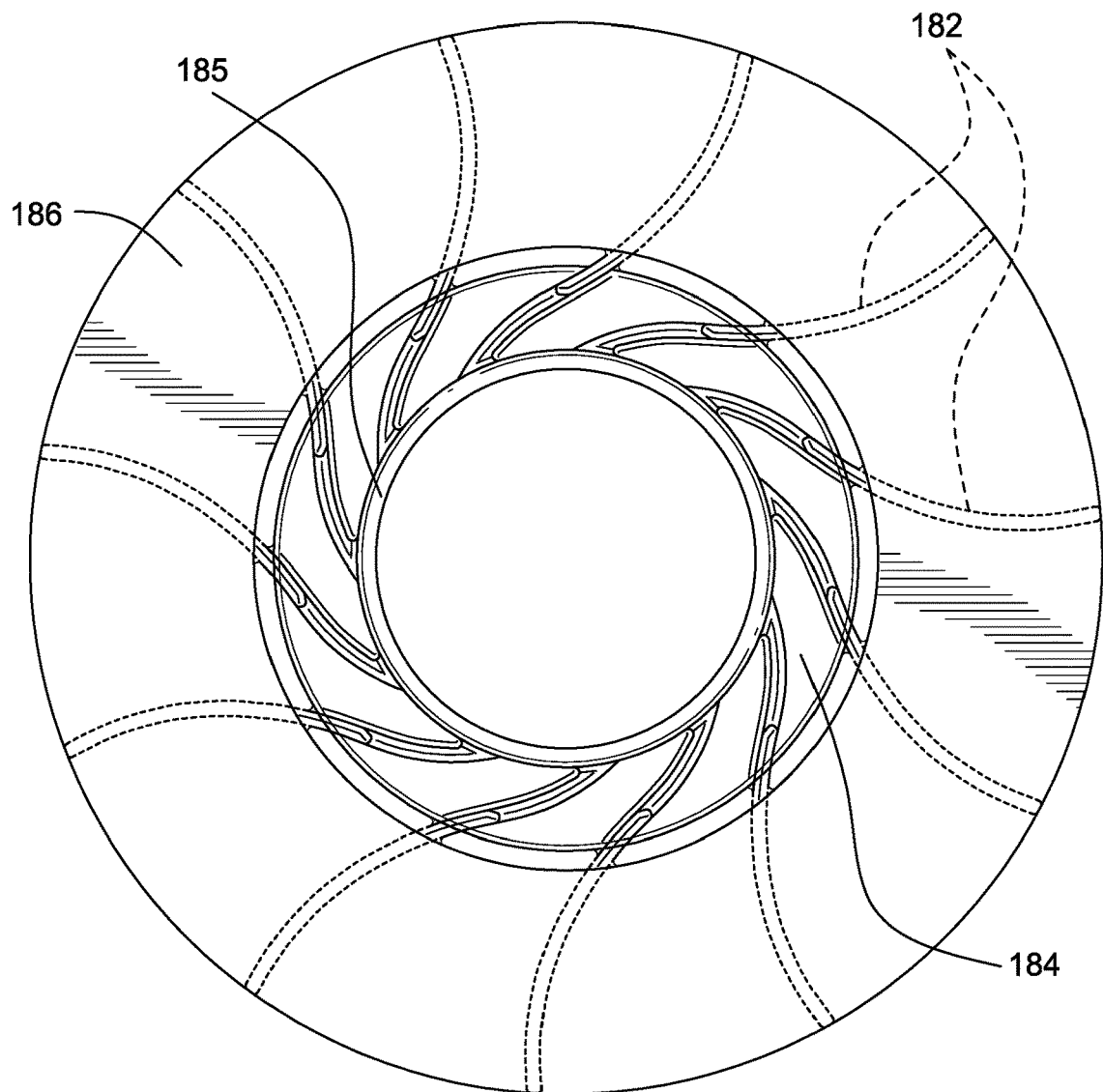
FIGS. 93 and 94 show an impeller an impeller blade according to an example of the present technology.
Figure 94:
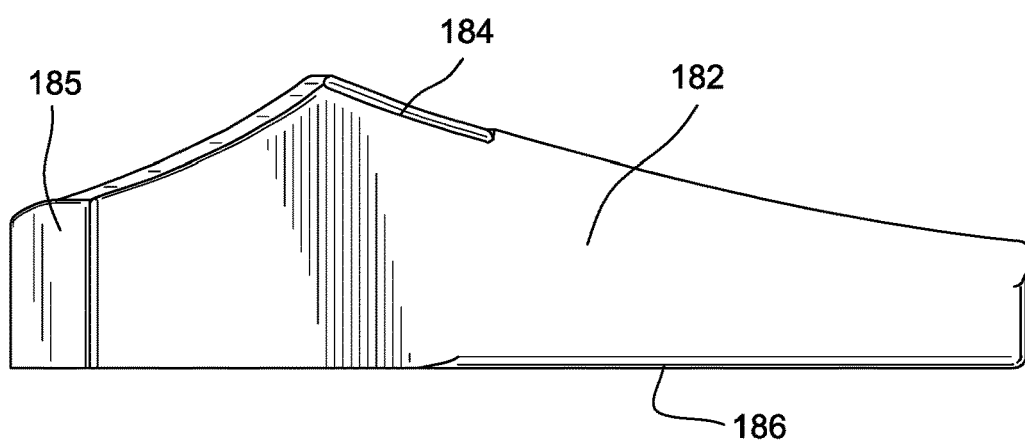

In an alternative example, as shown in FIGS. 93 and 94, a bottom shrouded impeller (i.e., bottom surface of blades 182 covered by a lower shroud 186) may be used, e.g., to help prevent impeller lifting off the shaft or rotor in use. FIG. 93 illustrates an example of the S-like shape of the blades 182. The slight S-shape at the beginning of each blade is a result of having the blades attach to the hub and not block the inflow.

Figure 95:
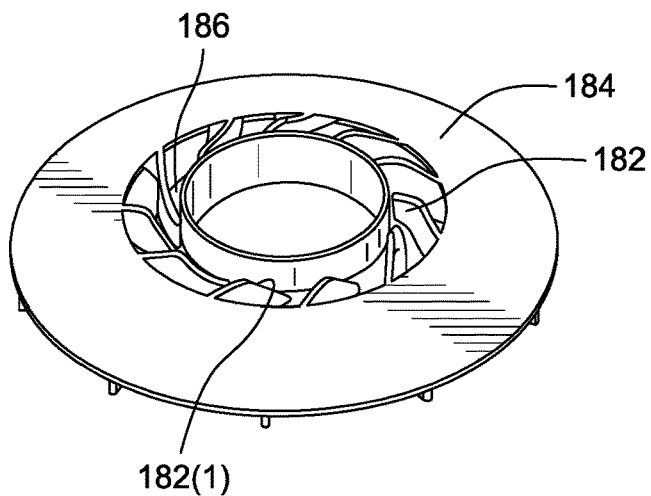
FIGS. 95 and 96 show an impeller and an impeller blade according to another example of the present technology.
Figure 96:
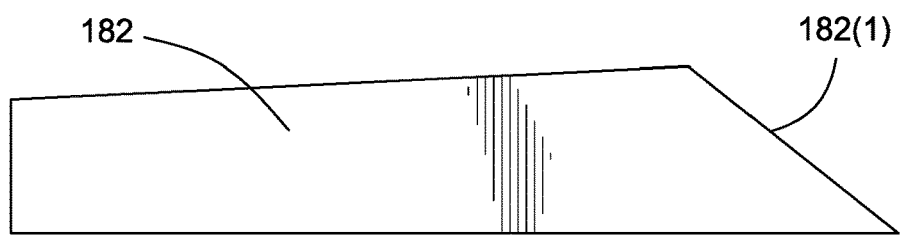

As shown in FIGS. 95 and 96, the leading edges 182(1) of the impeller blades 182 may have a sweptback configuration in that the leading edges of the impeller blades are slanted or angled back inwards in the opposite direction of the flow. This configuration provides a longer blade length providing higher pressures, reduces drag at the impeller leading edge and/or causing streamwise vortices to be formed in the flow path which can delay the flow separation, thus reducing drag and flow oscillations and increased efficiency. In an example, the blade height at the leading edge may increase at an angle of about 10-50°, e.g., 20°, along the length of the blade to a point about ¼ of the length of the vane.

Figure 97:
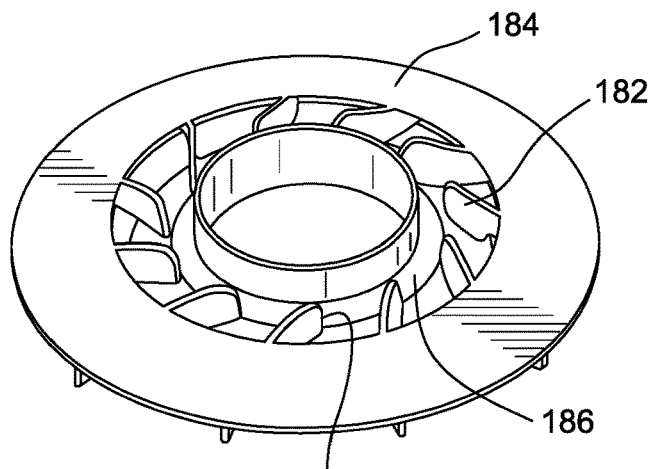
FIGS. 97 and 98 show an impeller and an impeller blade according to another example of the present technology.
Figure 98:
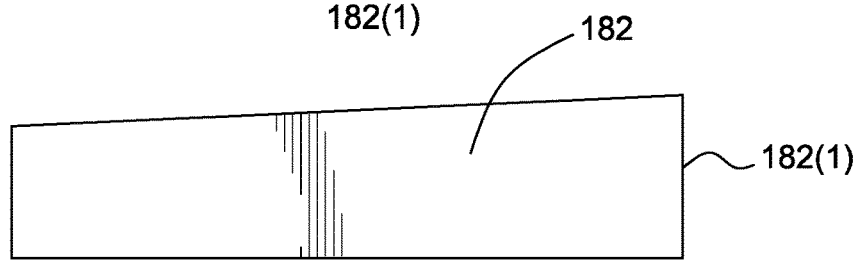

Alternatively, as shown in FIGS. 97 and 98, the impeller blades 182 may have a leading edge 182(1) that is normal to the flow direction as in conventional impellers. It should be appreciated that the blade and vane angles may be selected for different conditions and/or performance optimizations.

The impeller may have a rotor portion integrated therein. The rotor portion is configured to interact with the magnet by serving as a path for the magnetic flux to cause rotation of the impeller through interaction with the stator. The rotor component of the impeller may be a single-piece construction or it may be formed as an cylindrical insert of magnetic steel within a non-ferrous structure of plastic or other non-magnetic material that could be the impeller itself; such an insert could be attached by various methods including overmolding, an interference press fit, or adhesive bonding. The insert or ring of ferrous material would retain the impeller on the stator in use. In an example, there is no fastening of the impeller to the stator—the impeller 180 and rotor cap 160 are retained by a magnetic attraction between the magnet 150 (coupled to the interior surface of the rotor cap) and the stator assembly 145.

Figure 113:
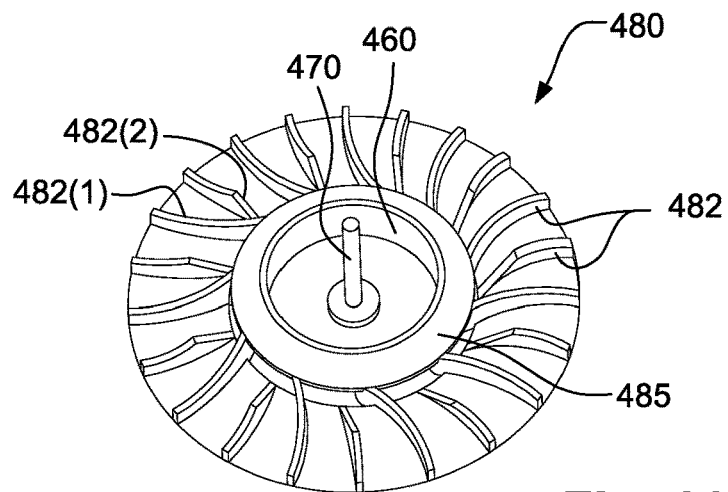
FIG. 113 shows an impeller according to another example of the present technology.
Figure 114:
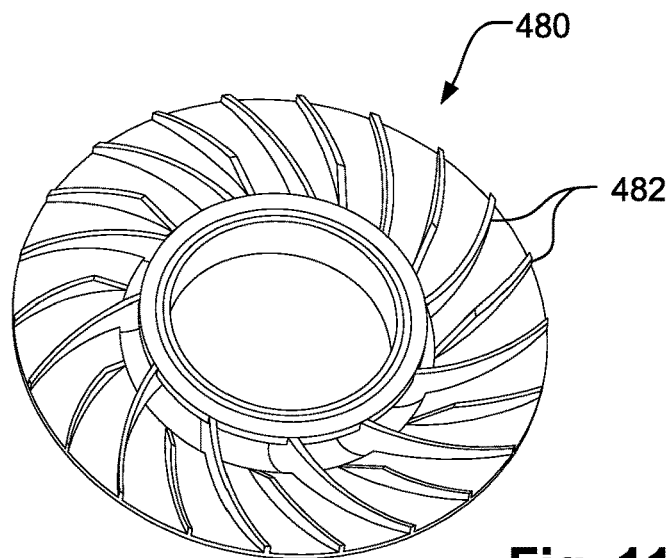
FIG. 114 shows an impeller according to another example of the present technology.
Figure 115:
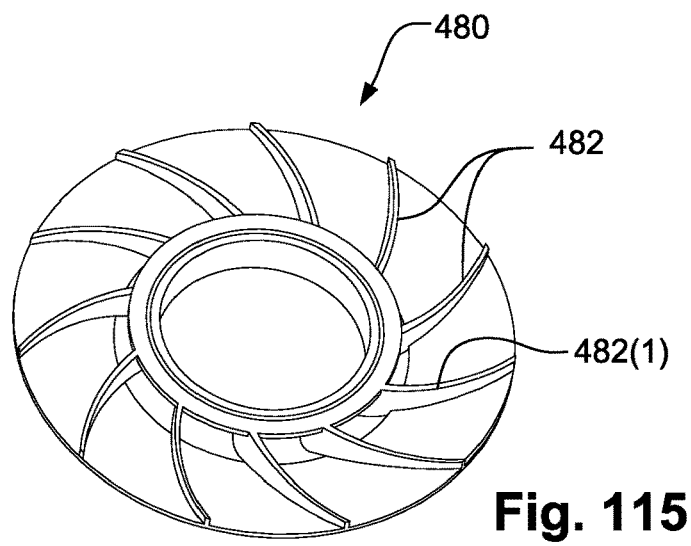
FIG. 115 shows an impeller according to another example of the present technology.
Figure 116:
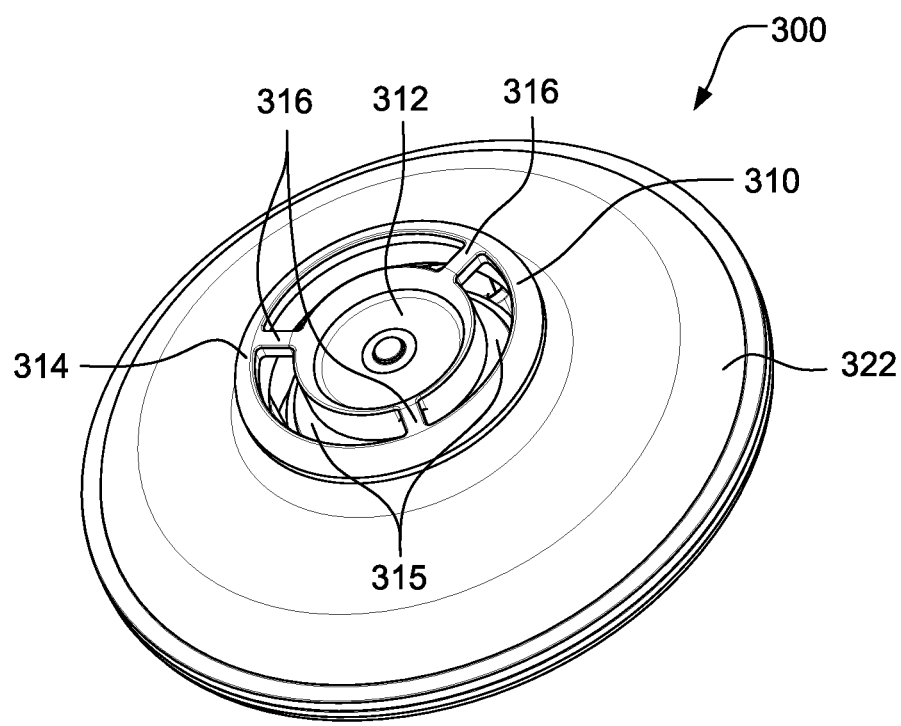
FIGS. 116 to 119 show various views of a blower including an inlet cap according to an example of the present technology.
Figure 117:
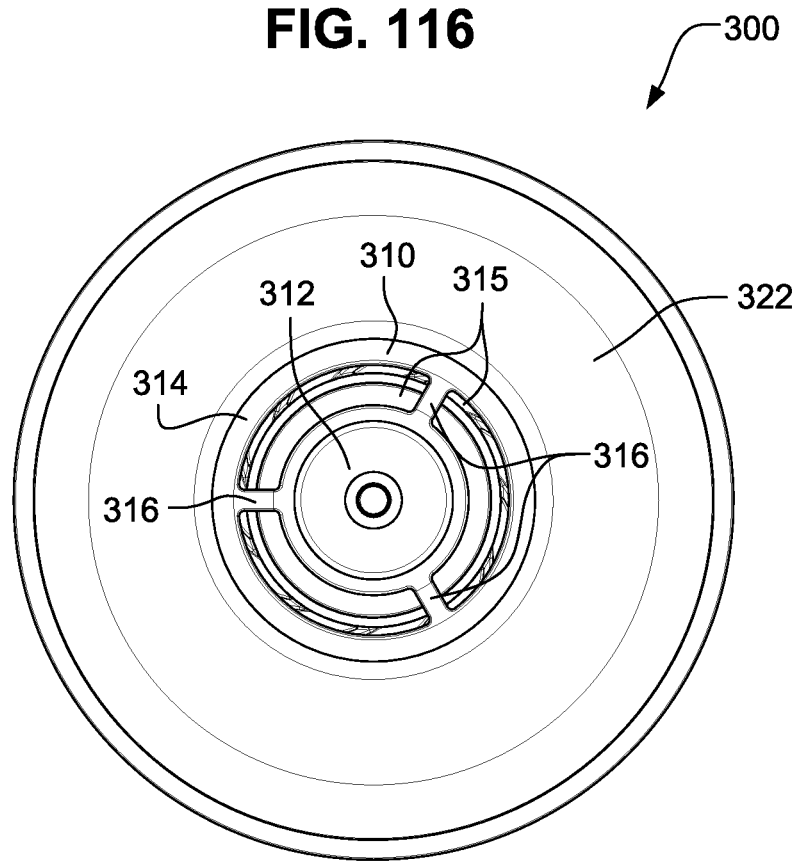
Figure 118:
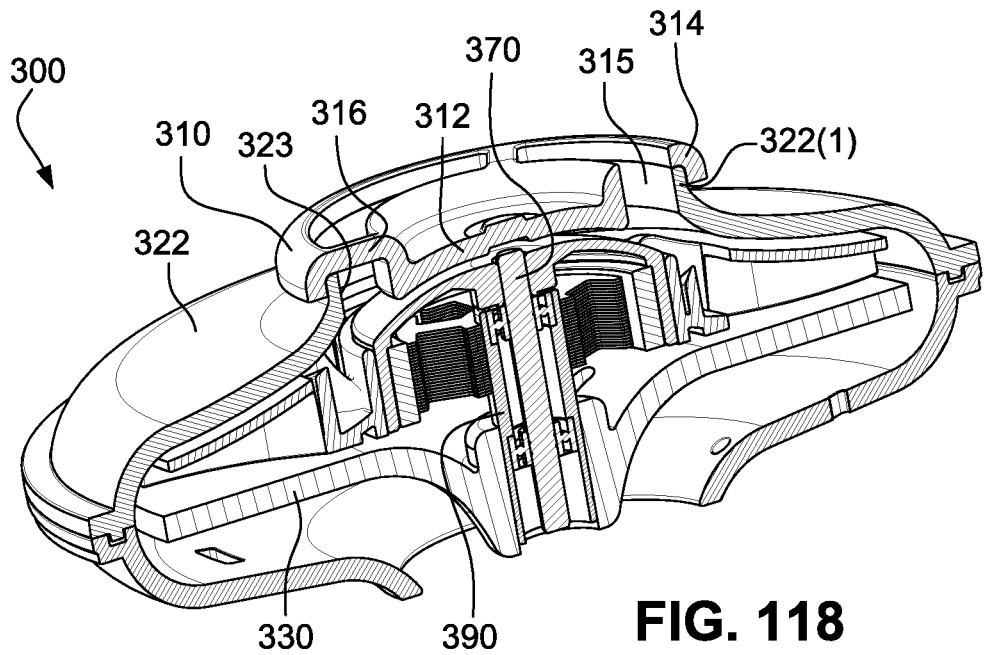
Figure 119:
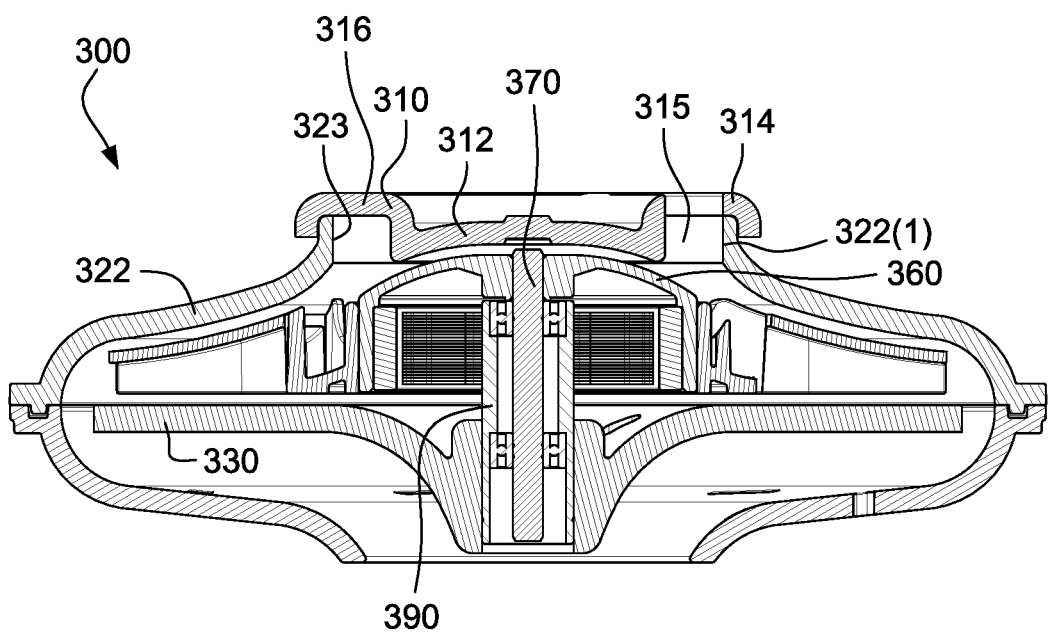

FIGS. 113 to 115 show impellers according to alternative examples of the present technology. In FIG. 113, the impeller 480 includes a larger number of blades 482 than examples disclosed above, e.g., 22 blades, to reduce noise by reducing tonal frequencies. However, it should be appreciated that more or less blades are possible. Also, each blade 482 includes a curved configuration and is curved in a generally clock-wise direction, e.g., to reduce broadband and tonal noise. However, as shown in FIG. 114, the blades 482 of the impeller 480 may be curved in the opposite direction, i.e., curved in a generally counter-clock-wise direction. FIG. 115 shows another example of an impeller 480 including 11 blades 482 with each blade curved in a generally counter-clock-wise direction.

In FIGS. 113 and 114, every other blade includes a top edge 482(1) along its length that tapers towards the outer edge. The remaining blades in FIGS. 113 and 114 include a top edge 482(2) that gradually increases in height from the hub before tapering towards the outer edge. In FIG. 115, all the blades include a top edge 482(1) along its length that tapers towards the outer edge. However, it should be appreciated that other blade configurations are possible.

FIG. 113 shows a rotor cap 460 along with rotor 470 provided to the hub 485 of the impeller 480, e.g., with a press-fit.

Exemplary Dimensions

Figure 16:
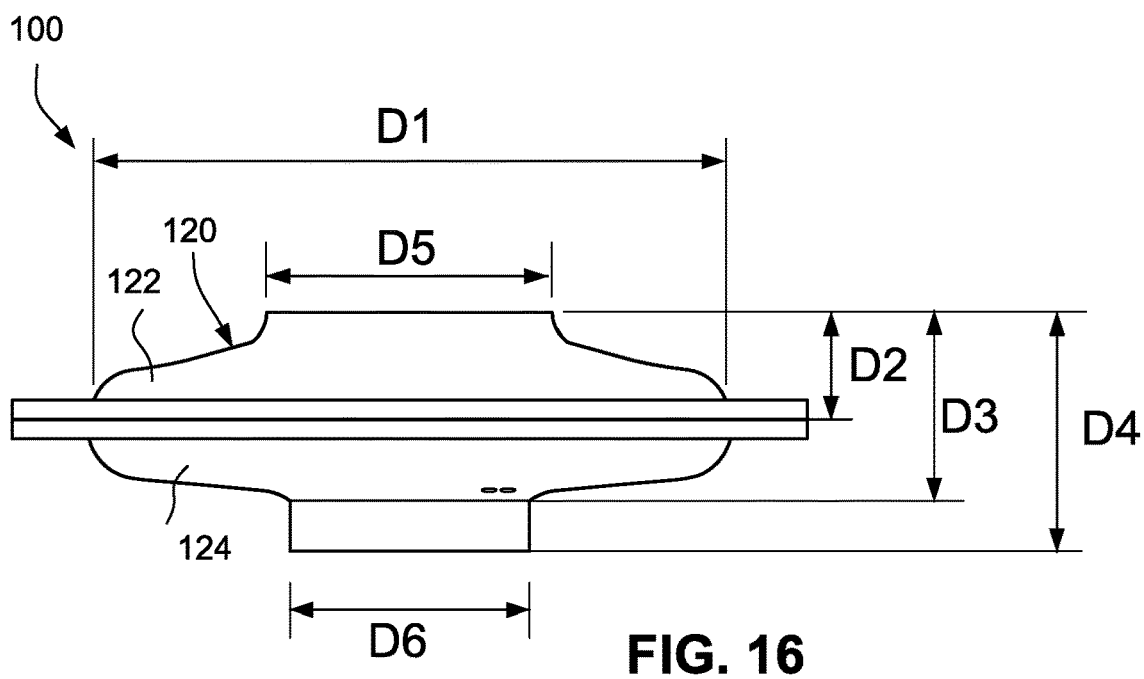
FIG. 16 is a side view of the blower of FIG. 2 showing exemplary dimensions according to an example of the present technology.

In an example, as shown in FIG. 16, D1 may be about 50-70 or more, about 60-65 mm, e.g., about 62.8 mm, D2 may be about 8-13 mm or more, e.g., about 10.4 mm, D3 may be about 15-20 mm or more, e.g., about 18.4 mm, D4 may be about 15-25 mm or more, e.g., about 23.2 mm, D5 may be about 20-30 mm, e.g., about 27 mm, and D6 may be about 20-25 mm, e.g., about 21 mm. It is to be understood that these dimensions and ranges are merely exemplary and other dimensions and ranges are possible depending on application. For example, ranges that vary from those provided +/−10% or more may be suitable for particular applications.

PAP Systems

Certain examples relate to PAP systems that comprise a blower as described herein. In certain examples, the blower may be mounted on the patient's head (e.g., on the crown of the patient's head or on the front portion of a patient's head), patient's arm, chest, or other body part, in or beside a pillow, in a scarf-like arrangement, incorporated into clothing, attached to a bed or bed head, etc. However, the PAP system may utilize the blower described herein in a more conventional PAP delivery device, e.g., of the type that includes a chassis or enclosure that is intended to rest on the user's bedside table.

While the present disclosure has been described in connection with certain examples, it is to be understood that the present disclosure is not to be limited to the disclosed examples, but on the contrary, is intended to cover various modifications and equivalent arrangements. For example, while the blower has been described in relation to an axial blower, the blower could also be configured as a tangential blower. Furthermore, the blower is described for use in a headworn PAP system, but it could also be used in conjunction with a more conventional PAP system that includes a separate flow generator that is not mounted on the user's head or body. Also, the various examples described herein may be implemented in conjunction with other examples, e.g., aspects of one example may be combined with aspects of another example to realize yet other examples. Further, each independent feature or component of any given assembly may constitute an additional example. In addition, while the present disclosure has particular application to patients who suffer from OSA, it is to be appreciated that patients who suffer from other illnesses (e.g., congestive heart failure, diabetes, morbid obesity, stroke, bariatric surgery, etc, or combinations thereof) may derive benefit from the teachings of this disclosure. Moreover, the teachings of this disclosure have applicability with patients and non-patients alike in non-medical applications.

What is claimed is:

1. A blower, comprising:
   a housing including an inlet and an outlet;
   a motor provided to the housing and configured to drive a rotor;
   an impeller provided to the rotor,
   wherein the impeller is supported on the rotor by a rotor cap; and
   an inlet cap provided to the inlet of the housing, the inlet cap configured to occlude or block at least a central portion of the inlet,
   wherein the inlet cap includes a generally disk-shaped inner portion configured to occlude or block at least the central portion of the inlet, a generally ring-shaped outer portion configured to support the inlet cap at the inlet, and spokes or connectors that interconnect the inner and outer portions, and
   wherein the housing includes a top cover forming the inlet and configured to cover the impeller, and wherein a clearance between the rotor cap and the generally disk-shaped inner portion of the inlet cap is substantially similar to a clearance between the impeller and the top cover.

2. The blower according to claim 1, further comprising a bearing-housing structure provided to the housing and configured to rotatably support the rotor.

3. The blower according to claim 2, wherein the bearing-housing structure includes a housing part and a bearing cartridge is provided to the housing part, the bearing cartridge including a tubular sleeve and two spaced-apart bearings supported within the sleeve to support the rotor.

4. The blower according to claim 1, wherein the inlet cap is integrally formed in one-piece with the housing.

5. The blower according to claim 1, wherein the inlet cap is formed separately from the housing and attached or otherwise provided to the inlet of the housing.

6. The blower according to claim 1, wherein the connectors extend radially from the inner portion to the outer portion.

7. The blower according to claim 1, wherein the connectors extend tangentially from the inner portion to the outer portion.

8. The blower according to claim 1, wherein the connectors include a curved configuration.

9. The blower according to claim 1, wherein the connectors are in the form of cylinders.

10. The blower according to claim 1, wherein the inlet cap forms an annular gap between an outer edge of the inner portion and an inner edge of the outer portion configured to receive a supply of gas.

11. A PAP device comprising the blower according to claim 1.

12. A PAP system comprising the PAP device according to claim 11, a patient interface configured to form a seal with a patient's face, and air delivery tubing to interconnect the patient interface and the PAP device.

13. The blower according to claim 1, wherein the generally disk-shaped inner portion includes a diameter that is less than a diameter of the rotor cap.

14. The blower according to claim 1, wherein the motor includes a stator assembly, and the rotor cap includes an interior surface that supports a magnet and an exterior surface that supports the impeller, and wherein the rotor cap is engaged with the rotor such that the stator assembly acts on the magnet to cause spinning movement of the rotor cap and hence the impeller in use.

15. The blower according to claim 1, wherein the generally disk-shaped inner portion is axially recessed or offset relative to the generally ring-shaped outer portion.

* * * * *